(12) United States Patent
Gaudernack et al.

(10) Patent No.: US 12,071,467 B2
(45) Date of Patent: Aug. 27, 2024

(54) SPECIFIC BINDING MOLECULES FOR hTERT

(71) Applicant: OSLO UNIVERSITETSSYKEHUS HF, Oslo (NO)

(72) Inventors: Gustav Gaudernack, Sandvika (NO); Gunnar Kvalheim, Oslo (NO); Else Marit Inderberg, Oslo (NO); Sébastien Wälchli, Oslo (NO)

(73) Assignee: OSLO UNIVERSITETSSYKEHUS HF, Oslo (NO)

( * ) Notice: Subject to any disclaimer, the term of this patent is extended or adjusted under 35 U.S.C. 154(b) by 975 days.

(21) Appl. No.: 16/975,645

(22) PCT Filed: Feb. 27, 2019

(86) PCT No.: PCT/EP2019/054798
§ 371 (c)(1),
(2) Date: Nov. 24, 2020

(87) PCT Pub. No.: WO2019/166463
PCT Pub. Date: Sep. 6, 2019

(65) Prior Publication Data
US 2023/0192804 A1    Jun. 22, 2023

(30) Foreign Application Priority Data

Feb. 27, 2018  (GB) .................................. 1803178

(51) Int. Cl.
*A61K 35/17*    (2015.01)
*C07K 14/725*   (2006.01)
*C12N 5/0783*   (2010.01)

(52) U.S. Cl.
CPC .......... *C07K 14/7051* (2013.01); *A61K 35/17* (2013.01); *C12N 5/0636* (2013.01); *C07K 2319/03* (2013.01); *C12N 2501/2302* (2013.01); *C12N 2501/51* (2013.01); *C12N 2501/515* (2013.01)

(58) Field of Classification Search
CPC .................................................... A61K 35/17
See application file for complete search history.

(56) References Cited

U.S. PATENT DOCUMENTS

| 5,827,642 | A  | 10/1998 | Riddell et al. |
| 6,040,177 | A  | 3/2000  | Riddell et al. |
| 6,797,514 | B2 | 9/2004  | Berenson et al. |
| 6,867,041 | B2 | 3/2005  | Berenson et al. |
| 6,905,874 | B2 | 6/2005  | Berenson et al. |
| 7,569,664 | B2 | 8/2009  | Jakobsen et al. |
| 2009/0042798 | A1 | 2/2009 | Wang et al. |

FOREIGN PATENT DOCUMENTS

| CN | 106 478 808 A | 3/2017 |
| WO | 2000/031239 A1 | 6/2000 |
| WO | 2002/082908 A1 | 10/2002 |
| WO | 2002/083080 A2 | 10/2002 |
| WO | 2002/087341 A1 | 11/2002 |
| WO | 2003/038047 A2 | 5/2003 |
| WO | 2004/000220 A2 | 12/2003 |
| WO | 2004/054512 A2 | 7/2004 |
| WO | 2005/116646 A1 | 12/2005 |
| WO | 2006/125962 A2 | 11/2006 |
| WO | 2010/003520 A2 | 1/2010 |
| WO | 2012/079000 A1 | 6/2012 |
| WO | 2012/129514 A1 | 9/2012 |
| WO | 2014/037422 A1 | 3/2014 |
| WO | 2014/196841 A1 | 12/2014 |
| WO | 2016/116601 A1 | 7/2016 |
| WO | 2016/147145 A1 | 9/2016 |
| WO | 2017/011804 A1 | 1/2017 |
| WO | 2017/118745 A1 | 7/2017 |
| WO | 2017/207814 A1 | 12/2017 |

(Continued)

OTHER PUBLICATIONS

Bridgeman et al. (J.Immunol. Jun. 15, 2010; 184 (12): 6938-49).*
Ma et al. (Prostate. Sep. 15, 2004; 61 (1): 12-25).*
Hudecek et al. (Clin. Cancer Res. Jun. 15, 2013; 19 (12): 3153-64).*
Bernhardt et al. (Br. J. Cancer. Dec. 4, 2006; 95 (11): 1474-82).*
Sandri et al. (Cancer Res. May 1, 2016; 76 (9): 2540-51).*
Stone et al. (Cancer Immunol. Immunother. Nov. 2014; 63 (11): 1163-76).*
Walseng et al. (PLoS One. 2015; 10 (4): e0119559; pp. 1-15).*
Walseng et al. (Sci. Rep. Sep. 6, 2017; 7 (1): 10713; pp. 1-10).*
Willemsen et al. (Gene Ther. Aug. 2000; 7 (16): 1369-77).*
Berntzen et al. (J. Immunol. Methods. Mar. 2005; 298 (1-2): 93-104).*
Chen et al. (Immunology. Sep. 2018; 155 (1): 123-136).*

(Continued)

*Primary Examiner* — Stephen L Rawlings
(74) *Attorney, Agent, or Firm* — McDonnell Boehnen Hulbert & Berghoff LLP

(57) ABSTRACT

The present invention provides a nucleic acid molecule encoding a specific binding molecule capable of binding an h TERT peptide comprising the amino acid sequence set forth in SEQ ID NO: 1 when the peptide is presented by a Class II Major Histocompatibility Complex (MHC), wherein the specific binding molecule comprises a first polypeptide comprising a variable region of an α-chain and a second polypeptide comprising a variable region of a β-chain of a T-cell receptor (TCR), and wherein: (a) the variable region of an α-chain comprises CDR sequences CDR1, CDR2 and CDR3 which respectively comprise the amino acid sequences set forth in SEQ ID NOs: 2, 3 and 4; and (b) the variable region of a β-chain comprises CDR sequences CDR1, CDR2 and CDR3 which respectively comprise the sequences set forth in SEQ ID NOs: 5, 6 and 7. Recombinant constructs, vectors and host cells comprising such nucleic acid molecules are also provided, as are specific binding molecules encoded by such nucleic acid molecules. The present invention has utility in the treatment of cancer.

14 Claims, 11 Drawing Sheets

Figure 2:
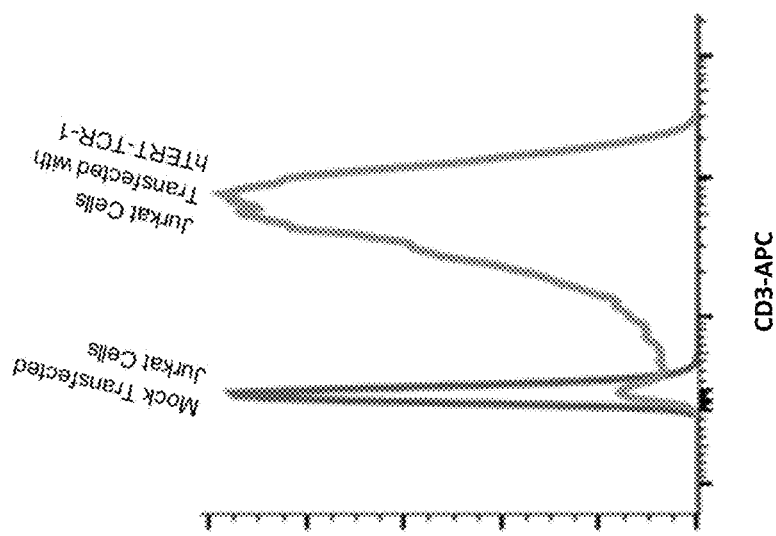

Specification includes a Sequence Listing.

(56) References Cited

FOREIGN PATENT DOCUMENTS

WO　　　2018/197492 A1　　11/2018

OTHER PUBLICATIONS

Bell et al. (J. Biol. Chem. Sep. 9, 1994; 269 (36): 22758-63).*

The International Search Report with Written Opinion for PCT/EP2019/054798, dated Apr. 5, 2019, pp. 1-18.

Roh, Jae-Il, et al., "Clinical Implications of Antitelomeric Drugs with Respect to the Nontelomeric Functions of Telomerase in Cancer", Oncotargets and Therapy, 2013, pp. 1161-1166.

Kyte, Jon Amund, "Cancer Vaccination with Telomerase Peptide GV1001", Expert Opinion on Investigational Drugs, 2009, vol. 18(5), pp. 687-694.

Kyte, Jon Amund, et al., "Unconventional Cytokine Profiles and Development of T Cell Memory in Long-Term Survivors After Cancer Vaccination", Cancer Immunology Immunotherapy, 2009, vol. 58(18), pp. 1609-1626.

Bernhardt, SL, et al., "Telomerase Peptide Vaccination of Patients with Non-Resectable Pancreatic Cancer: A Dose Escalating Phase I/II Study", British Journal of Cancer, 2006, vol. 95(11), pp. 1474-1482.

UKIPO Search Report from the Intellectual Property Office, dated Oct. 30, 2018, for International Application No. GB1803178.1, pp. 1-26.

Akbarzadeh, A. et al., "Liposome: Classification, Preparation, and Applications", Nanoscale Research Letters, 2013, vol. 8:102, pp. 1-9.

Almåsbak, H., et al., "Transiently Redirected T Cells for Adoptive Transfer", Cytotherapy, 2011, vol. 13, pp. 629-640.

Boulter, J.M., et al., "Stable, Soluble T-Cell Receptor Molecules for Crystallization and Therapeutics", Protein Engineering, 2003, vol. 16(9), pp. 707-711.

Busch, S.J., et al., "Dimers, Leucine Zippers and DNA-Binding Domains", Trends Genet., Feb. 1990, vol. 6(2), pp. 36-40.

Castelli, F.A., et al., "HLA-DP4, the Most Frequent HLA II Molecule, Defines a New Supertype of Peptide-Binding Specificity", J. Immunol., 2002, vol. 169, pp. 6928-6934.

Cohen, C.J., et al., "Enhanced Antitumor Activity of T Cells Engineered to Express T-Cell Receptors with a Second Disulfide Bond", Cancer Res., Apr. 15, 2007, vol. 67(8), pp. 3898-3903.

Dillard, P., et al., "Exploiting CD4 T Cells for Adoptive Cell Therapy in Cancer", Department of Cellular Therapy, Oslo University Hospital—The Norwegian Radium Hospital, Oslo, Norway SITC Poster, Nov. 2017.

Galaine, J., et al., "Heparan Sulfate Proteoglycans Promote Telomerase Internalization and MHC Class II Presentation on Dendritic Cells", J. Immunol., 2016, vol. 197, pp. 1597-1608.

Gong, J-H., et al., "Characterization of a Human Cell Line (NK-92) with Phenotypical and Functional Characteristics of Activated Natural Killer Cells", Leukemia, Apr. 1994, vol. 8(4), pp. 652-658.

Inderberg, E.M., et al., "Tapping CD4 T Cells for Cancer Immunotherapy", Department of Cellular Therapy, Oslo University Hospital—The Norwegian Radium Hospital, Oslo, Norway, EuChemS YIW Presentation, Jul. 2017 Poster.

Kokhaei, P., et al., "Telomerase (hTERT 611-626) Serves as a Tumor Antigen in B-Cell Chronic Lymphocytic Leukemia and Generates Spontaneously Antileukemic, Cytotoxic T Cells", Experimental Hematology, 2007, vol. 35, pp. 297-301.

Kung, V.T. and Redemann, C.T, et al., "Synthesis of Carboxyacyl Derivatives of Phosphatidylethanolamine and Use as an Efficient Method for Conjugation of Protein to Liposomes", Biochimica et Biophysica Acta, 1986, vol. 862, pp. 435-439.

Lewis, J.E., et al., "The Use of a Viral 2A Sequence for the Simultaneous Over-Expression of Both the vgf Gene and Enhanced Green Fluorescent Protein (eGFP) in vitro and in vivo", Journal of Neuroscience Methods, 2015, vol. 256, pp. 22-29.

Lupton, S.D., et al., "Dominant Positive and Negative Selection Using a Hygromycin Phosphotransferase-Thymidine Kinase Fusion Gene", Molecular and Cellular Biology, Jun. 1991, vol. 11(6), pp. 3374-3378.

Maude, S.L., et al., "CD19-Targeted Chimeric Antigen Receptor T-Cell Therapy for Acute Lymphoblastic Leukemia", Blood, 2015, vol. 125(26), pp. 4017-4023.

Miyazaki, Y., et al., "Development of a Novel Redirected T-Cell-Based Adoptive Immunotherapy Targeting Human Telomerase Reverse Transcriptase for Adult T-Cell Leukemia", Blood, 2013, vol. 121(24), pp. 4894-4901.

Mullen, C.A., et al., "Transfer of the Bacterial Gene for Cytosine Deaminase to Mammalian Cells Confers Lethal Sensitivity to 5-fluorocytosine: A Negative Selection System", Proc. Natl. Acad. Sci. USA, Jan. 1992, vol. 89, pp. 33-37.

Myhre, M., "Exploiting CD4 T Cells for Adoptive Cell Therapy in Cancer", Department of Cellular Therapy, Oslo University Hospital—The Norwegian Radium Hospital, Oslo, Norway, PIVAC Conference Presentation, Sep. 2017 Poster.

Reulen, S.W.A., et al., "Protein-Liposome Conjugates Using Cysteine-Lipids and Native Chemical Ligation", Bioconjugate Chem., 2007, vol. 18, pp. 590-596.

Sæbøe-Larssen, S., et al., "mRNA-Based Electrotransfection of Human Dendritic Cells and Induction of Cytotoxic T Lymphocyte Responses Against the Telomerase Catalytic Subunit (hTERT)", Journal of Immunological Methods, 2002, vol. 259, pp. 191-203.

Shay, J.W., and Wright, W.E., "Role of Telomeres and Telomerase in Cancer", Semin. Cancer Biol., Dec. 2011, vol. 21(6), pp. 349-353.

Shay, J.W., and Wright, W.E., "Telomeres and Telomerase in Normal and Cancer Stem Cells", FEBS Lett., 2010, vol. 584(17), pp. 3819-3825.

Vogel, B., et al., "Efficient Generation of Human Natural Killer Cell Lines by Viral Transformation", Leukemia, 2014, vol. 28, pp. 192-195.

Wälchli, S., et al., "Tapping CD4 T Cells for Cancer Immunotherapy", Department of Cellular Therapy, Oslo University Hospital—The Norwegian Radium Hospital, Oslo, Norway, AACR Poster 3773, Apr. 2017.

Wälchli, S., et al., "Tapping CD4 T Cells for Cancer Immunotherapy", Department of Cellular Therapy, Oslo University Hospital—The Norwegian Radium Hospital, Oslo, Norway, ESMO Poster 11PD, Nov. 2016.

Wälchli, S., et al., "Tapping CD4 T Cells for Cancer Immunotherapy", Department of Cellular Therapy, Oslo University Hospital—The Norwegian Radium Hospital, Oslo, Norway, MD Anderson, YIW Poster #29, Feb. 2017.

Wälchli, S., et al., "With a Little Help from CD4 T Cells in Adoptive T-Cell Transfer", Department of Cellular Therapy, Oslo University Hospital—The Norwegian Radium Hospital, Oslo, Norway, AACR Poster P93, Apr. 2016.

Wälchli, S., et al., "A Practical Approach to T-Cell Receptor Cloning and Expression", PLoS ONE, Nov. 2011, vol. 6(11), e27930, pp. 1-11.

Wälchli, S., et al., "Invariant Chain as a Vehicle to Load Antigenic Peptides on Human MHC Class I for Cytotoxic T-Cell Activation", Eur. J. Immunol., 2014, vol. 44, pp. 774-784.

Walseng, E., et al., "Soluble T-Cell Receptors Produced in Human Cells for Targeted Delivery", PLoS ONE, 2015, vol. 10(4), e0119559, pp. 1-15.

Walseng, E., et al., "A TCR-Based Chimeric Antigen Receptor", Scientific Reports, 2017, vol. 7, 10713, pp. 1-10.

Wang, Y., et al., "2A Self-Cleaving Peptide-Based Multi-Gene Expression System in the Silkworm Bombyx mori", Scientific Reports, 2015, vol. 5, 16273, pp. 1-10.

Wigler, M., et al., "Transfer of Purified Herpes Virus Thymidine Kinase Gene to Cultured Mouse Cells", Cell, May 1977, vol. 11, pp. 223-232.

Edgar, R.C., "MUSCLE: Multiple Sequence Alignment with High Accuracy and High Throughput", Nucleic Acids Research, 2004, vol. 32(5), pp. 1792-1797.

Gjertsen, M.K., et al., "Cytotoxic CD4+ and CD8+ T Lymphocytes, Generated by Mutant p21-ras (12VAL) Peptide Vaccination of a

(56) References Cited

OTHER PUBLICATIONS

Patient, Recognize 12VAL-Dependent Nested Epitopes Present Within the Vaccine Peptide and Kill Autologous Tumour Cells Carrying this Mutation", Int. J. Cancer, 1997, vol. 72, pp. 784-790.
Sievers, F., et al., "Fast, Scalable Generation of High-Quality Protein Multiple Sequence Alignments using Clustal Omega", Mol. Syst. Biol., Oct. 11, 2011, vol. 7, Article No. 539 pp. 1-6.
Loew, R., et al., "Improved Tet-Responsive Promoters with Minimized Background Expression", BMC Biotechnology, 2010, vol. 10(81), pp. 1-13.
Mensali N., et al., "Antigen-Delivery through Invariant Chain (CD74) Boosts CD8 and CD4 T Cell Immunity", Oncoimmunology, 2019, vol. 8(3), pp. e1558663-1 to e1558663-14.
Rice, P., et al., "EMBOSS: The European Molecular Biology Open Software Suite", Trends Genet., Jun. 2000, vol. 16(6), pp. 276-277.

\* cited by examiner

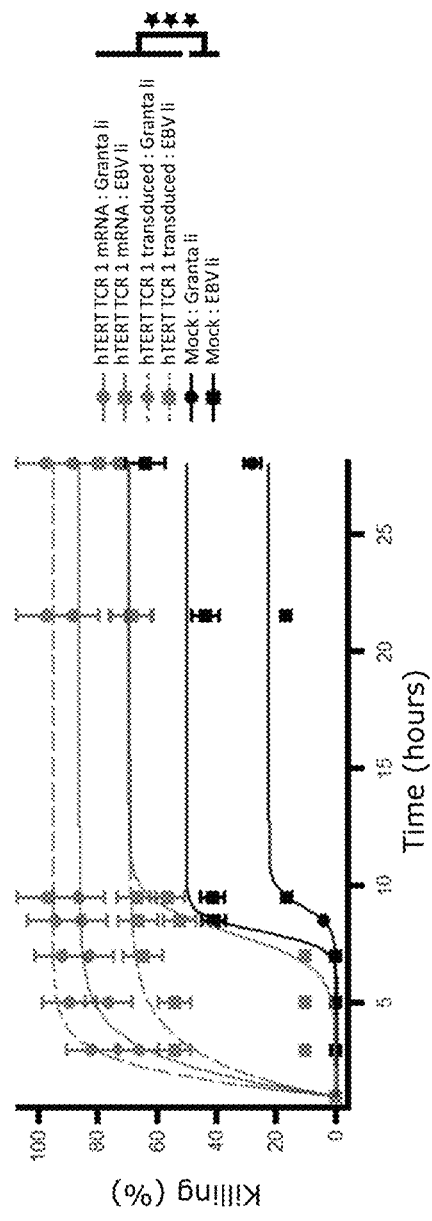
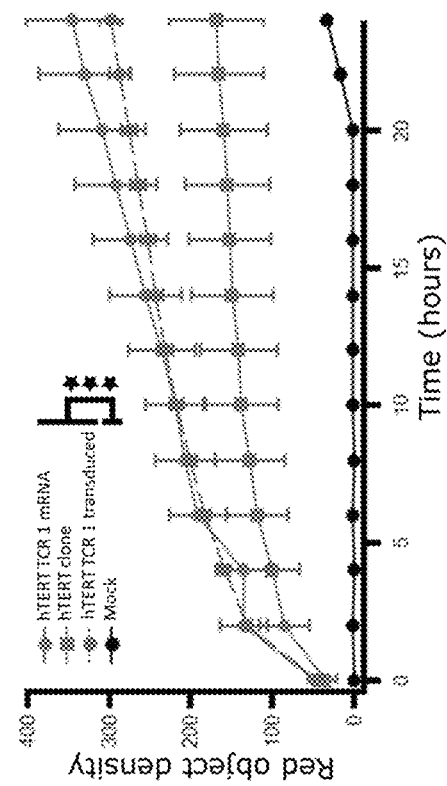
Figure 7A
Figure 7B

SPECIFIC BINDING MOLECULES FOR hTERT

CROSS REFERENCE

This application is a U.S. national stage application under 35 U.S.C. § 371 of International Application No. PCT/EP2019/054798, filed on Feb. 27, 2019, which claims the benefit of GB application serial number 1803178.1, filed Feb. 27, 2018, each of which is incorporated by reference herein in its entirety.

SEQUENCE LISTING

A computer readable form of the Sequence Listing is filed with this application by electronic submission and is incorporated into this application by reference in its entirety. The sequence listing submitted herewith is contained in the file created Sep. 21, 2020, entitled "20-1297-WO-US_SequenceListing_ST25.txt" and 140 kilobytes in size.

The present invention is directed to specific binding molecules which recognise human telomerase reverse transcriptase (hTERT). Provided herein are nucleic acid molecules which encode such specific binding molecules, recombinant constructs and vectors which comprise such nucleic acid molecules, and host cells comprising such nucleic acid molecules, recombinant constructs and vectors. Specific binding molecules which recognise hTERT are also provided herein.

Cancer cells, in contrast to most healthy cells in the human body, have the potential to become immortal and thus to divide indefinitely (i.e. to divide an unlimited number of times). Most healthy cells in the body are only able to divide a limited and defined number of times (this number being known as the Hayflick Limit).

The ability of cancer cells to divide indefinitely is often connected to the expression of the telomerase enzyme. Telomeres are repetitive DNA elements located at the ends of chromosomes (in vertebrates, including humans, the telomere repeating element has the sequence TTAGGG). Due to the mechanism of DNA replication, each time a chromosome is replicated during cell division the end of the chromosome is not replicated, resulting in the loss of a number of telomere repeats and the shortening of the telomere. In most healthy cells, repeated telomere shortening eventually renders further cell division impossible (this generally occurs after 40-60 cell divisions). Once further division is impossible, a cell becomes senescent.

The telomerase enzyme adds additional telomere repeats to the ends of chromosomes, lengthening the telomeres. Telomerase expression thus allows a cell to carry on dividing indefinitely. Telomerase is a ribonucleoprotein, which in humans comprises two subunits of human telomerase reverse transcriptase (hTERT) and two subunits of the telomerase RNA component (TERC). TERC comprises the complementary sequence of the telomere repeating element (i.e. CCCUAA), which is used by hTERT as a template for synthesising additional telomere repeats at the ends of chromosomes. Thus telomerase expression can reverse telomere shortening and may render a cell immortal, i.e. able to continue dividing indefinitely.

The telomerase enzyme is expressed in a significant fraction of all types of cancer cells and therefore constitutes a versatile and attractive target for cancer therapy. Previous and current vaccination trials targeting the telomerase enzyme have shown clinical benefit in patients mounting an immune response against this antigen. However, successful vaccination depends on a functional immune system to launch a response against the antigen. Late stage cancer patients often display impaired immune function, meaning vaccination may lack efficacy. Adoptive cell therapy (ACT) has shown potential to overcome this limitation by infusing patients with T-cells designed to attack the cancer cells. T-cells may be so designed by re-targeting them. T-cell re-targeting can be achieved by modification of a T-cell so that it expresses an exogenous TCR which recognises a particular antigen associated with the disease to be treated. Thus, T-cell receptor (TCR) transfer represents an important strategy to generate cancer-specific T-cells for use in ACT.

The inventors of the present application have identified a TCR which recognises hTERT and may advantageously be utilised in cancer therapy, particularly ACT. The TCR in question is derived from a CD4+ T-cell (i.e. a T-helper cell) isolated from a pancreatic cancer patient vaccinated with the hTERT-derived peptide GV1001 (Kyte, *Expert Opin Investig Drugs* 18(5): 687-694, 2009), which has the sequence set forth in SEQ ID NO: 52, corresponding to amino acids 611-626 of hTERT, as part of a study published in Bernhardt, S. L. et al. (*Br. J. Cancer.* 95(11): 1474-82, 2006). The full amino acid sequence of hTERT is set forth in SEQ ID NO: 51. The pancreatic cancer patient in question survived significantly longer than expected based on the initial prognosis, and than other patients on the same study, demonstrating the therapeutic potential of T-cells expressing this TCR, referred to herein as hTERT-TCR-1. The TCR recognises its hTERT antigen in the context of the Class II HLA molecule HLA-DP4. HLA-DP4 is the most commonly expressed HLA-DP type, with at least one of its two most common sub-types (HLA-DP401 and HLA-DP402) being expressed by 75% of Caucasian individuals, corresponding to about 50% of Europeans, 80% of North Americans and 60% of South Americans and Indians (Castelli et al., *Journal of Immunology* 169(12): 6928-6934, 2002). Approximately 85-90% of human cancers have been found to express telomerase (Shay & Wright, *Semin Cancer Biol* 21(6): 349-353, 2011). Given the large proportion of cancers which express hTERT and the large proportion of the population who express HLA-DP4, use of the TCR disclosed herein is widely applicable in cancer therapy.

A number of TCRs which recognise hTERT have been disclosed, and suggested for use in cancer therapy (see WO 2016/147145, WO 2006/125962 and Miyazaki et al., *Blood* 121: 4894-4901, 2013). However, the previously-disclosed TCRs recognise hTERT-derived peptides in the context of Class I MHC molecules. Among the specific binding molecules disclosed herein are fully human TCRs with specificity for hTERT-derived peptides presented by Class II MHC molecules, in particular with specificity for hTERT-derived peptides presented by HLA-DP4. These TCRs may already have contributed to the clinical effect seen in a patient, i.e. demonstrating efficacy without severe toxicity in a human. Use of such TCRs in therapy may generate a T-helper immune response not seen when using a TCR which recognises a Class I MHC, and may thus provide an enhanced immune response relative to known hTERT-recognising TCRs. Moreover, the presently-disclosed TCR has been found to be particularly amenable for use in therapy: third party CD4+ and CD8+ T-cells were found to be successfully redirected upon expression of the disclosed TCR to recognise antigen-presenting cells loaded with the GV1001 hTERT peptide, demonstrating CD4+ co-receptor independency and high peptide affinity (see examples). Upon target recognition, redirected T-cells were also found to secrete T-helper 1-type cytokines such as TNF-α, IFN-γ and IL-2, which are associated with an efficient anti-tumour immune response, and to display target cell killing.

Accordingly, the TCR disclosed herein may be used in cancer treatment, and nucleic acids encoding the TCR are provided. Other specific binding molecules may also be synthesised based on the binding sequences of the disclosed TCR. For instance targeting moieties in the form of "soluble TCRs" have recently been developed, which lack the transmembrane domains of natural TCRs and may be used to deliver cargos, e.g. drug molecules or suchlike, to target cells (in the present disclosure, target cells are cells which express hTERT). Soluble TCRs are described in Walseng et al. (*PLoS ONE* 10(4): e0119559, 2015). A number of specific binding molecules, and nucleic acid molecules encoding specific binding molecules, based on the binding sequences of the disclosed TCR are provided herein. These include soluble TCRs, and other specific binding molecules as discussed below.

In a first aspect, provided herein is a nucleic acid molecule encoding a variable region of a specific binding molecule directed against hTERT, wherein the variable region is a variable region of an α-chain or a variable region of a β-chain of a T-cell receptor (TCR) molecule capable of binding a peptide comprising the sequence set forth in SEQ ID NO: 1 when the peptide is presented by a Class II Major Histocompatibility Complex (MHC), and wherein:
  (a) the variable region of an α-chain comprises CDR sequences CDR1, CDR2 and CDR3 which respectively comprise (or in a particular embodiment, consist of) the amino acid sequences set forth in SEQ ID NOs: 2, 3 and 4; and
  (b) the variable region of a β-chain comprises CDR sequences CDR1, CDR2 and CDR3 which respectively comprise (or in a particular embodiment, consist of) the sequences set forth in SEQ ID NOs: 5, 6 and 7.

In a particular embodiment, the invention provides a nucleic acid molecule encoding a specific binding molecule capable of binding an hTERT peptide comprising the amino acid sequence set forth in SEQ ID NO: 1 when the peptide is presented by a Class II Major Histocompatibility Complex (MHC), wherein the specific binding molecule comprises a first polypeptide comprising a variable region of an α-chain and a second polypeptide comprising a variable region of a β-chain of a T-cell receptor (TCR), and wherein:
  (a) the variable region of an α-chain comprises CDR sequences CDR1, CDR2 and CDR3 which respectively comprise (or in a particular embodiment, consist of) the amino acid sequences set forth in SEQ ID NOs: 2, 3 and 4; and
  (b) the variable region of a β-chain comprises CDR sequences CDR1, CDR2 and CDR3 which respectively comprise (or in a particular embodiment, consist of) the sequences set forth in SEQ ID NOs: 5, 6 and 7.

In another aspect, provided herein is a nucleic acid molecule encoding a variable region of a specific binding molecule directed against hTERT, wherein the variable region is a variable region of an α-chain or a variable region of a β-chain of a T-cell receptor (TCR) molecule capable of binding a peptide comprising the sequence set forth in SEQ ID NO: 1 when the peptide is presented by a Class II Major Histocompatibility Complex (MHC), and wherein:
  (a) the variable region of an α-chain comprises CDR sequences CDR1, CDR2 and CDR3 which respectively comprise (or in a particular embodiment, consist of) the amino acid sequences set forth in SEQ ID NOs: 2, 3 and 4, or amino acid sequences having 1, 2 or 3 modifications (e.g. amino acid substitutions, in particular conservative substitutions of amino acid residues) relative to SEQ ID NOs: 2, 3 and 4; and
  (b) the variable region of a β-chain comprises CDR sequences CDR1, CDR2 and CDR3 which respectively comprise (or in a particular embodiment, consist of) the sequences set forth in SEQ ID NOs: 5, 6 and 7, or amino acid sequences having 1, 2 or 3 modifications (e.g. amino acid substitutions, in particular conservative substitutions of amino acid residues) relative to SEQ ID NOs: 5, 6 and 7.

In another aspect, provided herein is a recombinant construct comprising a nucleic acid molecule as defined above linked to a heterologous nucleic acid sequence, optionally wherein the heterologous nucleic acid sequence is an expression control sequence.

In another aspect, provided herein is a vector comprising a nucleic acid molecule as defined above or a recombinant construct as defined above.

In another aspect, provided herein is a host cell comprising a nucleic acid molecule as defined above, a recombinant construct as defined above or a vector as defined above, wherein the specific binding molecule is heterologous to the cell.

In another aspect, provided herein is a specific binding molecule capable of binding a peptide comprising the sequence set forth in SEQ ID NO: 1 when the peptide is presented by a Class II Major Histocompatibility Complex (MHC), said specific binding molecule comprising:
  (i) a first polypeptide comprising a variable region of an α-chain of a TCR comprising CDR sequences CDR1, CDR2 and CDR3 which respectively comprise (or in a particular embodiment, consist of) the amino acid sequences set forth in SEQ ID NOs: 2, 3 and 4; and
  (ii) a second polypeptide comprising a variable region of a β-chain of a TCR comprising CDR sequences CDR1, CDR2 and CDR3 which respectively comprise (or in a particular embodiment, consist of) the sequences set forth in SEQ ID NOs: 5, 6 and 7.

In another aspect, provided herein is a composition comprising:
  (i) a host cell as defined above, wherein the host cell is an immune effector cell and the nucleic acid molecule, construct or vector encodes a specific binding molecule which, when expressed by the immune effector cell, is located on the surface of the cell; or
  (ii) a specific binding molecule as defined above;
and at least one physiologically-acceptable diluent, carrier or excipient.

In another aspect, provided herein is a method of generating a host cell as defined above, comprising introducing a nucleic acid molecule as defined above, a recombinant construct as defined above or a vector as defined above into a cell which does not encode a specific binding molecule comprising a variable region of an α-chain as defined above or a variable region of a β-chain as defined above.

In another aspect, provided herein is a host cell as defined above, wherein the host cell is an immune effector cell and the nucleic acid molecule, construct or vector encodes a specific binding molecule which, when expressed by the immune effector cell, is located on the surface of the cell; a specific binding molecule as defined above; or a composition as defined above, for use in therapy.

In another aspect, provided herein is a host cell as defined above, wherein the host cell is an immune effector cell and the nucleic acid molecule, construct or vector encodes a specific binding molecule which, when expressed by the immune effector cell, is located on the surface of the cell; a specific binding molecule as defined above; or a composition as defined above, for use in the treatment of cancer.

In a related aspect, provided herein is a method of treatment comprising administering to a subject a host cell as defined above, wherein the host cell is an immune effector cell and the nucleic acid molecule, construct or vector encodes a specific binding molecule which, when expressed by the immune effector cell, is located on the surface of the cell; a specific binding molecule as defined above; or a composition as defined above.

In another related aspect, provided herein is the use of a host cell as defined above, wherein the host cell is an immune effector cell and the nucleic acid molecule, construct or vector encodes a specific binding molecule which, when expressed by the immune effector cell, is located on the surface of the cell; or a specific binding molecule as defined above, in the manufacture of a medicament for use in the treatment of cancer.

In another aspect, the invention provides a kit comprising a first vector and a second vector as defined above, the first vector comprising a nucleic acid molecule encoding a first polypeptide comprising a variable region of an α-chain as defined above and the second vector encoding a second polypeptide comprising the variable region of a β-chain as defined above.

T-cells are lymphocytes which form an essential part of the adaptive immune system of vertebrates, and play a central role in cell-mediated immunity. T-cells can be distinguished from other lymphocytes, such as B-cells and natural killer (NK) cells, by the presence of T-cell receptors (TCRs) in their cell membrane. A variety of different T-cell sub-types exist, including T-helper cells, cytotoxic T-cells, memory T-cells etc.

TCRs are protein complexes expressed by T-cells, which, when expressed, are anchored to the cell membrane and thus located on the surface of T-cells. Most TCRs are heterodimers which comprise an α- and a β-chain, both of which consist of a variable region and a constant region. The variable region is located at the N-terminal part of the chain, and is wholly extracellular; the constant region is located at the C-terminal part of the chain, and comprises an extracellular domain, a transmembrane domain and a short cytoplasmic domain. TCR chains are encoded and synthesised in an immature form, with an N-terminal signal (or leader) sequence. This sequence is located N-terminal to the variable region of an α- or β-TCR chain when it is synthesised. The signal sequence is cleaved from the TCR chain upon insertion of the chain into the cell membrane, and so the leader sequences are not present in the chains of a mature TCR located at the cell surface.

The variable regions of the α- and β-chains of a TCR may form a structure able to specifically bind a target antigen. TCR antigens are proteins, and the specific part of an antigen bound by the TCR is known as the T-cell epitope. T-cell epitopes are short antigen fragments, generally peptides between 8 and 25 amino acids in length. The relevant antigen fragment is presented to the TCR by a Major Histocompatibility Complex (MHC). Upon binding the antigen, the TCR may activate a signal transduction pathway which activates the T-cell to initiate an immune response.

The variable region of an α- or β-chain comprises three hypervariable, complementarity-determining regions (CDRs), known as CDR1, CDR2 and CDR3. CDR1 is the most N-terminal of the CDRs, CDR3 the most C-terminal and CDR2 is located between CDR1 and CDR3. It is the CDRs which directly interact with a target epitope/MHC complex, and thus determine the specificity of a TCR, with CDR3 being the most important CDR in determining TCR specificity. The sections of the variable regions of TCR chains which do not form the CDRs are known as framework regions. A TCR variable region contains four such framework regions. Framework region 1 (FR1) is N-terminal to CDR1; framework region 2 (FR2) links CDR1 and CDR2; framework region 3 (FR3) links CDR2 and CDR3; framework region 4 (FR4) links CDR3 to the constant region of the TCR chain. The sequences of the framework regions do vary between TCR molecules, but the framework region sequences are much less variable than those of the CDRs. The framework regions form a scaffold for the CDRs, such that their spatial arrangement is appropriate for target binding. The sequence of the framework regions is thus important for TCR function, as they determine the overall structure of the variable region of a TCR chain. This structure must hold the CDRs in the correct orientations and relative positions for them to bind the target antigen. However, as noted above it is the CDR sequences which determine a TCR's specificity (i.e. the target to which the TCR binds).

As noted above, a TCR may recognise an epitope/MHC complex. There are two classes of MHCs: Class I and Class II. Class I MHCs are expressed by all nucleated cells; Class II MHCs are expressed only by professional antigen-presenting cells (APCs), such as dendritic cells. The function of all MHCs is to present short peptide segments for recognition by T-cells. A Class I MHC presents peptide fragments from within the cell on which it is expressed, and is generally recognised by a $CD8^+$ T-cell (cytotoxic T-cell). If a $CD8^+$ T-cell recognises a peptide presented by a Class I MHC as an antigen, the T-cell triggers apoptosis of the cell on which that Class I MHC is expressed. A Class II MHC generally presents peptide fragments from proteins which have been endocytosed by the APC on which it is expressed, and is generally recognised by a $CD4^+$ T-cell (helper T-cell). If a naïve $CD4^+$ T-cell recognises a peptide presented by a Class II MHC as an antigen, it will proliferate. Its daughter cells will differentiate into effector, memory and regulatory T-cells, which together mediate an immune response by other components of the immune system.

In humans, MHC complexes comprise human leukocyte antigens (HLAs). Every human has 3 main Class I MHC HLA genes (HLA-A, HLA-B and HLA-C) and 6 main Class II MHC HLA genes (HLA-DPA1, HLA-DPB1, HLA-DQA1, HLA-DQB1, HLA-DRA, and HLA-DRB1). When a TCR binds an MHC-antigen complex, both the antigen and MHC proteins are contacted by the TCR, meaning that TCRs recognise specific MHC-antigen complexes, rather than simply an antigen. This interaction of a TCR with the MHC is believed to be via CDR2, and means that TCRs recognise antigens only when they are complexed with a specific HLA protein, a feature known as MHC restriction. HLA genes are highly polymorphic, meaning that different individuals tend to carry different HLA alleles, and that a specific TCR would not be functional in all individuals (only in those carrying the appropriate HLA allele to which the TCR is restricted).

Class II MHCs are heterodimers comprising two homogenous peptides, the α-chain and the β-chain. In each Class II MHC the α-chain is encoded by the 'A' gene and the β-chain by the 'B' gene, hence in an HLA-DP Class II MHC the α-chain is encoded by the HLA-DPA1 gene and the β-chain by the HLA-DPB1 gene. As noted above, the TCR disclosed herein recognises its hTERT epitope in the context of HLA-DP4. HLA-DP4 is an HLA-DPA1 and HLA-DPB1 allele. As noted above, the two most common HLA-DP4

Class II MHC molecules are HLA-DP401 and HLA-DP402. The HLA-DP401 molecule comprises the α-chain HLA-DPA1*0103 and the β-chain HLA-DPB1*0401. The HLA-DP402 molecule comprises the α-chain HLA-DPA1*0103 and the β-chain HLA-DPB1*0402. Thus the only difference is in the β-chain allele; HLA-DPB1*0401 and HLA-DPB1*0402 differ from each other by only 3 amino acid residues.

As discussed above, the nucleic acid molecules and specific binding molecules provided herein are based on a TCR molecule isolated from a cancer patient who received a vaccination against hTERT and is now in remission. As detailed, the patient was vaccinated with the peptide GV1001, which has the sequence set forth in SEQ ID NO: 52. It was found that the minimal epitope recognised by the isolated TCR is the sequence set forth in SEQ ID NO: 1. The amino acid sequence of SEQ ID NO: 1 corresponds to hTERT amino acids 615-626 (i.e. amino acids 5-16 of SEQ ID NO: 52). As noted above, the isolated TCR recognises its target epitopes in the context of HLA-DP4, i.e. when the target epitopes are presented by an HLA-DP4 Class II MHC.

The hTERT-TCR-1 is an αβ TCR (i.e. it is a heterodimer comprising an α-chain and a β-chain). The α-chain of hTERT-TCR-1 comprises a variable region in which CDR1 (which may be referred to as VαCDR1) consists of the amino acid sequence set forth in SEQ ID NO: 2, CDR2 (which may be referred to as VαCDR2) consists of the amino acid sequence set forth in SEQ ID NO: 3 and CDR3 (which may be referred to as VαCDR3) consists of the amino acid sequence set forth in SEQ ID NO: 4. The β-chain of hTERT-TCR-1 comprises a variable region in which CDR1 (which may be referred to as VβCDR1) consists of the amino acid sequence set forth in SEQ ID NO: 5, CDR2 (which may be referred to as VβCDR2) consists of the amino acid sequence set forth in SEQ ID NO: 6 and CDR3 (which may be referred to as VβCDR3) consists of the amino acid sequence set forth in SEQ ID NO: 7.

The nucleic acid molecule provided herein encodes a variable region of a specific binding molecule directed against hTERT, i.e. a specific binding molecule which recognises an hTERT epitope. A "specific binding molecule" as defined herein is a molecule which binds specifically to a particular molecular partner. Preferably, the specific binding molecule binds its partner under physiological conditions, i.e. the conditions that would be found within the body of a host animal, in particular the body of a human. In particular, the specific binding molecule may bind its partner in the conditions found within a human tumour. Physiological conditions may for instance be a temperature e.g. in the range 35-39° C. and a pH of 6-8. The molecular partner bound by the specific binding molecule defined herein is a peptide-Class II MHC complex, in which the peptide presented by the Class II MHC is a fragment of the hTERT protein (i.e. a fragment of SEQ ID NO: 51).

The nucleic acid molecule provided herein encodes a variable region of an α-chain and/or a variable region of a β-chain of a TCR molecule capable of binding a peptide comprising the sequence set forth in SEQ ID NO: 1 when the peptide is presented by a Class II MHC. Such a variable region of an α-chain preferably comprises CDR sequences VαCDR1, VαCDR2 and VαCDR3 which respectively comprise, or have (i.e. consist of), the amino acid sequences set forth in SEQ ID NOs: 2, 3 and 4; such a variable region of a β-chain preferably comprises CDR sequences VβCDR1, VβCDR2 and VβCDR3 which respectively comprise, or have (i.e. consist of), the sequences set forth in SEQ ID NOs: 5, 6 and 7.

As noted above, in certain aspects one or more of, or each of, the VαCDRs may alternatively be modified relative to the amino acid sequences set forth in SEQ ID NOs: 2, 3 and 4, i.e. VαCDR1 may comprise or consist of an amino acid sequence which is a modified version of SEQ ID NO: 2, VαCDR2 may comprise or consist of an amino acid sequence which is a modified version of SEQ ID NO: 3 and/or VαCDR3 may comprise or consist of an amino acid sequence which is a modified version of SEQ ID NO: 4. Similarly, the VβCDRs may be modified relative to the amino acid sequences set forth in SEQ ID NOs: 5, 6 and 7, i.e. VβCDR1 may comprise or consist of an amino acid sequence which is a modified version of SEQ ID NO: 5, VβCDR2 may comprise or consist of an amino acid sequence which is a modified version of SEQ ID NO: 6 and/or VβCDR3 may comprise or consist of an amino acid sequence which is a modified version of SEQ ID NO: 7.

A modified version of SEQ ID NO: 2, 3, 4, 5, 6 or 7, as defined herein comprises one, two or three modifications relative to SEQ ID NO: 2, 3, 4, 5, 6 or 7, respectively. Preferably a modified version of SEQ ID NO: 2, 3, 4, 5, 6 or 7 comprises one or two modifications relative to SEQ ID NO: 2, 3, 4, 5, 6 or 7, respectively, most preferably only a single modification. In a particular embodiment VαCDR1 comprises or consists of a modified version of SEQ ID NO: 2; in another embodiment VαCDR2 comprises or consists of a modified version of SEQ ID NO: 3; in another embodiment VαCDR3 comprises or consists of a modified version of SEQ ID NO: 4; in another embodiment VβCDR1 comprises or consists of a modified version of SEQ ID NO: 5; in another embodiment VβCDR2 comprises or consists of a modified version of SEQ ID NO: 6; in another embodiment VβCDR3 comprises or consists of a modified version of SEQ ID NO: 7.

By modification in this context is meant a substitution, addition or deletion of an amino acid residue. Preferably the modification is an amino acid substitution. When a CDR sequence is modified by substitution of a particular amino acid residue, the substitution may be a conservative amino acid substitution. The term "conservative amino acid substitution", as used herein, refers to an amino acid substitution in which one amino acid residue is replaced with another amino acid residue having a similar side chain. Amino acids with similar side chains tend to have similar properties, and thus a conservative substitution of an amino acid important for the structure or function of a polypeptide may be expected to affect polypeptide structure/function less than a non-conservative amino acid substitution at the same position. Families of amino acid residues having similar side chains have been defined in the art, including basic side chains (e.g. lysine, arginine, histidine), acidic side chains (e.g. aspartic acid, glutamic acid), uncharged polar side chains (e.g. asparagine, glutamine, serine, threonine, tyrosine), non-polar side chains (e.g. glycine, cysteine, alanine, valine, leucine, isoleucine, proline, phenylalanine, methionine, tryptophan) and aromatic side chains (e.g. tyrosine, phenylalanine, tryptophan, histidine). Thus a conservative amino acid substitution may be considered to be a substitution in which a particular amino acid residue is substituted for a different amino acid residue in the same family. However, a substitution of an amino acid residue in the CDR sequence may also be a non-conservative substitution, in which one amino acid residue is substituted for another with a side-chain belonging to a different family.

The variable region of a TCR chain encoded by the nucleic acid molecule may be encoded in the context of a longer polypeptide chain. For instance, the variable region may be encoded with a C-terminal constant region, e.g. in the context of a TCR chain or a specific binding molecule as described below.

The variable region of a TCR chain encoded by the nucleic acid molecule provided herein may be the variable region of an α- or β-chain of a TCR molecule capable of binding a peptide comprising the sequence set forth in SEQ ID NO: 1 when the peptide is presented by an HLA-DP4 Class II MHC.

In a preferred embodiment, the nucleic acid molecule provided herein encodes a specific binding molecule capable of binding a peptide comprising the sequence set forth in SEQ ID NO: 1 when the peptide is presented by a Class II MHC, in particular an HLA-DP4 Class II MHC. The specific binding molecule comprises a variable region of an α-chain as defined above (i.e. comprising CDR sequences VαCDR1, VαCDR2 and VαCDR3 which respectively comprise or consist of the amino acid sequences set forth in SEQ ID NOs: 2, 3 and 4) and a variable region of a β-chain as defined above (i.e. comprising CDR sequences VβCDR1, VβCDR2 and VβCDR3 which respectively comprise or consist of the sequences set forth in SEQ ID NOs: 5, 6 and 7).

As noted above the variable regions of TCR chains comprise framework regions which separate the CDR sequences. Thus the variable region of an α-chain comprises framework regions VαFR1 to VαFR4 which separate the CDRs and are distributed as detailed above, and the variable region of a β-chain comprises VβFR1 to VβFR4 which separate the CDRs and are distributed as detailed above. Thus VαFR1 is located at the N-terminus of the variable region of an α-chain, N-terminal of VαCDR1; VαFR2 is located between VαCDR1 and VαCDR2; VαFR3 is located between VαCDR2 and VαCDR3; and VαFR4 is located C-terminal to VαCDR3. Correspondingly, VβFR1 is located at the N-terminus of the variable region of a β-chain, N-terminal of VβCDR1; VβFR2 is located between VβCDR1 and VβCDR2; VβFR3 is located between VβCDR2 and VβCDR3; and VβFR4 is located C-terminal to VβCDR3.

The encoded specific binding molecule may comprise a first polypeptide comprising the variable region of an α-chain and a second polypeptide comprising the variable region of a β-chain. In the specific binding molecule, the first and second polypeptide are associated, that is to say the first and second polypeptide form a complex. The variable region of an α-chain of the first polypeptide and the variable region of a β-chain of the second polypeptide together form an antigen-binding site, located at the interface between the variable region of an α-chain and the variable region of a β-chain and comprising the CDR sequences.

The first polypeptide and second polypeptide may be covalently linked within the encoded specific binding molecule. For instance, the first polypeptide and second polypeptide may be located within a single polypeptide chain (i.e. a linear chain of amino acids joined by peptide bonds). In this case, the first polypeptide may be encoded N-terminal to the second polypeptide or the second polypeptide may be encoded N-terminal to the first polypeptide. The first and second polypeptide may be separated by a linker, or may be directly joined to one another. By "directly joined" is meant that the C-terminal amino acid of the first polypeptide and the N-terminal amino acid of the second polypeptide (or vice-versa) are neighbouring within the primary structure (i.e. amino acid sequence) of the polypeptide chain.

Alternatively, the first polypeptide and second polypeptide may constitute separate polypeptide chains which are covalently joined. In this embodiment, any covalent bond may join the first polypeptide chain and the second polypeptide chain, e.g. the chains may be joined by one or more disulphide bonds formed between cysteine residues and/or by one or more isopeptide bonds formed between a side chain amine group and a side chain carboxyl group.

In another embodiment, the first polypeptide and the second polypeptide associate by non-covalent interactions, e.g. by one or more hydrogen bonds and/or one or more ionic bonds. The first and second polypeptides may associate via one or more salt bridges (a salt bridge is formed between charged amino acid groups and comprises both hydrogen bonding and ionic bonding) or by hydrophobic interactions. Any form of interactions may mediate the association between the first and second polypeptide.

Even if the first and second polypeptide constitute separate polypeptide chains within the specific binding molecule, the specific binding molecule may nonetheless be encoded as a single polypeptide chain. As discussed below, the first and second polypeptide may be encoded as a single chain in which a cleavable linker separates the two polypeptides. Cleavage of the linker leads to peptide separation, and allows the mature specific binding molecule to be formed from the separate polypeptide chains.

The variable region of an α-chain may correspond to the variable region of the α-chain of hTERT-TCR-1, or a variant thereof. The variable region of the α-chain of hTERT-TCR-1 has the sequence set forth in SEQ ID NO: 9. Thus the specific binding molecule may comprise a variable region of an α-chain comprising or consisting of the amino acid sequence set forth in SEQ ID NO: 9, or a variant thereof. According to the present disclosure a "variant" sequence is a sequence derived from a specified sequence (e.g. a natural sequence) and which is modified relative to the specified sequence. A variant, as defined herein, may be modified relative to the sequence from which it is derived by substitution, addition or deletion of one or more amino acids (or in the case of nucleic acid sequences, nucleotides). A variant of SEQ ID NO: 9 is an amino acid sequence having at least 95% 96%, 97%, 98% or 99% sequence identity to SEQ ID NO: 9, with the proviso that the CDR sequences are as defined above.

The variable region of a β-chain may correspond to the variable region of the β-chain of hTERT-TCR-1, or may be a variant thereof. The variable region of the β-chain of hTERT-TCR-1 has the sequence set forth in SEQ ID NO: 11. Thus the specific binding molecule may comprise a variable region of a β-chain comprising or consisting of the amino acid sequence set forth in SEQ ID NO: 11, or a variant thereof. A variant of SEQ ID NO: 11 is an amino acid sequence having at least 95%, 96%, 97%, 98% or 99% sequence identity to SEQ ID NO: 11, with the proviso that the CDR sequences are as defined above.

In a particular embodiment, the nucleic acid molecule encodes a specific binding molecule comprising a first polypeptide which comprises a variable region of an α-chain comprising or consisting of the amino acid sequence set forth in SEQ ID NO: 9 or an amino acid sequence having at least 95% sequence identity thereto, and a second polypeptide which comprises a variable region of a β-chain comprising or consisting of the amino acid sequence set forth in SEQ ID NO: 11 or an amino acid sequence having at least 95% sequence identity thereto.

In another particular embodiment, the nucleic acid molecule encodes a specific binding molecule comprising a first polypeptide which comprises a variable region of an α-chain comprising or consisting of the amino acid sequence set forth in SEQ ID NO: 8 or an amino acid sequence having at least 95% sequence identity thereto, and a second polypeptide which comprises a variable region of a β-chain comprising or consisting of the amino acid sequence set forth in SEQ ID NO: 10 or an amino acid sequence having at least 95% sequence identity thereto.

In a particular embodiment, the specific binding molecule comprises a first polypeptide comprising a variable region of an α-chain comprising or consisting of the amino acid sequence set forth in SEQ ID NO: 8 or an amino acid sequence having at least 95% sequence identity thereto, and a second polypeptide comprising a variable region of a β-chain comprising or consisting of the amino acid sequence set forth in SEQ ID NO: 10 or an amino acid sequence having at least 95% sequence identity thereto.

Thus as can be seen it is preferred that the nucleic acid molecule disclosed herein comprises a full-length variable region of an α-chain paired with a full-length variable region of a β-chain.

When the nucleic acid molecule disclosed herein encodes a first polypeptide (which comprises the variable region of an α-chain) and a second polypeptide (which comprises the variable region of a β-chain), as detailed above, the first polypeptide and the second polypeptide may be separately encoded. That is to say, the nucleic acid molecule may comprise a first gene which encodes the first polypeptide and a second gene which encodes the second polypeptide. When the first and second polypeptide are encoded separately, each are transcribed separately into separate mRNA molecules, and translated separately to yield discrete polypeptide chains.

However, it is preferred that the specific binding molecule is encoded as a single amino acid chain in which the first polypeptide and the second polypeptide are linked (i.e. as a single amino acid chain comprising both the first polypeptide and the second polypeptide). Such a chain is encoded by a single gene which is transcribed into a single mRNA which encodes both the first and the second polypeptide. In the single chain the first polypeptide may be located N-terminal to the second polypeptide, or the second polypeptide may be located N-terminal to the first polypeptide.

As noted above, even if the first and second polypeptides are encoded as a single chain, they may nonetheless be separated prior to formation of the specific binding molecule. In this scenario, by encoding the first polypeptide and the second polypeptide as single chain it is possible to ensure that when the specific binding molecule is expressed from the provided nucleic acid molecule, equal amounts of the first and second polypeptides are produced. Encoding the first and second polypeptide as a single chain also ensures that the first polypeptide and second polypeptide are synthesised in close proximity to one another, increasing the chances of the two polypeptides forming a functional complex with each other. Thus encoding the first and second polypeptides as a single chain is advantageous.

In a particular embodiment, the first and the second polypeptides are encoded as a single chain in which they are joined by a linker. The term "linker", as used herein, refers to an amino acid sequence which is located between the first and second polypeptides within a single polypeptide chain, joining the first polypeptide to the second polypeptide. The linker plays no functional role in the specific binding molecule, i.e. the linker does not play a role in antigen binding or signal transduction, it has no effector function and is not required for the structural integrity of the specific binding molecule. The specific binding molecule may be encoded as a single chain which comprises, in the following order from N-terminus to C-terminus: (i) the first polypeptide; (ii) the linker; and (iii) the second polypeptide. Alternatively, the specific binding molecule may be encoded as a single chain which comprises, in the following order from N-terminus to C-terminus: (i) the second polypeptide; (ii) the linker; and (iii) the first polypeptide.

The linker may have any suitable amino acid sequence. Suitable linkers are known in the art. The linker may be of any suitable length, e.g. it may be 1-30 amino acids long, or more preferably 1-25 or 1-20 amino acids long. The linker may be cleavable, allowing separation of the first and second polypeptides. If the first and second polypeptides cannot be separated, the two chains may not be able to adopt the correct conformations required for formation of the antigen-binding site from the variable regions of the α- and β-chains. The skilled person is able to select an appropriate linker. The linker may comprise a protease cleavage site to allow specific, post-translational cleavage of the linker and thus separation of the first and second polypeptides. Appropriate protease cleavage sites are well-known to the skilled person and include thrombin, factor Xa, enterokinase, human rhinovirus (HRV) 3C and tobacco etch virus (TEV) cleavage sites.

In a preferred embodiment, the linker is self-splicing. A self-splicing linker is able to catalyse its own cleavage, thus separating the first and second polypeptides without the requirement of an active cleavage step. No stimulation or induction is required for the self-splicing reaction to occur. The cleavage reaction may completely excise the linker from the single chain specific binding molecule; alternatively the linker, or a part of the linker, may remain attached to one or both of the resultant separate polypeptide chains. The self-splicing reaction catalysed by the linker may occur post-translationally (i.e. it may be an autocatalytic proteolysis reaction), or it may occur co-translationally. Co-translational splicing can occur by preventing the formation of a peptide bond within the linker or between the linker and one of the polypeptide chains on either side of it.

A preferred self-splicing linker is one derived from a picornavirus self-cleaving 2A peptide. 2A peptides are approximately 20-25 amino acids long and end with the conserved sequence motif Asp-Val/Ile-Glu-X-Asn-Pro-Gly-Pro (SEQ ID NO: 53). 2A peptides undergo co-translational self-splicing, by preventing the formation of a peptide bond between the conserved glycine reside in the penultimate position within the linker and the C-terminal proline residue, resulting effectively in cleavage of the protein between these two amino acids. After cleavage, the 2A peptide (with the exception of the C-terminal proline) remains attached to the C-terminus of the upstream protein; the final proline residue remains attached to the N-terminus of the downstream protein. 2A peptides are described in Lewis et al., 2015 (*J Neurosci Methods* 256: 22-29).

A particularly preferred sequence of a 2A peptide-derived linker is presented in SEQ ID NO: 18, and thus the self-splicing linker may be a 2A peptide comprising or consisting of the amino acid sequence set forth in SEQ ID NO: 18. However, the sequence of the peptide upstream of the conserved C-terminal 2A sequence motif (SEQ ID NO: 53) may be varied without significant loss of self-splicing activity, and thus the linker may be a functional variant of SEQ ID NO: 18 (i.e. a sequence variant of SEQ ID NO: 18 which retains self-splicing activity) comprising or consisting of an amino acid sequence with at least 50%, 55%, 60%, 65%, 70%, 75%, 80%, 85%, 90% or 95% sequence identity to that of SEQ ID NO: 18, with the proviso that the linker ends with the above-described conserved sequence motif (i.e. the sequence motif of SEQ ID NO: 53). In particular, functional self-splicing variants of SEQ ID NO: 18 may demonstrate at least 70%, 75%, 80%, 85%, 90%, 95%, 100%, 105% or 110% of the self-splicing activity of the peptide of SEQ ID NO: 18. A number of functional 2A sequences are disclosed in Wang et al., 2015 (*Scientific Reports* 5: Article No. 16273), as are certain modifications which may be made to native 2A sequences to enhance their self-splicing activity.

As detailed above, the nucleic acid molecule disclosed herein preferably encodes a specific binding molecule comprising a first polypeptide which comprises a variable region of an α-chain and a second polypeptide which comprises a variable region of a β-chain.

Preferably, the first polypeptide further comprises a constant region of an α-chain and the second polypeptide further comprises a constant region of a β-chain. In the first polypeptide, the constant region of an α-chain is C-terminal to the variable region of an α-chain; in the second polypeptide the constant region of a β-chain is C-terminal to the variable region of a β-chain. Preferably in each chain the constant region is immediately C-terminal to the variable region, i.e. the C-terminal amino acid of the variable region is joined by a peptide bond to the N-terminal amino acid of the constant region, and no linker is present between the variable region and the constant region.

As discussed above, TCR chains natively comprise an N-terminal variable region and a C-terminal constant region. A full-length constant region comprises an N-terminal extracellular domain, a transmembrane domain and a C-terminal intracellular domain. The constant region is the same (i.e. constant) in all TCR chains of the same isotype in any given species, e.g. each human TCR α-chain has the same constant region. The human TCR α-chain constant region has the amino acid sequence set forth in SEQ ID NO: 12. In SEQ ID NO: 12, amino acids 1-117 constitute the extracellular domain, amino acids 118-137 constitute the transmembrane domain and amino acids 138-142 constitute the intracellular domain. There are two human β-chain subtypes, defined by the sequence of their constant region: subtype 1 and subtype 2. The hTERT-TCR-1 β-chain is of subtype 2. The human β-chain subtype 2 constant region has the amino acid sequence set forth in SEQ ID NO: 13. In SEQ ID NO: 13, amino acids 1-145 constitute the extracellular domain, amino acids 146-168 constitute the transmembrane domain and amino acids 169-179 constitute the intracellular domain.

The first polypeptide may comprise a full-length constant region of an α-chain or a truncated constant region of an α-chain. A truncated constant region of an α-chain may in particular be truncated at its C-terminus. For instance, the constant region of an α-chain may be truncated such that it does not contain a transmembrane domain. Truncation of the constant region of an α-chain such that it does not comprise a transmembrane domain renders the constant region of an α-chain soluble.

Similarly, the second polypeptide may comprise a full-length constant region of a β-chain or a truncated constant region of a β-chain. A truncated constant region of a β-chain may in particular be truncated at its C-terminus. For instance, the constant region of a β-chain may be truncated such that it does not contain a transmembrane domain. Truncation of the constant region of a β-chain such that it does not comprise a transmembrane domain renders the constant region of a β-chain soluble.

In a particular embodiment, the specific binding molecule comprises a first polypeptide comprising a full-length constant region of an α-chain and a second polypeptide comprising a full-length constant region of a β-chain, i.e. full-length constant regions may be paired. In another embodiment, the specific binding molecule comprises a first polypeptide comprising a truncated constant region of an α-chain and a second polypeptide comprising a truncated constant region of a β-chain, i.e. truncated constant regions may be paired. However, a full-length constant region may nonetheless be paired with a truncated constant region, i.e. a full-length constant region of an α-chain may be paired with a truncated constant region of a β-chain, or a truncated constant region of an α-chain may be paired with a full-length constant region of a β-chain.

In a particular embodiment of the disclosure, the nucleic acid molecule provided encodes a TCR molecule which, when expressed by an immune effector cell, is located on the surface of the cell. That is to say, when the TCR molecule is expressed by an immune cell such as a T-cell, the TCR molecule localises to the plasma membrane of the cell. The TCR molecule has the structure of a natural αβ TCR molecule, i.e. it comprises an α-chain (corresponding to the first polypeptide) and a β-chain (corresponding to the second polypeptide). The constant regions of the α- and β-chains are both full-length, meaning they each comprise a transmembrane domain. The transmembrane domains of the constant regions of the α- and β-chains anchor the TCR to the cell membrane. When expressed in an immune effector cell, the TCR is functional and upon target recognition activates the immune cell effector functionality via the signalling pathways known in the art.

By "immune effector cell", as referred to herein, is meant any immune cell which is able to perform effector functions when activated (e.g. cytotoxic target cell killing, cytokine release, etc.), and which is able to express a functional TCR. By "functional TCR" is meant a TCR which is able to initiate immune effector functions upon target recognition. Immune effector cells are discussed further below, but as can be seen the term "immune effector cell" as used herein essentially means a cell which can express a TCR and the associated signalling transduction proteins (and optionally co-receptors), such that when expressed the TCR is located on the surface of the cell and, upon target recognition, is able to activate the cell to perform its effector functions. Accordingly the term "immune effector cell" as used herein does not incorporate all cells of the immune system, but rather only those that have the above characteristics.

As noted above, the TCR molecule which, when expressed by an immune effector cell, is located on the surface of the cell, comprises a first polypeptide which is a TCR α-chain and a second polypeptide which is a TCR β-chain. In an embodiment, the constant region of the α-chain comprises or consists of the amino acid sequence set forth in SEQ ID NO: 12, or a variant of SEQ ID NO: 12. A variant of SEQ ID NO: 12 is an amino acid sequence with at least 95%, 96%, 97%, 98% or 99% sequence identity to SEQ ID NO: 12. In this embodiment the constant region of the β-chain comprises or consists of the amino acid sequence set forth in SEQ ID NO: 13, or a variant of SEQ ID NO: 13. A variant of SEQ ID NO: 13 is an amino acid sequence with at least 95%, 96%, 97%, 98% or 99% sequence identity to SEQ ID NO: 13.

Thus in a particular embodiment of the disclosure, provided herein is a nucleic acid molecule which encodes a TCR molecule which, when expressed by an immune effector cell, is located on the surface of the cell, and wherein the first polypeptide is an α-chain comprising a constant region which comprises the amino acid sequence set forth in SEQ ID NO: 12, or an amino acid sequence having at least 95% sequence identity thereto; and the second polypeptide is a β-chain comprising a constant region which comprises the amino acid sequence set forth in SEQ ID NO: 13, or an amino acid sequence having at least 95% sequence identity thereto.

As described above, TCR chains are encoded and synthesised in an immature form comprising an N-terminal leader sequence. An N-terminal leader sequence is located at the N-terminus of a TCR chain and is generally about 20-25 amino acids long, though may be longer or shorter than this. The leader sequence is cleaved upon insertion of the TCR chain into the membrane, leaving the mature TCR chain on the cell surface. The mature TCR chain comprises only the variable region and the constant region. The mature α-chain of hTERT-TCR-1 can be represented by the amino acid sequence set forth in SEQ ID NO: 38, which consists of the variable region of SEQ ID NO: 9 and the constant region of SEQ ID NO: 12. The mature β-chain of hTERT-TCR-1 can be represented by the amino acid sequence set forth in SEQ ID NO: 40, which consists of the variable region of SEQ ID NO: 11 and the constant region of SEQ ID NO: 13.

The nucleic acid molecule may encode a TCR comprising an α-chain comprising the amino acid sequence set forth in SEQ ID NO: 38, or a variant thereof. A variant of SEQ ID NO: 38 is an amino acid sequence having at least 95%, 96%, 97%, 98% or 99% sequence identity to SEQ ID NO: 38, with the proviso that the CDR sequences are as defined above.

The nucleic acid molecule may encode a TCR comprising a β-chain comprising the amino acid sequence set forth in SEQ ID NO: 40, or a variant thereof. A variant of SEQ ID NO: 40 is an amino acid sequence having at least 95%, 96%, 97%, 98% or 99% sequence identity to SEQ ID NO: 40, with the proviso that the CDR sequences are as defined above.

The nucleic acid molecule may in particular encode a TCR comprising an α-chain comprising the amino acid sequence set forth in SEQ ID NO: 38, or an amino acid sequence having at least 95% sequence identity thereto; and a β-chain comprising the amino acid sequence set forth in SEQ ID NO: 40, or an amino acid sequence having at least 95% sequence identity thereto.

As noted above, the encoded specific binding molecule may comprise N-terminally truncated variable regions of an α- and β-chain. A mature α-chain consisting of the truncated variable region of SEQ ID NO: 8 and the α-chain constant region of SEQ ID NO: 12 can be represented by the amino acid sequence set forth in SEQ ID NO: 37. A mature β-chain consisting of the truncated variable region of SEQ ID NO: 10 and the β-chain constant region of SEQ ID NO: 13 can be represented by the amino acid sequence set forth in SEQ ID NO: 39.

The nucleic acid molecule may thus encode a TCR comprising an α-chain comprising the amino acid sequence set forth in SEQ ID NO: 37, or a variant thereof. A variant of SEQ ID NO: 37 is an amino acid sequence having at least 95%, 96%, 97%, 98% or 99% sequence identity to SEQ ID NO: 37, with the proviso that the CDR sequences are as defined above.

The nucleic acid molecule may also encode a TCR comprising a β-chain comprising the amino acid sequence set forth in SEQ ID NO: 39, or a variant thereof. A variant of SEQ ID NO: 39 is an amino acid sequence having at least 95%, 96%, 97%, 98% or 99% sequence identity to SEQ ID NO: 39, with the proviso that the CDR sequences are as defined above.

The nucleic acid molecule may in particular encode a TCR comprising an α-chain comprising the amino acid sequence set forth in SEQ ID NO: 37, or an amino acid sequence having at least 95% sequence identity thereto; and a β-chain comprising the amino acid sequence set forth in SEQ ID NO: 39, or an amino acid sequence having at least 95% sequence identity thereto.

The leader sequence of the hTERT-TCR-1 α-chain has the amino acid sequence set forth in SEQ ID NO: 31, and the leader sequence of the hTERT-TCR-1 β-chain has the amino acid sequence set forth in SEQ ID NO: 32. It is believed that TCR chain leader sequences are largely interchangeable, so the chains of the TCR encoded by the nucleic acid molecule may comprise any known TCR leader sequences. The chains of the encoded TCR may comprise their native leader sequences, i.e. the α-chain of the TCR may comprise or consist of SEQ ID NO: 31 or a variant thereof, and the β-chain may comprise or consist of the amino acid sequence set forth in SEQ ID NO: 32 or a variant thereof. A variant of SEQ ID NO: 31 is an amino acid sequence with at least 70%, 75%, 80%, 85%, 90% or 95% sequence identity to SEQ ID NO: 31; a variant of SEQ ID NO: 32 is an amino acid sequence with at least 70%, 75%, 80%, 85%, 90%, 95% to SEQ ID NO: 32.

The α-chain of hTERT-TCR-1 has the amino acid sequence set forth in SEQ ID NO: 15. The α chain of hTERT-TCR-1 consists of, in the following order from N-terminus to C-terminus, the leader sequence of SEQ ID NO: 31, the variable region of SEQ ID NO: 9 and the constant region of SEQ ID NO: 12. In a particular embodiment the encoded TCR molecule comprises an α-chain comprising or consisting of the amino acid sequence set forth in SEQ ID NO: 15, or a variant thereof. A variant of SEQ ID NO: 15 is an amino acid sequence having at least 95%, 96%, 97%, 98% or 99% sequence identity to SEQ ID NO: 15, with the proviso that the CDR sequences are as defined above.

The β-chain of hTERT-TCR-1 has the amino acid sequence set forth in SEQ ID NO: 17. The β-chain of hTERT-TCR-1 consists of, in the following order from N-terminus to C-terminus, the leader sequence of SEQ ID NO: 32, the variable region of SEQ ID NO: 11 and the constant region of SEQ ID NO: 13. In a particular embodiment the encoded TCR molecule comprises a β-chain comprising or consisting of the amino acid sequence set forth in SEQ ID NO: 17, or a variant thereof. A variant of SEQ ID NO: 17 is an amino acid sequence having at least 95%, 96%, 97%, 98% or 99% sequence identity to SEQ ID NO: 17, with the proviso that the CDR sequences are as defined above.

In a particular embodiment of the disclosure, provided herein is a nucleic acid molecule which encodes a TCR molecule comprising an α-chain comprising or consisting of the amino acid sequence set forth in SEQ ID NO: 15, or an amino acid sequence having at least 95% sequence identity thereto; and a β-chain comprising or consisting of the amino acid sequence set forth in SEQ ID NO: 17, or an amino acid sequence having at least 95% sequence identity thereto.

As detailed above, in certain embodiments of the disclosure, the encoded specific binding molecule comprises N-terminally truncated variable regions. As set out above, a truncated version of the variable region of the hTERT-TCR-1 α-chain has the sequence set forth in SEQ ID NO: 8 and a truncated version of the variable region of the hTERT-TCR-1 β-chain has the sequence set forth in SEQ ID NO: 10.

A TCR α-chain consisting of, in the following order from N-terminus to C-terminus, the leader sequence of SEQ ID NO: 31, the truncated variable region of SEQ ID NO: 8 and the constant region of SEQ ID NO: 12 has the amino acid sequence set forth in SEQ ID NO: 14. The encoded TCR molecule may comprise an α-chain comprising or consisting of the amino acid sequence set forth in SEQ ID NO: 14, or a variant thereof. A variant of SEQ ID NO: 14 is an amino acid sequence having at least 95%, 96%, 97%, 98% or 99% sequence identity to SEQ ID NO: 14, with the proviso that the CDR sequences are as defined above.

A TCR β-chain consisting of, in the following order from N-terminus to C-terminus, the leader sequence of SEQ ID NO: 32, the truncated variable region of SEQ ID NO: 10 and the constant region of SEQ ID NO: 13 has the amino acid sequence set forth in SEQ ID NO: 16. The encoded TCR molecule may comprise a β-chain comprising or consisting of the amino acid sequence set forth in SEQ ID NO: 16, or a variant thereof. A variant of SEQ ID NO: 16 is an amino acid sequence having at least 95%, 96%, 97%, 98% or 99% sequence identity to SEQ ID NO: 16, with the proviso that the CDR sequences are as defined above.

In an embodiment, provided herein is a nucleic acid molecule which encodes a TCR molecule comprising an α-chain comprising or consisting of the amino acid sequence set forth in SEQ ID NO: 14, or an amino acid sequence having at least 95% sequence identity thereto; and a β-chain comprising or consisting of the amino acid sequence set forth in SEQ ID NO: 16, or an amino acid sequence having at least 95% sequence identity thereto.

In a particular embodiment, the nucleic acid molecule provided herein encodes hTERT-TCR-1, that is to say a specific binding molecule with an α-chain (corresponding to the first polypeptide) comprising or consisting of the amino acid sequence set forth in SEQ ID NO: 15, and a β-chain (corresponding to the second polypeptide) comprising or consisting of the amino acid sequence set forth in SEQ ID NO: 17.

In another embodiment of the disclosure, provided herein is a nucleic acid molecule which encodes a TCR molecule comprising an α-chain comprising a leader sequence N-terminal to the amino acid sequence set forth in SEQ ID NO: 37 or 38, or an amino acid sequence having at least 95% sequence identity thereto; and a β-chain comprising a leader sequence N-terminal to the amino acid sequence set forth in SEQ ID NO: 39 or 40, or an amino acid sequence having at least 95% sequence identity thereto. In such an embodiment the leader sequence in the α-chain may be a leader sequence other than SEQ ID NO: 31 or a variant thereof and in the β-chain the leader sequence may be a leader sequence other than SEQ ID NO: 32 or a variant thereof.

The TCR molecule encoded by the nucleic acid molecule disclosed herein may be encoded as a single chain TCR (scTCR). In an scTCR the α-chain and the β-chain are encoded as a single polypeptide chain. The α- and β-chains may be connected by a linker. The linker and the α- and β-chains of the scTCR may be as described above.

Preferably, the α- and β-chains are connected by a self-splicing 2A linker. In a particular embodiment, the nucleic acid molecule disclosed herein encodes an scTCR comprising the hTERT-TCR-1 α-chain connected to the hTERT-TCR-1 β-chain via a 2A linker. In such an scTCR, the hTERT-TCR-1 α-chain may be located at the N-terminus of the polypeptide chain and the hTERT-TCR-1 β-chain at the C-terminus, or the hTERT-TCR-1 α-chain may be located at the C-terminus of the polypeptide chain and the hTERT-TCR-1 β-chain at the N-terminus. The amino acid sequence of such an scTCR is set forth in SEQ ID NO: 20. SEQ ID NO: 20 consists of, from N-terminus to C-terminus, the hTERT-TCR-1 α-chain of SEQ ID NO: 15, the 2A peptide of SEQ ID NO: 18 and the hTERT-TCR-1 β-chain of SEQ ID NO: 17. The nucleic acid molecule disclosed herein may encode an scTCR comprising or consisting of the amino acid sequence set forth in SEQ ID NO: 20, or a variant thereof. A variant of SEQ ID NO: 20 has an amino acid sequence with at least 95%, 96%, 97%, 98% or 99% sequence identity to SEQ ID NO: 20, with the proviso that the CDR sequences are as set out above.

Alternatively, the scTCR encoded by the nucleic acid molecule disclosed herein may comprise α- and β-chains with N-terminally truncated variable regions, as discussed above. The amino acid sequence of such an scTCR is set forth in SEQ ID NO: 19, which consists of, from N-terminus to C-terminus, the modified hTERT-TCR-1 α-chain of SEQ ID NO: 14, the 2A peptide of SEQ ID NO: 18 and the modified hTERT-TCR-1 β-chain of SEQ ID NO: 16. The nucleic acid molecule disclosed herein may encode an scTCR comprising or consisting of the amino acid sequence set forth in SEQ ID NO: 19, or a variant thereof. A variant of SEQ ID NO: 19 has an amino acid sequence with at least 95%, 96%, 97%, 98% or 99% sequence identity to SEQ ID NO: 19, with the proviso that the CDR sequences are as set out above.

As detailed above, 2A peptides undergo co-translational cleavage between their C-terminal proline residue and penultimate glycine residue. The terminal proline of a 2A linker thus forms the N-terminal residue of the downstream polypeptide, while all the other residues of the 2A linker form the C-terminus of the upstream polypeptide. Thus TCR chains encoded within an scTCR as detailed above will, when expressed, comprise residual residues derived from the 2A peptide. The terminal proline residue of the 2A peptide will be located at the N-terminus of the TCR chain encoded downstream of the 2A peptide, i.e. at the N-terminus of the leader sequence of the relevant TCR chain. Since the leader sequence is cleaved during insertion of the TCR chain into the membrane, the terminal proline residue of the 2A peptide will not be present in the mature, membrane-anchored TCR. However, all other residues of the 2A peptide will be located at the C-terminus of the TCR chain encoded upstream of the 2A peptide in the scTCR. These residues will not be removed during TCR maturation and hence will be present in the mature, membrane-anchored TCR. Accordingly, a mature TCR encoded as an scTCR by the nucleic acid molecule disclosed herein may comprise an α- or a β-chain which comprises residual 2A peptide residues at its C-terminus.

As detailed above, the nucleic acid molecule disclosed herein encodes a specific binding molecule which may comprise a first polypeptide and a second polypeptide, comprising respectively a variable region of an α-chain and a constant region of an α-chain, and a variable region of a β-chain and a constant region of a β-chain. As detailed above, the constant region of the α-chain and the constant region of the β-chain may be full-length or truncated. Specific binding molecules in which the constant region of the α- and β-chains are full-length are TCRs (that is to say membrane-bound TCRs, such as are found in nature) and are discussed above.

The nucleic acid molecule provided herein may encode a specific binding molecule comprising a first polypeptide which comprises a truncated constant region of an α-chain. In particular, the constant region of an α-chain may be truncated at its C-terminus, such that the transmembrane and intracellular domains are deleted, rendering the constant region soluble. The truncated constant region of an α-chain is preferably a truncated version of the human TCR α-chain constant region. A particular truncated constant region of an α-chain is presented in SEQ ID NO: 29. The amino acid sequence set forth in SEQ ID NO: 29 corresponds to amino acids 1 to 96 of the human TCR α-chain constant region, i.e.

amino acids 1 to 96 of SEQ ID NO: 12. Deletion of amino acids 97 to 142 from SEQ ID NO: 12 yields SEQ ID NO: 29.

The nucleic acid molecule provided herein may similarly encode a specific binding molecule comprising a second polypeptide which comprises a truncated constant region of a β-chain. In particular, the constant region of a β-chain may be truncated at its C-terminus, such that the transmembrane and intracellular domains are deleted, rendering the constant region soluble. The truncated constant region of a β-chain is preferably a truncated version of a human TCR β-chain constant region, most preferably a truncated version of the human β-chain subtype 2 constant region (as detailed above, hTERT-TCR-1 comprises a β-chain with a subtype 2 constant region). A particular truncated constant region of a β-chain is presented in SEQ ID NO: 30. The amino acid sequence set forth in SEQ ID NO: 30 corresponds to amino acids 1 to 132 of the human TCR β-chain subtype 2 constant region, i.e. amino acids 1 to 132 of SEQ ID NO: 13. Deletion of amino acids 133 to 179 from SEQ ID NO: 13 yields SEQ ID NO: 30.

In a native αβ TCR, the α-chain and the β-chain are covalently joined by disulphide bonds which form between cysteine residues present in the constant regions of the two chains. Truncation of the constant regions, as detailed above, may result in the loss of a cysteine residue responsible for inter-chain disulphide bond formation from one or both of the constant regions. In order that the first polypeptide and second polypeptide of the encoded specific binding molecule associate (as may be required for the specific binding molecule to function) when each comprises a truncated constant region of a TCR chain, one or more additional cysteine residues may be introduced into the truncated constant region of an α-chain and the truncated constant region of a β-chain. Disulphide bonds may form between appropriately located cysteine residues introduced into the truncated constant regions of the α- and β-chains, linking the first polypeptide and the second polypeptide.

If additional cysteine residues are to be introduced into truncated constant regions of an α-chain and a β-chain to enable the formation of a disulphide bond between the first and second polypeptide chains of the specific binding molecule, it is important that the cysteine residues are introduced at appropriate locations. The introduced cysteine residues should be introduced at locations such that formation of the disulphide bond leads to the formation of a functional complex in which the variable regions are correctly located and orientated with respect to each other e.g. as disclosed by Boulter, J. M. et al. (*Protein Eng. Des. Sel.* 16(9): 707-711, 2003). Appropriate locations for introduction of cysteine residues may be identified by e.g. analysis of TCR chain structure and/or by trial-and-error using the techniques discussed below and set forth in the examples to identify functional specific binding molecules.

A cysteine residue may be introduced into a truncated constant region of an α- or β-chain at any suitable location by insertion (addition of a cysteine residue between two existing amino acids) or by substitution (substitution of an existing, non-cysteine residue for a cysteine residue). For instance, a cysteine residue may be introduced into the truncated constant region of an α-chain of SEQ ID NO: 29 by substituting the threonine residue at position 49 for a cysteine residue. A modified version of SEQ ID NO: 29 which contains this Thr49Cys substitution, but is otherwise unaltered, has the amino acid sequence set forth in SEQ ID NO: 21. Correspondingly, a cysteine residue may be introduced into the truncated constant region of a β-chain of SEQ ID NO: 30 by substituting the serine residue at position 57 for a cysteine residue. A modified version of SEQ ID NO: 30, which contains this Ser57Cys substitution, has the amino acid sequence set forth in SEQ ID NO: 22.

In a particular embodiment, the nucleic acid molecule encodes a specific binding molecule comprising a first polypeptide which comprises a variable region of an α-chain as described above and a constant region of an α-chain comprising or consisting of the amino acid sequence set forth in SEQ ID NO: 21, or a variant thereof; and a second polypeptide which comprises a variable region of a β-chain as described above and a constant region of a β-chain comprising or consisting of SEQ ID NO: 22, or a variant thereof. A variant of SEQ ID NO: 21 is an amino acid sequence which has at least 95%, 96%, 97%, 98% or 99% sequence identity to SEQ ID NO: 21; a variant of SEQ ID NO: 22 is an amino acid sequence which has at least 95%, 96%, 97%, 98% or 99% sequence identity to SEQ ID NO: 22.

Preferably a variant of SEQ ID NO: 21 has the above-described cysteine residue at position 49, or a position corresponding to position 49 of SEQ ID NO: 21. A position corresponding to position 49 of SEQ ID NO: 21 may be identified by sequence alignment. When an amino acid sequence of interest is aligned with SEQ ID NO: 21 (the reference sequence), the amino acid position in the sequence of interest which is aligned with position 49 of SEQ ID NO: 21 is defined as the position within the sequence of interest corresponding to position 49 of SEQ ID NO: 21. A sequence alignment may be performed using any suitable method, for instance a computer programme such as EMBOSS Needle or EMBOSS stretcher (both Rice, P. et al., *Trends Genet.* 16(6): 276-277, 2000) may be used for pairwise sequence alignments while Clustal Omega (Sievers, F. et al., *Mol. Syst. Biol.* 7:539, 2011) or MUSCLE (Edgar, R. C., *Nucleic Acids Res.* 32(5):1792-1797, 2004) may be used for multiple sequence alignments. Such computer programmes may be used with the standard input parameters, e.g. the standard Clustal Omega parameters: matrix Gonnet, gap opening penalty 6, gap extension penalty 1; or the standard EMBOSS Needle parameters: matrix BLOSUM62, gap opening penalty 10, gap extension penalty 0.5. Any other suitable parameters may alternatively be used.

Preferably a variant of SEQ ID NO: 22 has the above-described cysteine residue at position 57, or a position corresponding to position 57 of SEQ ID NO: 22. Methods by which an amino acid position in a sequence of interest which corresponds to a particular position in a given reference sequence may be identified are discussed above.

A first polypeptide as described above comprising a constant region of an α-chain with the amino acid sequence set forth in SEQ ID NO: 21 forms a covalent complex with a second polypeptide as described above comprising a constant region of a β-chain with the amino acid sequence set forth in SEQ ID NO: 22. The covalent linkage is formed via a disulphide bond between the cysteine residues introduced into the constant regions of the α- and β-chains, discussed above. The covalent complex formed is a functional specific binding molecule.

A first polypeptide which comprises the variable region of the hTERT-TCR-1 α-chain (which has the amino acid sequence set forth in SEQ ID NO: 9) and a constant region of an α-chain having the amino acid sequence set forth in SEQ ID NO: 21 has the amino acid sequence set forth in SEQ ID NO: 42. The encoded specific binding molecule may comprise a first polypeptide comprising or consisting of the amino acid sequence set forth in SEQ ID NO: 42, or a variant thereof. A variant of SEQ ID NO: 42 has an amino acid sequence with at least 95%, 96%, 97%, 98% or 99% sequence identity to SEQ ID NO: 42, with the proviso that the CDR sequences are as defined above. Preferably a variant of SEQ ID NO: 42 comprises the above-described cysteine residue at position 49 of the constant region of an α-chain, or a position corresponding to position 49 of the constant region of an α-chain.

A second polypeptide which comprises the variable region of the hTERT-TCR-1 β-chain (which has the amino acid sequence set forth in SEQ ID NO: 11) and a constant region of a β-chain having the amino acid sequence set forth in SEQ ID NO: 22 has the amino acid sequence set forth in SEQ ID NO: 44. The encoded specific binding molecule may comprise a second polypeptide comprising or consisting of the amino acid sequence set forth in SEQ ID NO: 44, or a variant thereof. A variant of SEQ ID NO: 44 has an amino acid sequence with at least 95%, 96%, 97%, 98% or 99% sequence identity to SEQ ID NO: 44, with the proviso that the CDR sequences are as defined above. Preferably a variant of SEQ ID NO: 44 comprises the above-described cysteine residue at position 57 of the constant region of a β-chain, or a position corresponding to position 57 of the constant region of a β-chain.

In a particular embodiment, the nucleic acid molecule provided herein encodes a specific binding molecule comprising a first polypeptide which comprises or consists of the amino acid sequence set forth in SEQ ID NO: 42, or an amino acid sequence having at least 95% sequence identity thereto; and a second polypeptide which comprises or consists of the amino acid sequence set forth in SEQ ID NO: 44, or an amino acid sequence having at least 95% sequence identity thereto.

A first polypeptide which comprises the truncated variable region of the hTERT-TCR-1 α-chain of SEQ ID NO: 8 and the constant region of an α-chain of SEQ ID NO: 21 has the amino acid sequence set forth in SEQ ID NO: 41. The encoded specific binding molecule may comprise a first polypeptide comprising or consisting of the amino acid sequence set forth in SEQ ID NO: 41, or a variant thereof. A variant of SEQ ID NO: 41 has an amino acid sequence with at least 95%, 96%, 97%, 98% or 99% sequence identity to SEQ ID NO: 41, with the proviso that the CDR sequences are as defined above. Preferably a variant of SEQ ID NO: 41 comprises the above-described cysteine residue at position 49 of the constant region of an α-chain, or a position corresponding to position 49 of the constant region of an α-chain.

A second polypeptide which comprises the modified variable region of the hTERT-TCR-1 β-chain of SEQ ID NO: 10 and the constant region of a β-chain of SEQ ID NO: 22 has the amino acid sequence set forth in SEQ ID NO: 43. The encoded specific binding molecule may comprise a second polypeptide comprising or consisting of the amino acid sequence set forth in SEQ ID NO: 43, or a variant thereof. A variant of SEQ ID NO: 43 has an amino acid sequence with at least 95%, 96%, 97%, 98% or 99% sequence identity to SEQ ID NO: 43, with the proviso that the CDR sequences are as defined above. Preferably a variant of SEQ ID NO: 43 comprises the above-described cysteine residue at position 57 of the constant region of a β-chain, or a position corresponding to position 57 of the constant region of a β-chain.

In a particular embodiment, the nucleic acid molecule provided herein encodes a specific binding molecule comprising a first polypeptide which comprises or consists of the amino acid sequence set forth in SEQ ID NO: 41, or an amino acid sequence having at least 95% sequence identity thereto; and a second polypeptide which comprises or consists of the amino acid sequence set forth in SEQ ID NO: 43, or an amino acid sequence having at least 95% sequence identity thereto.

The first and second polypeptides are encoded with leader sequences, which target the polypeptides for export from the cell in which they are produced (i.e. they function as signal sequences). As discussed above, TCR chain leader sequences are largely interchangeable, and selection of a suitable leader sequence is therefore straightforward for the skilled person. In a particular embodiment the first polypeptide comprises the leader sequence of the hTERT-TCR-1 α-chain or a variant thereof (i.e. the leader sequence of SEQ ID NO: 31 or a variant thereof) and the second polypeptide comprises the leader sequence of the hTERT-TCR-1 α-chain or a variant thereof (i.e. the leader sequence of SEQ ID NO: 32 or a variant thereof).

A first polypeptide of SEQ ID NO: 41, further comprising the leader sequence of SEQ ID NO: 31 at its N-terminus, has the amino acid sequence set forth in SEQ ID NO: 23. A first polypeptide of SEQ ID NO: 42, further comprising the leader sequence of SEQ ID NO: 31 at its N-terminus, has the amino acid sequence set forth in SEQ ID NO: 24.

A second polypeptide of SEQ ID NO: 43, further comprising the leader sequence of SEQ ID NO: 32 at its N-terminus, has the amino acid sequence set forth in SEQ ID NO: 25. A second polypeptide of SEQ ID NO: 44, further comprising the leader sequence of SEQ ID NO: 32 at its N-terminus, has the amino acid sequence set forth in SEQ ID NO: 26.

The first polypeptide may thus comprise or consist of the amino acid sequence set forth in SEQ ID NO: 23 or SEQ ID NO: 24, or a variant of SEQ ID NO: 23 or SEQ ID NO: 24 (i.e. an amino acid sequence having at least 95%, 96%, 97%, 98% or 99% sequence identity to SEQ ID NO: 23 or SEQ ID NO: 24, respectively), with the proviso that the CDR sequences are as defined above. Preferably a variant of SEQ ID NO: 23 or SEQ ID NO: 24 comprises the above-described cysteine residue at position 49 of the constant region of an α-chain, or a position corresponding to position 49 of the constant region of an α-chain.

The second polypeptide may thus comprise or consist of the amino acid sequence set forth in SEQ ID NO: 25 or SEQ ID NO: 26, or a variant of SEQ ID NO: 25 or SEQ ID NO: 26 (i.e. an amino acid sequence having at least 95%, 96%, 97%, 98% or 99% sequence identity to SEQ ID NO: 25 or SEQ ID NO: 26, respectively), with the proviso that the CDR sequences are as defined above. Preferably a variant of SEQ ID NO: 25 or SEQ ID NO: 26 comprises the above-described cysteine residue at position 57 of the constant region of a β-chain, or a position corresponding to position 57 of the constant region of a β-chain.

In a particular embodiment the nucleic acid molecule disclosed herein encodes a specific binding molecule comprising a first polypeptide comprising or consisting of the amino acid sequence set forth in SEQ ID NO: 23, or an amino acid sequence having at least 95% sequence identity to SEQ ID NO: 23; and a second polypeptide comprising or consisting of the amino acid sequence set forth in SEQ ID NO: 25, or an amino acid sequence having at least 95% sequence identity to SEQ ID NO: 25.

In another embodiment the nucleic acid molecule disclosed herein encodes a specific binding molecule comprising a first polypeptide comprising or consisting of the amino acid sequence set forth in SEQ ID NO: 24, or an amino acid sequence having at least 95% sequence identity to SEQ ID NO: 24; and a second polypeptide comprising or consisting of the amino acid sequence set forth in SEQ ID NO: 26, or an amino acid sequence having at least 95% sequence identity to SEQ ID NO: 26.

As noted above, a constant region of an α-chain or β-chain which has been C-terminally truncated to remove the transmembrane domain is soluble. Accordingly, a specific binding molecule comprising a first polypeptide which comprises such a truncated α-chain and a second polypeptide which comprises such a truncated β-chain may be soluble. The term "soluble" is used herein to denote a species which is water-soluble, in particular with respect to proteins to denote proteins which lack membrane-embedded or transmembrane domains.

Thus the nucleic acid molecule may encode a soluble specific binding molecule, comprising a first polypeptide as described above which comprises a truncated, soluble constant region of an α-chain and a second polypeptide as described above which comprises a truncated, soluble constant region of a β-chain. The specific binding molecule may be a soluble TCR.

Soluble TCRs (sTCRs) comprise the variable regions, and the extracellular domains of the constant regions, of the α- and β-chains present in native TCRs, but lack the transmembrane and cytoplasmic domains of the constant regions. Soluble TCRs may be expressed by any cell, and are secreted. Soluble TCRs are described in detail in Walseng et al. (2015), PLoS ONE 10(4): e0119559. It can thus be seen that soluble TCRs comprise a truncated TCR α-chain (corresponding to the first polypeptide) and a truncated β-chain (corresponding to the second polypeptide).

It is an essential aspect of a soluble TCR that the truncated α- and β-chains of the mature TCR are joined. If they are not joined, the chains will diffuse apart in solution and the TCR will function poorly, if at all. The chains may be joined covalently or non-covalently. A preferred method by which the truncated α- and β-chains can be covalently joined is by one or more disulphide bonds. These may form between cysteine residues present in the native TCR chain sequences, but in a preferred embodiment the TCR chains comprise truncated constant regions into which one or more additional cysteine residues have been inserted, as described above.

An alternative method by which the α- and β-chains of the soluble TCR may be joined is by non-covalent interactions. In a particular embodiment, leucine zippers are used to non-covalently join the chains. In this embodiment, both the truncated α- and truncated β-chains comprise leucine zipper domains at the C-termini of their truncated constant regions (i.e. the truncated α-chain comprises a leucine zipper domain at its C-terminus and the truncated β-chain also comprises a leucine zipper domain at its C-terminus). Leucine zippers, and their sequences, are well-known in the art, and are reviewed in e.g. Busch & Sassone-Corsi (1990), Trends Genet 6: 36-40. In some embodiments, both covalent and non-covalent methods may be used to join the α- and β-chains of the soluble TCR, e.g. the α- and β-chains may be both cysteine-modified to enable disulphide bond formation and include leucine zipper domains.

Thus when the encoded specific binding molecule is a soluble TCR the first and second polypeptides may each comprise a C-terminal leucine zipper domain. The truncated α- and β-chains may be as described above. However, as noted above, if the polypeptide chains comprise C-terminal leucine zippers it is not necessary that additional cysteine residues are introduced to allow disulphide bond formation. Thus the constant region of an α-chain may comprise or consist of the amino acid sequence set forth in SEQ ID NO: 29, or a variant thereof. A variant of SEQ ID NO: 29 is an amino acid sequence having at least 95%, 96%, 97%, 98% or 99% sequence identity to SEQ ID NO: 29. The constant region of a β-chain may comprise or consist of the amino acid sequence set forth in SEQ ID NO: 30, or a variant thereof. A variant of SEQ ID NO: 30 is an amino acid sequence having at least 95%, 96%, 97%, 98% or 99% sequence identity to SEQ ID NO: 30.

In a particular embodiment the encoded soluble TCR comprises a truncated α-chain comprising the amino acid sequence set forth in SEQ ID NO: 54, or a variant thereof; and a truncated β-chain comprising the amino acid sequence set forth in SEQ ID NO: 56, or a variant thereof. SEQ ID NO: 54 is the sequence of a truncated α-chain consisting of the N-terminally truncated variable region of SEQ ID NO: 8 and the C-terminally truncated constant region of SEQ ID NO: 29. SEQ ID NO: 56 is the sequence of a truncated β-chain consisting of the N-terminally truncated variable region of SEQ ID NO: 10 and the C-terminally truncated constant region of SEQ ID NO: 30. A variant of SEQ ID NO: 54 is an amino acid sequence having at least 95%, 96%, 97%, 98% or 99% sequence identity to SEQ ID NO: 54, with the proviso that the CDR sequences are as defined above. A variant of SEQ ID NO: 56 is an amino acid sequence having at least 95%, 96%, 97%, 98% or 99% sequence identity to SEQ ID NO: 56, with the proviso that the CDR sequences are as defined above.

In another embodiment the encoded soluble TCR comprises a truncated α-chain comprising the amino acid sequence set forth in SEQ ID NO: 55, or a variant thereof, and a truncated β-chain comprising the amino acid sequence set forth in SEQ ID NO: 57, or a variant thereof. SEQ ID NO: 55 is the sequence of a truncated α-chain consisting of the variable region of SEQ ID NO: 9 and the C-terminally truncated constant region of SEQ ID NO: 29. SEQ ID NO: 57 is the sequence of a truncated β-chain consisting of the variable region of SEQ ID NO: 10 and the C-terminally truncated constant region of SEQ ID NO: 30. A variant of SEQ ID NO: 55 is an amino acid sequence having at least 95%, 96%, 97%, 98% or 99% sequence identity to SEQ ID NO: 55, with the proviso that the CDR sequences are as defined above. A variant of SEQ ID NO: 57 is an amino acid sequence having at least 95%, 96%, 97%, 98% or 99% sequence identity to SEQ ID NO: 57, with the proviso that the CDR sequences are as defined above.

The truncated α-chains of SEQ ID NOs: 54 and 55, or variants thereof, are encoded with a leader sequence. The leader sequence may be the α-chain leader sequence of SEQ ID NO: 31. The truncated β-chains of SEQ ID NOs: 56 and 57, or variants thereof, are also encoded with a leader sequence. The leader sequence may be the β-chain leader sequence of SEQ ID NO: 32.

The soluble TCR may be encoded as a single-chain soluble TCR. Preferably, when the soluble TCR is encoded as a single chain, the truncated α-chain and the truncated β-chain are joined by a linker, such as the 2A linker of SEQ ID NO: 18.

The single-chain soluble TCR may comprise or consist of the truncated α-chain of SEQ ID NO: 23 linked to the truncated β-chain of SEQ ID NO: 25. As detailed above, the truncated α-chain may be located at the N-terminus of the single-chain soluble TCR or the truncated β-chain may be located at the N-terminus of the single-chain soluble TCR. In a particular embodiment the single-chain soluble TCR comprises or consists of the amino acid sequence set forth in SEQ ID NO: 27, or a variant thereof. SEQ ID NO: 27 consists of, in the following order from N-terminus to C-terminus, the truncated α-chain of SEQ ID NO: 23, the 2A peptide of SEQ ID NO: 18 and the truncated β-chain of SEQ ID NO: 25. A variant of SEQ ID NO: 27 is an amino acid sequence having at least 95%, 96%, 97%, 98% or 99% sequence identity to SEQ ID NO: 27, with the proviso that the CDR sequences are as defined above.

The single-chain soluble TCR may alternatively comprise or consist of the truncated α-chain of SEQ ID NO: 24 linked to the truncated β-chain of SEQ ID NO: 26. In a particular embodiment the single-chain soluble TCR comprises or consists of the amino acid sequence set forth in SEQ ID NO: 28, or a variant thereof. SEQ ID NO: 28 consists of, in the following order from N-terminus to C-terminus, the truncated α-chain of SEQ ID NO: 24, the 2A peptide of SEQ ID NO: 18 and the truncated β-chain of SEQ ID NO: 26. A variant of SEQ ID NO: 28 is an amino acid sequence having at least 95%, 96%, 97%, 98% or 99% sequence identity to SEQ ID NO: 28, with the proviso that the CDR sequences are as defined above.

As detailed above, the truncated TCR chains of SEQ ID NOs: 23-26 comprise cysteine residues which have been introduced into their constant regions. Preferably a variant of SEQ ID NO: 27 or SEQ ID NO: 28 comprises the above-described cysteine residue at position 49 of the constant region of an α-chain, or a position corresponding to position 49 of the constant region of an α-chain, and the above-described cysteine residue at position 57 of the constant region of a β-chain, or a position corresponding to position 57 of the constant region of a β-chain. In the soluble TCRs encoded as single-chain soluble TCRs of SEQ ID NO: 27 or 28, the polypeptide chains are joined by disulphide bonds between the introduced cysteine residues.

At least one chain of the soluble TCR may be encoded with an affinity tag, which may be used in purification of the soluble TCR following its synthesis. Such a tag may be any suitable tag known to the skilled person, e.g. a FLAG-tag, a His-tag, an HA-tag, a Strep-tag, an S-tag, a Myc-tag, glutathione S-transferase (GST), maltose-binding protein (MBP), etc. The tag is preferably located at the C-terminus of either the α- or β-chain. Thus, a soluble TCR may be encoded so as to comprise a purification tag in its α- and/or β-chain, preferably at the C-terminus of the chain(s). A soluble TCR chain may be encoded with a linker and/or a protease cleavage site between the main chain sequence (i.e. the variable region, the truncated constant region, and if present the leucine zipper domain) and the purification tag. Appropriate protease cleavage sites are well-known to the skilled person and include thrombin, factor Xa, enterokinase, human rhinovirus (HRV) 3C and tobacco etch virus (TEV) cleavage sites. Alternatively the tag may be joined directly to the C-terminus of the truncated α- or β-chain.

In another embodiment, the nucleic acid molecule provided encodes a specific binding molecule as described above, comprising a first polypeptide which comprises a truncated constant region of an α-chain and a second polypeptide which comprises a truncated region of a β-chain, in which the specific binding molecule is a TCR-CAR.

A CAR is a chimeric antigen receptor. As is known to the skilled person, a CAR commonly comprises a single-chain Fv domain (scFv) derived from an antibody fused to a signalling tail which, upon antigen binding, transduces a signal across a cell membrane to activate the effector functions of an immune effector cell, e.g. a T-cell or an NK cell. CARs may be used to redirect immune effector cells to a target of interest in immunotherapy, particularly cancer immunotherapy. CARs, and their therapeutic uses, are described in Maude et al. (Blood, Volume 125(26), 4017-4023, 2015). CAR immunotherapy has proven successful in a number of trials, but is limited by the breadth of available targets. A TCR-CAR is based on the same rationale as a standard CAR, but the scFv of a standard CAR is substituted with a "soluble TCR". This provides a construct with the functional potential of a CAR, but with the substrate breadth of a TCR (i.e. they may be directed against any peptide resulting from cellular protein degradation). TCR-CARs are described in Walseng et al. (Scientific Reports 7: 10713, 2017).

A TCR-CAR encoded by the disclosed nucleic acid molecule comprises a first polypeptide as described above (i.e. comprising a variable region of an α-chain and a C-terminally truncated constant region of an α-chain) and a second polypeptide as described above (i.e. comprising a variable region of a β-chain and C-terminally truncated constant region of a β-chain). In the TCR-CAR either the first polypeptide or the second polypeptide further comprises a transmembrane domain and one or more intracellular signalling domains. The transmembrane domain and the intracellular signalling domain(s) together constitute the CAR signalling tail.

TCR-CARs may be expressed by immune effector cells, in particular T-cells or NK cells, to recognise target antigen-MHC complexes and thus activate the effector function(s) of the immune effector cell. When expressed by an immune effector cell, a TCR-CAR is located at the membrane (it is a transmembrane protein). The variable regions and truncated constant regions of the TCR chains are extracellular, and the intracellular signalling domain(s) is/are intracellular.

As noted above, in a TCR-CAR either the first polypeptide or the second polypeptide comprises a CAR signalling tail. In other words, the CAR signalling tail is joined to one or other of the two polypeptides. The CAR-TCR comprises only a single CAR-signalling tail, i.e. a CAR signalling tail is not joined to both polypeptides. The CAR signalling tail is located at the C-terminus of the first or second polypeptide, C-terminal to the truncated constant region of a TCR chain. Thus the first or second polypeptide comprises, in order from N-terminus to C-terminus: a variable region of a TCR chain, a C-terminally truncated constant region of a TCR chain, and the CAR signalling tail. The CAR signalling tail may be located at the C-terminus of the first polypeptide chain, or the CAR signalling tail may be located at the C-terminus of the second polypeptide chain.

CARs are discussed in WO 2017/118745 (which is incorporated herein by reference), including suitable transmembrane domains and intracellular signalling domains which may be included in CARs. The same teaching applies with respect to TCR-CARs. The transmembrane domain may be based on or derived from the transmembrane domain of any transmembrane protein. Typically it may be, or may be derived from, a transmembrane domain from CD8α, CD28, CD4, CD3ζ, CD45, CD9, CD16, CD22, CD33, CD64, CD80, CD86, CD134, CD137, or CD154, preferably from a human said protein. In one embodiment, the transmembrane domain may be, or may be derived from, a transmembrane domain from CD8α, CD28, CD4, or CD3ζ, preferably from human CD28, CD4, or CD3ζ. In another embodiment the transmembrane domain may be synthetic in which case it would comprise predominantly hydrophobic residues such as leucine and valine. The transmembrane domain may be the transmembrane domain of the human TCR α-chain constant region or a human TCR β-chain constant region.

In a preferred embodiment the transmembrane domain is the transmembrane domain of human CD28, which has the amino acid sequence of SEQ ID NO: 45, or a variant thereof.

A variant of SEQ ID NO: 45 has an amino acid sequence having at least 95%, 96%, 97%, 98% or 99% sequence identity to SEQ ID NO: 45.

The term "intracellular signalling domain" refers herein to the part of the CAR signalling tail that participates in transducing the message of effective TCR-CAR binding to a target antigen-MHC complex into the interior of an immune effector cell expressing the TCR-CAR, to elicit effector cell function, e.g. activation, cytokine production, proliferation and/or cytotoxic activity, including the release of cytotoxic factors to the TCR-CAR-bound target cell, or other cellular responses elicited with antigen binding to the extracellular CAR domain. The term "effector function" refers to a specialised function of the cell. Effector function of a T-cell, for example, may be cytolytic activity or helper activity including the secretion of a cytokine. Thus, the term "intracellular signalling domain" refers to a protein domain which transduces the effector function signal and directs the cell to perform a specialised function. While an entire natural intracellular signalling domain can be employed, in many cases it is not necessary to use an entire domain as found in nature. To the extent that a truncated portion of an intracellular signalling domain is used, such a truncated portion may be used in place of the entire domain as long as it transduces the effector function signal. The term intracellular signalling domain is meant to include any truncated portion of an intracellular signalling domain sufficient to transduce effector function signal. The intracellular signalling domain is also known as the, "signal transduction domain," and is typically derived from portions of the human CD3ζ or FcRγ chains.

Additionally, to allow or to augment full activation of the immune effector cell the TCR-CAR may be provided with a secondary, or co-stimulatory domain. Thus, the intracellular signalling domain may initiate antigen-dependent primary activation (i.e. may be a primary cytoplasmic signalling sequence) and the co-stimulatory domain may act in an antigen-independent manner to provide a secondary or co-stimulatory signal (secondary cytoplasmic signalling sequence(s)). Primary cytoplasmic signalling sequences may regulate primary activation, including in an inhibitory way. Primary cytoplasmic signalling sequences that act in a co-stimulatory manner may contain signalling motifs which are known as immunoreceptor tyrosine-based activation motifs or ITAMs.

Examples of ITAM-containing primary cytoplasmic signalling sequences that may be used in the invention include those derived from TCRζ, FcRγ, FcRβ, CD3γ, CD3δ, CD3ε, CD5, CD22, CD79a, CD79b and CD66d. In certain particular embodiments, the intracellular signalling domain is derived from CD3ζ or FcRγ, preferably human CD3ζ or FcRγ.

In a preferred representative embodiment the intracellular signalling domain is a human CD3ζ domain having the amino acid sequence set forth in SEQ ID NO: 46, or a variant thereof. A variant of SEQ ID NO: 46 has an amino acid sequence having at least 95%, 96%, 97%, 98% or 99% sequence identity to SEQ ID NO: 46.

The term "co-stimulatory signalling domain" or "co-stimulatory domain", refers to the portion of the CAR comprising the intracellular domain of a co-stimulatory molecule. Co-stimulatory molecules are cell surface molecules other than antigen receptors or Fc receptors that provide a second signal required for efficient activation and function of an immune effector cell (e.g. a T-cell) upon binding to antigen. Examples of such co-stimulatory molecules include CD27, CD28, 4-IBB (CD137), OX40 (CD134), CD30, CD40, PD-1, ICOS (CD278), LFA-1, CD2, CD7, LIGHT, NKD2C, B7-H2 and a ligand that specifically binds CD83, more particularly the intracellular domains of such molecules. Preferably the molecules are human. Accordingly, while exemplary or preferred co-stimulatory domains are derived from 4-1BB, CD28 or OX40 (CD134), other co-stimulatory domains are contemplated for use with the TCR-CARs described herein. The co-stimulatory domains may be used singly or in combination (i.e. one or more co-stimulatory domains may be included). The inclusion of one or more co-stimulatory signalling domains may enhance the efficacy and expansion of immune effector cells expressing the TCR-CARs.

In an embodiment the co-stimulatory domain may be, or may include, the intracellular domain of human CD28 having the amino acid sequence of SEQ ID NO: 58, or a variant thereof. A variant of SEQ ID NO: 58 has an amino acid sequence having at least 95%, 96%, 97%, 98% or 99% sequence identity to SEQ ID NO: 58.

The intracellular signalling and co-stimulatory signalling domains may be linked in any order in tandem to the carboxyl terminus of the transmembrane domain. In a particular embodiment, the CAR signalling tail comprises, in the following order N-terminal to C-terminal, the CD28 transmembrane domain (or a variant thereof), the CD28 intracellular domain (or a variant thereof) and the CD3ζ intracellular domain (or a variant thereof). Such a CAR signalling tail (comprising non-variant sequences of the aforementioned domains) has the amino acid sequence set forth in SEQ ID NO: 59.

In a TCR-CAR, the first and second polypeptides are preferably covalently joined. The two polypeptides may be covalently joined by a disulphide bond. In particular, the first and second polypeptides may each comprise a truncated TCR chain constant region into which one or more cysteine residues have been introduced, as discussed above.

In a particular embodiment, the TCR-CAR comprises a first polypeptide which comprises the amino acid sequence set forth in SEQ ID NO: 42, or a variant thereof; and a second polypeptide which comprises the amino acid sequence set forth in SEQ ID NO: 48, or a variant thereof. SEQ ID NO: 48 consists of, from N-terminus to C-terminus, the variable region of a β-chain of SEQ ID NO: 11, the truncated constant region of a β-chain of SEQ ID NO: 22, the CD28 transmembrane domain of SEQ ID NO: 45, the CD28 intracellular signalling domain of SEQ ID NO: 58 and the CD3 intracellular signalling domain of SEQ ID NO: 46. A variant of SEQ ID NO: 48 has an amino acid sequence with at least 95%, 96%, 97%, 98% or 99% sequence identity to SEQ ID NO: 48, with the proviso that the CDR sequences are as defined above. Preferably a variant of SEQ ID NO: 48 comprises the above-described cysteine residue at position 57 of the constant region of a β-chain, or a position corresponding to position 57 of the constant region of a β-chain.

In another embodiment, the TCR-CAR comprises a first polypeptide which comprises the amino acid sequence set forth in SEQ ID NO: 47, or a variant thereof, and the second polypeptide comprises the amino acid sequence set forth in SEQ ID NO: 44, or a variant thereof. SEQ ID NO: 47 consists of, from N-terminus to C-terminus, the variable region of an α-chain of SEQ ID NO: 9, the truncated constant region of an α-chain of SEQ ID NO: 21, the CD28 transmembrane domain of SEQ ID NO: 45, the CD28 intracellular signalling domain of SEQ ID NO: 58 and the CD3 intracellular signalling domain of SEQ ID NO: 46. A variant of SEQ ID NO: 47 has an amino acid sequence with at least 95%, 96%, 97%, 98% or 99% sequence identity to SEQ ID NO: 47, with the proviso that the CDR sequences are as defined above. Preferably a variant of SEQ ID NO: 47 comprises the above-described cysteine residue at position 49 of the constant region of an α-chain, or a position corresponding to position 49 of the constant region of an α-chain.

Both the first and second polypeptides are encoded with an N-terminal leader sequence. The leader sequence of the first polypeptide may be the leader sequence of an α-chain of SEQ ID NO: 31, or a variant thereof, and the leader sequence of the second polypeptide may be the leader sequence of a β-chain of SEQ ID NO: 32, or a variant thereof.

In particular, the first polypeptide may consist of an amino acid sequence as defined above with the N-terminal leader sequence of SEQ ID NO: 31, and the second polypeptide may consist of the an amino acid sequence as defined above with the N-terminal leader sequence of SEQ ID NO: 32. The amino acid sequence of a TCR-CAR first polypeptide consisting of the amino acid sequence set forth in SEQ ID NO: 47 and the leader sequence of SEQ ID NO: 31 is set forth in SEQ ID NO: 60; the amino acid sequence of a TCR-CAR second polypeptide consisting of the amino acid sequence set forth in SEQ ID NO: 48 and the leader sequence of SEQ ID NO: 32 is set forth in SEQ ID NO: 61.

In other embodiments the leader may be a leader other than SEQ ID NO: 31 or 32 or a variant thereof, as discussed above.

The TCR-CAR may be encoded as a single chain. As described above, the first polypeptide may be located at the N-terminus of the single chain or the second polypeptide may be located at the N-terminus of the single chain. The first and second polypeptide may be joined by a linker, as described above. Preferably the first and second polypeptide are joined by a 2A linker, such as that with the amino acid sequence set forth in SEQ ID NO: 18.

In particular embodiments, the TCR-CAR is encoded as a single chain comprising or consisting of the amino acid sequence set forth in SEQ ID NO: 49 or SEQ ID NO: 50, or a variant of SEQ ID NO: 49 or SEQ ID NO: 50. A variant of SEQ ID NO: 49 or SEQ ID NO: 50 has an amino acid sequence with at least 95%, 96%, 97%, 98% or 99% sequence identity to SEQ ID NO: 49 or SEQ ID NO: 50, with the proviso that the CDR sequences are as defined above. Preferably a variant of SEQ ID NO: 49 or SEQ ID NO: 50 comprises the above-described cysteine residue at position 49 of the constant region of an α-chain, or a position corresponding to position 49 of the constant region of an α-chain, and the above-described cysteine residue at position 57 of the constant region of a β-chain, or a position corresponding to position 57 of the constant region of a β-chain.

SEQ ID NO: 49 consists of, from N-terminus to C-terminus, a first polypeptide of SEQ ID NO: 60, the 2A peptide of SEQ ID NO: 18 and a second polypeptide of SEQ ID NO: 26. SEQ ID NO: 50 consists of, from N-terminus to C-terminus, a first polypeptide of SEQ ID NO: 24, the 2A peptide of SEQ ID NO: 18 and a second polypeptide of SEQ ID NO: 61.

In another embodiment, the nucleic acid molecule encodes a specific binding molecule as described above, comprising a first polypeptide which comprises a truncated constant region of an α-chain and a second polypeptide which comprises a truncated region of a β-chain, in which the specific binding molecule is a TCR-antibody construct.

A TCR-antibody construct is a protein comprising a soluble first polypeptide and a soluble second polypeptide as described above, joined to one of which is the Fc region of an antibody. The first and second polypeptides are joined, preferably covalently. Covalent joining of the first and second polypeptides may be achieved via one or more disulphide bonds. To this end, one or more cysteine resides may be introduced into the truncated TCR chain constant regions of the first and second polypeptides, as discussed above.

A TCR-antibody construct binds an antigen-MHC complex on a target cell as is detailed above. The Fc region of the TCR-antibody construct is bound by an Fc receptor. Fc receptors are expressed by a number of human immune effector cells, including B-cells, NK cells, dendritic cells, macrophages, etc. Recruitment of such cells to target cells by the TCR antibody construct may initiate target cell killing by cytotoxic cells and a broader immune response against the target cells.

A TCR-antibody construct may comprise two antigen-binding sites. As is known to the skilled person, an antibody comprises two heavy chains and two light chains. The two heavy chains comprise three constant domains ($C_H1$ to $C_H3$). The $C_H1$ and $C_H2$ domains are separated by a flexible hinge region. In an antibody the two heavy chains are covalently joined by disulphide bonds formed between cysteine residues located within the hinge regions. The Fc region of an antibody heavy chain comprises the $C_H2$ and $C_H3$ domains, and may also comprise the hinge domain. In a TCR-antibody construct in which the Fc region comprises the hinge domain, the polypeptide comprising the antibody Fc region will dimerise via covalent bonds in the hinge domain. Thus a TCR-antibody construct may be a dimeric specific binding molecule, comprising two first polypeptides and two second polypeptides and thus two antigen-binding sites.

The antibody Fc region may be attached to the first polypeptide or the second polypeptide. The Fc region is located at the C-terminus of the designated polypeptide, C-terminal to the truncated TCR constant region.

Fc regions differ between antibody isotypes (and indeed isotype classes). By "differ" is meant that the Fc regions have different sequences. Fc regions also differ between species. Thus for instance, the Fc region of a given human antibody isotype, e.g. IgG1, has a different sequence to the Fc region of an IgG1 antibody of a different species (e.g. a murine IgG1 antibody). A human IgG1 Fc region also has a different sequence to the Fc region of a human antibody of a different isotype (e.g. a human IgA antibody) and a human antibody of a different class of the same isotype (e.g. a human IgG2 antibody). The Fc region of the TCR-antibody construct encoded by the nucleic acid molecule disclosed herein is preferably a human Fc region, i.e. the Fc region of a human antibody. The Fc region is most preferably the Fc region of a human IgG antibody, e.g. the human IgG1, IgG2, IgG3 or IgG4 antibody. The human IgG1 heavy chain constant region has the UniProt accession number P01857; the human IgG2 heavy chain constant region has the UniProt accession number P01859; the human IgG3 heavy chain constant region has the UniProt accession number P01860; the human IgG4 heavy chain constant region has the UniProt accession number P01861. Each UniProt entry contains details of the location of each domain within the constant region, rendering the sequence of the Fc regions easily derivable from the UniProt entries.

Each chain of the TCR-antibody construct is encoded with an N-terminal leader sequence. The N-terminal leader sequences may be as discussed above. The first and second polypeptides may also be encoded as a single chain separated by a linker, preferably a self-splicing linker, as detailed above.

The first or second polypeptide of the TCR-antibody construct may be encoded with a C-terminal affinity tag, for the purposes of purification of the construct. Such affinity tags are discussed above.

As detailed above, the nucleic acid molecule disclosed herein may encode a specific binding molecule comprising a first polypeptide comprising a variable region of an α-chain and a second polypeptide comprising a variable region of a β-chain, in which the specific binding molecule is encoded as a single chain comprising the first polypeptide linked to the second polypeptide. In a particular such embodiment, the specific binding molecule encoded by the nucleic acid molecule disclosed herein is a chimeric TCR.

Chimeric TCRs are similar to TCR-CARs and are described in WO 2000/031239. A chimeric TCR comprises a single-chain TCR variable region (scFv-TCR) a transmembrane domain and one or more intracellular signalling domains. The transmembrane domain and intracellular signalling domain(s) constitute a CAR signalling tail, corresponding to that used in the TCR-CARs. A chimeric TCR may be used equivalently to a TCR-CAR, i.e. it may be expressed in an immune effector cell to redirect the cell against a target antigen.

The scFv-TCR comprises a variable region of an α-chain as described above and a variable region of a β-chain as described above. The signalling tail of the chimeric TCR may be as defined with respect to the TCR-CAR, above. The chimeric TCR comprises, in order from N-terminus to C-terminus, the scFv-TCR, the transmembrane domain and the one or more intracellular signalling domains.

In the scFv-TCR, the variable region of an α-chain may be joined to the variable region of a β-chain by a linker. In this instance the linker is not self-splicing. Preferably it does not contain a protease cleavage site or any other cleavage site. Appropriate linkers are known to the skilled person. An exemplary linker is a $G_4S$ linker. $G_4S$ linkers comprise repeating units of four glycine residues followed by a serine residue (i.e. repeats of the sequence motif Gly-Gly-Gly-Gly-Ser (SEQ ID NO: 67)). The skilled person is able to select a $G_4S$ linker with an appropriate number of repeats, e.g. 3 or 4 repeats. In the scFv-TCR the variable region of an α-chain may be located N-terminal to the variable region of the β-chain, or the variable region of the β-chain may be located N-terminal to the variable region of an α-chain. The scFv-TCR is preferably encoded with a single N-terminal leader sequence, which directs the chimeric TCR to the cell membrane.

The chimeric TCR may further comprise a constant region of an α-chain or a constant region of a β-chain. The constant region of a TCR chain is located between the scFv-TCR and the transmembrane domain, i.e. C-terminal of the scFv-TCR and N-terminal of the transmembrane domain. The constant region of a TCR chain is C-terminally truncated as described above, and so does not comprise a transmembrane domain or intracellular domain. The truncated constant region may be a truncated constant region of an α-chain, and in particular may comprise or consist of the amino acid sequence set forth in SEQ ID NO: 29, or a variant thereof. The truncated constant region may be a truncated constant region of a β-chain, and in particular may comprise or consist of the amino acid sequence set forth in SEQ ID NO: 30, or a variant thereof. If the chimeric TCR comprises a constant region of a TCR chain, it preferably comprises only a single constant region of a TCR chain, i.e. a constant region of an α-chain or a constant region of a β-chain, not a constant region of an α-chain and a constant region of a β-chain.

The nucleotide sequence of the hTERT-TCR-1 α-chain is set forth in SEQ ID NO: 62, and the nucleotide sequence of the hTERT-TCR-1 β-chain is set forth in SEQ ID NO: 63. It would be straightforward for the skilled person, based on the information provided herein, to identify the regions within the native DNA sequences which encode the various parts of the TCR chains. The nucleotide sequence of the 2A self-splicing peptide is set forth in SEQ ID NO: 64. However, it will be appreciated by those of ordinary skill in the art that, as a result of the degeneracy of the genetic code, there are many nucleotide sequences that may encode each individual specific binding molecule as described herein, in addition to the native sequences.

The nucleic acid molecule disclosed herein may be an isolated nucleic acid molecule and may include DNA (including cDNA) or RNA or chemical derivatives of DNA or RNA, including molecules having a radioactive isotope or a chemical adduct such as a fluorophore, chromophore or biotin ("label"). Thus the nucleic acid may comprise modified nucleotides. Said modifications include base modifications such as bromouridine, ribose modifications such as arabinoside and 2', 3'-dideoxyribose and internucleotide linkage modifications such as phosphorothioate, phosphorodithioate, phosphoroselenoate, phosphorodiselenoate, phosphoroanilothioate, phosphoraniladate and phosphoroamidate. The term "nucleic acid molecule" specifically includes single- and double-stranded forms of DNA and RNA. "Isolated", as used herein, means that the species in question is the primary component (i.e. majority component) of any solution or suchlike in which it is provided.

Methods for constructing nucleotide sequences as defined herein, and for modifying nucleotide sequences to introduce changes to the amino acid sequences of the various specific binding molecule sequences are well known in the art, e.g. methods of mutagenesis, such as site-specific mutagenesis, may be employed. Methods for preparing a nucleic acid molecule encoding the specific binding molecule include e.g. conventional polymerase chain reaction (PCR) cloning techniques.

For instance, the nucleic acid molecule can be cloned into a general purpose cloning vector such as pENTR™ (Gateway), pUC19, pBR322, pBluescript™ vectors (Stratagene Inc.) or pCR TOPO® from Invitrogen Inc. The resultant nucleic acid construct (recombinant vector) carrying the nucleic acid molecule encoding the specific binding molecule can then be sub-cloned into expression vectors or viral vectors for protein expression, e.g. in mammalian cells. This may be for preparation of the specific binding molecule, or for expression in immune effector cells e.g. human T-cells or cell lines or other human immune effector cells. Further, the nucleic acid may be introduced into mRNA expression vectors for production of mRNA encoding the specific binding molecule. The mRNA may then be transferred into immune effector cells.

Methods for isolation of nucleic acid molecules are also well known in the art. For instance, DNA may be isolated using a suitable kit. Plasmid DNA may be isolated from bacteria using a Miniprep or Maxiprep kit according to the manufacturer's instructions. Such kits are available from e.g. Qiagen (Germany). Genomic DNA may be extracted from eukaryotic or prokaryotic cells using e.g. a QIAamp™ DNA Mini Kit (Qiagen) or a DNeasy™ kit (Qiagen) according to the manufacturer's instructions. Alternatively, traditional methods of phenol-chloroform extraction may be used to isolate DNA from cells of interest. Such traditional methods are well known in the art.

As detailed above, the nucleic acid molecule provided herein may comprise variants of the specific binding molecule sequences of the disclosure. When the nucleic acid molecule encodes a specific binding molecule comprising a "variant" as defined above, the variant is a functional variant. A "functional variant" as defined herein is a sequence which is modified relative to the native or defined reference sequence, as detailed above, but which retains the function of the reference sequence, i.e. the modification does not disrupt the functionality of the specific binding molecule.

Thus for instance a variant of a variable region of a TCR chain retains the ability of the native TCR chain to bind a target antigen, and a specific binding molecule comprising the variant variable region is able to bind the target antigen and activate downstream signalling pathways. Similarly, a variant of a constant region of a TCR chain does not inhibit the ability of a specific binding molecule comprising the variant constant region to bind a target and activate downstream signalling pathways. Variants of the 2A self-splicing peptide are discussed above. Variants of transmembrane domains and intracellular signalling domains retain the activity and essential structural features of the native domains, e.g. interactions with signalling partners etc. are not inhibited.

A variant may be tested for functionality by testing the activity of a specific binding molecule comprising a variant sequence against an otherwise equivalent specific binding molecule comprising the corresponding native sequence. As noted above, a functional variant sequence retains the function of the corresponding unmodified sequence. A functional variant sequence may retain at least 60% of the activity of the corresponding unmodified sequence, preferably at least 65, 70, 75, 80, 85, 90, 95, or 100% of the activity of the unmodified sequence. Specific binding molecule functionality may be analysed by any method known in the art. Such methods are known to the skilled person and are demonstrated in the Examples below. For instance, the activity of soluble specific binding molecules may be tested by analysing the binding of the molecules to their target, using e.g. surface plasmon resonance or thermal fluctuation assay. The activity of non-soluble specific binding molecules may be analysed by testing their ability to activate effector functions of cells expressing them. Such specific binding molecules may be tested in e.g. functional assays in which cytokine release or target cell killing in response to exposure to the antigen is measured. Such assays are demonstrated in the Examples below.

Variant sequences are defined according to their sequence identity with reference sequences. Sequence identity may be assessed by any convenient method. However, for determining the degree of sequence identity between sequences, computer programmes that make pairwise or multiple alignments of sequences are useful, for instance, as discussed above, EMBOSS Needle or EMBOSS stretcher may be used for pairwise sequence alignments while Clustal Omega or MUSCLE may be used for multiple sequence alignments, though any other appropriate programme may be used. Whether the alignment is pairwise or multiple, it must be performed globally (i.e. across the entirety of the reference sequence) rather than locally. Suitable parameters for use in sequence alignments are discussed above.

In another aspect, the disclosure provides a recombinant construct comprising the nucleic acid molecule described herein linked to a heterologous nucleic acid sequence. By "heterologous" as used herein is meant a nucleic acid sequence which is not natively linked to the nucleic acid molecule described herein, i.e. which is not linked to the nucleic acid molecule described herein in nature. In the construct, the nucleic acid molecule described herein may be flanked by restriction sites (i.e. nucleotide sequences recognised by one or more restriction enzymes) to enable easy cloning of the nucleic acid molecule of the invention. A "recombinant" construct is a nucleic acid construct synthesised using recombinant techniques, e.g. molecular cloning.

The term "linked" as used herein with respect to the construct may simply mean that the nucleic acid molecule is directly joined to a heterologous nucleic acid sequence. In a preferred embodiment, in the recombinant construct the nucleic acid molecule disclosed herein is operatively linked to a heterologous expression control sequence (i.e. preferably the term "linked" means "operatively linked").

The term "expression control sequence" refers to nucleotide sequences located upstream of (5' non-coding sequences), within, or downstream (3' non-coding sequences) of a coding sequence, and which influence transcription, RNA processing or stability, or translation of the associated coding sequence (i.e. which influence any aspect of expression of the encoded specific binding molecule). Expression control sequences, as defined herein, refer particularly to cis-regulatory elements. Expression control sequences include promoters, promoter elements such as a TATA box or a B recognition element, operators, enhancers, translation leader sequences, terminator sequences and suchlike. As used herein, the term "promoter" refers to a nucleotide sequence capable of controlling the expression of a coding sequence or RNA. Suitable examples are provided hereinafter. In general, a coding sequence is located 3' to a promoter sequence. Promoters may be derived in their entirety from a native gene, or be composed of different elements derived from different promoters found in nature, or even comprise synthetic nucleotide segments. It is further recognised that since in most cases the exact boundaries of regulatory sequences have not been completely defined, nucleic acid fragments of different lengths may have identical regulatory activity.

In the construct, the nucleic acid molecule disclosed herein may be operatively linked to one or more heterologous expression control sequences. The nucleic acid molecule disclosed herein is typically operatively linked to at least a promoter. Suitable promoter sequences include the cytomegalovirus (CMV) promoter, particularly the human CMV (HCMV) promoter, the PGK promoter, the EF1a promoter, the constitutive simian virus 40 (SV40) early promoter, the mouse mammary tumour virus (MMTV) promoter, the HIV LTR promoter, the MoMuLV promoter, the avian leukaemia virus promoter, the EBV immediate early promoter, and the Rous sarcoma virus promoter. Human gene promoters may also be used, including, but not limited to, the actin promoter, the myosin promoter, the haemoglobin promoter, and the creatine kinase promoter. In certain embodiments inducible promoters may be used. These provide a molecular switch capable of turning expression of the nucleic acid molecule on or off. Examples of inducible promoters include, but are not limited to, a metallothionine promoter, a glucocorticoid promoter, a progesterone promoter, or a tetracycline promoter. The skilled person is able to select a suitable promoter to use to drive expression of the encoded specific binding molecule, depending on e.g. the cell type in which it is to be expressed and the purpose of the expression.

The term "operably linked" refers to the association of two or more nucleic acid molecules on a single nucleic acid fragment so that the function of one is affected by the other. For example, a promoter is operably linked to a coding sequence when it is capable of affecting the expression of that coding sequence (i.e. the coding sequence is under the transcriptional control of the promoter). Coding sequences may be operably linked to regulatory sequences in sense or antisense orientation.

Methods for preparing a construct as provided herein are well known in the art, e.g. conventional polymerase chain reaction (PCR) cloning techniques can be used as described to synthesise the nucleic acid molecule disclosed herein, which may be inserted into suitable constructs (e.g. those containing a heterologous expression control sequence) using known methods, e.g. cloning using restriction enzymes or Gibson assembly.

In another aspect, the disclosure provides a vector comprising the nucleic acid molecule or recombinant construct described herein. The term "vector" as used herein refers to a vehicle into which the nucleic acid molecule or construct of the invention may be introduced (e.g. be covalently inserted) from which the specific binding molecule encoded by the disclosed nucleic acid molecule may be expressed and/or the nucleic acid molecule/construct cloned. The vector may accordingly be a cloning vector or an expression vector.

The nucleic acid molecule or construct of the invention may be inserted into a vector using any suitable methods known in the art, for example, without limitation, the vector and nucleic acid molecule may be digested using appropriate restriction enzymes and then may be ligated with the nucleic acid molecule having matching sticky ends, or as appropriate the digested nucleic acid molecule may be ligated into the digested vector using blunt-ended cloning.

Examples of vectors include plasmids, autonomously replicating sequences and transposable elements. Additional exemplary vectors include, without limitation, phagemids, cosmids, artificial chromosomes such as a yeast artificial chromosome (YAC), a bacterial artificial chromosome (BAC) or a P1-derived artificial chromosome (PAC), bacteriophages such as lambda phage or M13 phage, and animal viruses, particularly human viruses (i.e. viral vectors). Examples of categories of animal viruses useful as vectors include, without limitation, retroviruses (including lentiviruses), adenoviruses, adeno-associated viruses, herpesviruses (e.g. herpes simplex virus), poxviruses, baculoviruses, papillomaviruses and papovaviruses (e.g. SV40). Examples of expression vectors are pCl-neo vectors (Promega) for expression in mammalian cells and pLenti4/V5-DEST™ and pLenti6/V5-DEST™ for lentivirus-mediated gene transfer and expression in mammalian cells.

The vector may be a bacterial or prokaryotic vector (i.e. a vector for use, e.g. cloning or expression, in bacterial or prokaryotic cells) or a eukaryotic vector (i.e. a vector for use in mammalian cells), particularly a mammalian vector. The nucleic acid molecule or construct of the invention may be produced in or introduced into a general purpose cloning vector, particularly a bacterial cloning vector, e.g. an *Escherichia coli* cloning vector. Typically a cloning vector is a bacterial plasmid, particularly an *E. coli* plasmid. Examples of such cloning vectors include pUC19 (available from e.g. New England Biolabs (NEB), USA), pBR322 (also available from NEB), pBluescript vectors (Agilent, USA) and pCR TOPO® vectors from Thermo Fisher Scientific, e.g. pCR2.1-TOPO.

The nucleic acid molecule or construct of the invention may be sub-cloned into an expression vector for expression of the specific binding molecule of the invention, particularly a mammalian expression vector. Expression vectors can contain a variety of expression control sequences.

The expression vector should have the necessary 5' upstream and 3' downstream regulatory elements such as promoter sequences (discussed above in the context of the construct of the disclosure), including a TATA box, a Kozak sequence at the translation start site, and the 3' UTR AATAAA polyadenylation signal sequence to signal transcription termination, for efficient gene transcription and translation in its respective host cell. Further, the expression vector may contain 5' and 3' untranslated regulatory sequences that function as enhancer sequences that can facilitate or enhance efficient transcription of the nucleic acid molecule.

In addition to control sequences that govern transcription and translation, vectors may contain additional nucleic acid sequences that serve other functions, including for example vector replication, selectable markers etc. Examples of selectable markers particularly suitable for selection of bacterial host cells include antibiotic resistance genes, such as an ampicillin resistance gene (e.g. β-lactamase), a kanamycin resistance gene or a chloramphenicol resistance gene (e.g. chloramphenicol acetyl transferase). Selectable markers particularly suitable for use in mammalian host cells include hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene. Such selectable markers allow the in vitro selection of cells carrying the vector.

The vector may comprise a marker which renders immune effector cells carrying the vector susceptible to negative selection in vivo. The inclusion of such a marker allows the selective destruction of immune effector cells carrying the vector in an individual to whom such cells have been administered, e.g. a patient treated using adoptive cell therapy. This may be important if e.g. the patient experiences severe side-effects to treatment. The negatively selectable phenotype may result from the insertion of a gene that confers sensitivity to an administered agent, for example, a compound. Negatively selectable genes are known in the art, and include, inter alia, the following: the Herpes simplex virus type I thymidine kinase (HSV-I TK) gene (Wigler et al., Cell 11 (1):223-232, 1977) which confers ganciclovir sensitivity; and bacterial cytosine deaminase, which confers 5-fluorocytosine sensitivity (Mullen et al., Proc. Natl. Acad. Sci. USA. 89:33-37 (1992)). A vector disclosed herein may therefore comprise such a gene. Alternatively a vector may comprise a gene encoding a non-native membrane protein to enable targeting of immune effector cells carrying the vector using an antibody. Suitable markers for positive and/or negative selection are known to and may be selected by the skilled person.

In an embodiment, the vector comprises both a marker for positive selection and a marker for negative selection. Preferably, the positively selectable marker and the negatively selectable element are linked such that loss of the negatively selectable element necessarily also is accompanied by loss of the positively selectable marker. Even more preferably, the positively and negatively selectable markers are fused, so that loss of one obligatorily leads to loss of the other. An example of a fused polynucleotide that yields as an expression product a polypeptide that confers both the desired positive and negative selection features described above is a hygromycin phosphotransferase-thymidine kinase fusion gene (HyTK). Expression of this gene yields a polypeptide that confers hygromycin B resistance for positive selection in vitro, and ganciclovir sensitivity for negative selection in vivo. (See Lupton S. D., et al, Mol. and Cell. Biology 11:3374-3378, 1991.)

In certain embodiments, viral vectors are preferred. A viral vector may be derived from a retrovirus, particularly a lentivirus or a spumavirus/foamyvirus. As used herein, the term "viral vector" refers to a virus-derived particle which carries the nucleic acid molecule or construct disclosed herein, and is able to deliver the nucleic acid molecule/construct to a target cell. The viral vector can contain the nucleic acid molecule of the invention in place of nonessential viral genes, or in addition to the native viral genes. The vector can be utilized for the purpose of transferring DNA, RNA or other nucleic acids into cells either in vitro or ex vivo.

Numerous forms of viral vectors are known in the art, and any suitable viral vector may be used according to the present teaching, including both single-stranded and double-stranded RNA viral vectors and DNA viral vectors. Single-stranded viral vectors may be positive-sense or negative-sense viral vectors. In certain embodiments, the viral vector is a retroviral vector (i.e. a viral vector derived from a retrovirus), in particular a lentiviral vector (i.e. a viral vector derived from a lentivirus). Retroviruses are single-stranded positive-sense RNA viruses, which integrate their genomes into the genome of an infected host cell. Lentiviruses are a group (or genus) of retroviruses that give rise to slowly-developing disease. Viruses included within this group include HIV (human immunodeficiency virus; including HIV type 1, and HIV type 2). Because retroviral genomes integrate into the genome of an infected cell, a retroviral vector as described herein can be used to stably transduce a target cell, i.e. permanently alter the genetic make-up of a target cell.

The viral vector may be a self-inactivating vector or replication-deficient vector. Replication-deficient vectors are known in the art. Replication-deficient retroviral vectors can be obtained by e.g. modification (e.g. deletion or substitution) of the 3' LTR enhancer-promoter region, known as the U3 region, of the viral genome to prevent viral transcription beyond the first round of viral replication. Consequently, the vectors are capable of infecting and then integrating into the host genome only once, and cannot be passed further.

The retroviral vectors for use herein can be derived from any known retrovirus, e.g. Type C retroviruses, such as Moloney murine sarcoma virus (M-MSV), Harvey murine sarcoma virus (Ha-MuSV), mouse mammary tumour virus (MMTV), gibbon ape leukaemia virus (GaLV), feline leukaemia virus (FLV), spumaviruses, Friend virus, murine stem cell virus (MSCV) and Rous sarcoma virus (RSV); human T-cell leukaemia viruses such as HTLV-1 and HTLV-2; and the lentiviral family of retroviruses, such as the human immunodeficiency viruses HIV-1 and HIV-2, simian immunodeficiency virus (SIV), feline immunodeficiency virus (FIV), equine immunodeficiency virus (EIV), and other classes of retroviruses.

A retroviral packaging cell line (typically a mammalian cell line) may be used to produce viral vectors, which may then be used for transduction of T-cells. A packaging cell line may be used to produce a viral vector by transfection with one or more vectors (e.g. plasmids) which carry the necessary genes for viral particle assembly. The skilled person is able to produce a viral vector without particular instruction. Illustrative viral vectors are described in WO 2002/087341, WO 2002/083080, WO 2002/082908, WO 2004/000220 and WO 2004/054512. An exemplary plasmid for the production of a retroviral vector is pMP71, as described in Wälchli et al 2011. Other suitable plasmids include pBABE, pWZL, pMCs-CAG, pMXs-CMV, pMXs-EF1α, pMXs-IRES, pMXs-SRα and pMYs-IRES.

An mRNA vector is a positive-sense mRNA strand comprising the nucleic acid molecule or construct described above. An mRNA vector is a translatable mRNA strand which, upon delivery to a target cell, can bind a ribosome and initiate synthesis of the encoded protein. An mRNA vector is advantageous as it does not require nuclear entry or transcription in order to initiate production of its encoded protein, but can instead directly bind a cytoplasmic ribosome and initiate translation. Transfection of a target cell with an mRNA vector can thus be used for rapid production of the encoded specific binding molecule. RNA has only a limited half-life due to its inherent instability, and thus an mRNA vector may be used for transient transfection of a target cell.

An mRNA vector comprises the essential elements for translation, e.g. a 5' 7-methylguanylate cap for ribosomal recognition and a polyadenylate tail. An mRNA vector can be produced from an mRNA expression vector using a cellular system according to methods known in the art. Suitable mRNA expression vectors include pCIpA102, Sæbøe-Larssen et al., 2002, *J. Immunol. Methods* 259: 191-203 and pCIpA120-G, Wälchli et al., 2011, PLoS ONE 6(11): e27930). Alternatively an mRNA vector can be produced using a cell-free system, e.g. by in vitro transcription. Such systems are well-known in the art, require a DNA template comprising the gene to be transcribed and a suitable promoter, and utilise an RNA polymerase, generally a phage RNA polymerase. Kits for the performance of in vitro transcription may be obtained from e.g. Thermo Fisher Scientific (e.g. the MEGAscript™ SP6 Transcription Kit).

In another aspect, the disclosure provides a host cell comprising a nucleic acid molecule, construct or vector as described above. The encoded specific binding molecule is heterologous to the host cell. That is to say, the encoded specific binding molecule is not natively (i.e. in nature) expressed by the host cell. Such a host cell may be any suitable host, including a cloning host, a production host or an immune effector cell. The host cell may be derived from any species, and indeed any domain of life, as appropriate for its function. For instance, the host cell may be a prokaryotic (e.g. bacterial) or eukaryotic (e.g. mammalian) cell.

The nucleic acid molecules, constructs or vectors may be introduced into a host cell using any appropriate technique known in the art. Appropriate techniques for the introduction of a nucleic acid molecule, construct or vector into a prokaryotic cell include transformation, transduction and conjugation. Transformation refers to the genetic alteration of a competent bacterium by direct uptake of DNA. Transduction refers to infection of a bacterium using a bacteriophage in order to introduce DNA of interest. Conjugation refers to the direct transfer of genetic material between bacterial cells in direct contact. Methods for the performance of these procedures are well-known in the art.

A nucleic acid molecule, construct or vector is introduced into a eukaryotic cell by transfection. The term "transfection" refers to the process by which an exogenous nucleic acid molecule is introduced into a host eukaryotic (particularly animal) cell. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, transduction and biolistics. Transduction refers to the delivery of a nucleic acid molecule using a viral vector by means of viral infection of the target cell.

The nucleic acid molecule, construct or vector may be integrated into the genome of the host cell or may be maintained extra-chromosomally. The nucleic acid may be maintained transiently in the host cell or may be stable.

A prokaryotic cell may in particular be used as a cloning host for the nucleic acid molecule, construct or vector described above. Suitable prokaryotic cells for use as cloning hosts include, without limitation, eubacteria, such as Gram-negative or Gram-positive organisms, for example, Enterobacteriaceae such as *Escherichia*, in particular *E. coli*, and Bacilli such as *B. subtilis*. A cloning host may alternatively be a eukaryotic cell such as a fungal cell, e.g. *Pichia pastoris*, or a yeast cell, or even a higher eukaryotic cell such as a mammalian cell. The skilled person is able to select a suitable cloning host without particular instruction. Suitable cloning hosts may be commercially obtained, e.g. competent *E. coli* cells are available from NEB (NEB 5-alpha) and Thermo Fisher Scientific (One Shot™ TOP10). Alternatively, cloning hosts may be obtained via culture using techniques known to the skilled person.

In a particular embodiment, the host cell is an immune effector cell and the nucleic acid molecule, construct or vector encodes a specific binding molecule which comprises a transmembrane domain (e.g. it may be a full-length TCR, a TCR-CAR or a chimeric TCR). An immune effector cell is defined above. As described, representative immune effector cells include T-cells, in particular cytotoxic T-cells (CTLs; CD8+ T-cells) and helper T-cells (HTLs; CD4+ T-cells) and NK cells. Other populations of T-cells are also useful herein, for example naïve T-cells and memory T-cells. Other immune effector cells include NKT-cells, neutrophils and macrophages.

The term "immune effector cell" as used herein includes not only mature or fully differentiated immune effector cells but also precursor (or progenitor) cells therefor, including stem cells (more particularly haematopoietic stem cells, HSC), or cells derived from HSC. An immune effector cell may accordingly be a cell derived from HSCs contained within the CD34+ population of cells derived from a haematopoietic tissue, e.g. from bone marrow, cord blood, or blood e.g. mobilised peripheral blood, which upon administration to a subject differentiate into mature immune effector cells or which can be induced to differentiate into immune effector cells in vivo or in vitro.

The immune effector cell preferably expresses the encoded specific binding molecule on its surface. By "expression" of the encoded specific binding molecule is meant that the gene, i.e. the nucleotide sequence which encodes the specific binding molecule, is transcribed and translated so as to produce the encoded specific binding molecule. Expression of the nucleic acid molecule may be constitutive or inducible, depending on the promoter used to drive expression of the gene. It is straightforward for the skilled person to express a gene in a host cell, though it may be necessary for expression conditions to be optimised. This is well within the ability of the skilled person. When the immune effector cell expresses the encoded specific binding molecule on its surface, the specific binding molecule is active. Immune effector cells expressing the encoded specific binding molecule on their surface may be identified and isolated using e.g. flow cytometry.

T-cells and NK cells represent preferred host immune effector cells. The T-cell can be any T-cell. It may be a cytotoxic T-cell (a $CD8^+$ T-cell), a helper T-cell (a $CD4^+$ T-cell), a naïve T-cell, a memory T-cell or any other type of T-cell. Preferably the T-cell is a $CD4^+$ or $CD8^+$ T-cell. As defined herein, a T-cell of the invention may also be an immature T-cell, such as a $CD4^-/CD8^-$ cell or a $CD4^+/CD8^+$ cell, or a progenitor of a T-cell.

The term "NK cell" refers to a large granular lymphocyte, being a cytotoxic lymphocyte derived from the common lymphoid progenitor which does not naturally comprise an antigen-specific receptor (e.g. a T-cell receptor or a B-cell receptor). Naturally occurring NK cells may be characterised by their $CD3^-$, $CD56^+$ phenotype when assayed by anti-CD3ε or anti-CD3δ antibodies and anti-CD56 antibodies. The term as used herein thus includes any known NK cell or any NK-like cell or any cell having the characteristics of an NK cell. Thus primary NK cells may be used or, in an alternative embodiment, an NK cell known in the art that has previously been isolated and cultured may be used. Thus an NK cell line may be used. A number of different NK cells are known and reported in the literature and any of these could be used, or a cell line may be prepared from a primary NK cell, for example by viral transformation (Vogel et al. 2014, Leukemia 28:192-195). Suitable NK cells include (but are by no means limited to), the NK-92, NK-YS, NK-YT, MOTN-1, NKL, KHYG-1, HANK-1 and NKG cell lines. The cell may in particular be an NK-92 cell (Gong et al. 1994, Leukemia 8:652-658), or a variant thereof. A number of different variants of the original NK-92 cells have been prepared and are described or available, including NK-92 variants which are non-immunogenic. Any such variants can be used and are included in the term "NK-92". Variants of other cell lines may also be used.

WO 2016/116601 describes how a TCR may be functionally expressed in an NK cell. As detailed therein, a TCR may in particular be functionally expressed in an NK cell if it is co-expressed with CD3 chains.

An immune effector cell as disclosed herein is preferably human. Such an immune effector cell may be derived from any human individual. Preferably, when the immune effector cell is for therapeutic use, it is an autologous immune effector cell: i.e. it is derived from the patient to be treated, which ensures histocompatibility and non-immunogenicity, meaning once genetically modified, it will not induce an immune response from the patient. Where the immune effector cell is a non-autologous cell for therapeutic use (i.e. it is a donor cell obtained from an individual other than the patient) it is preferred that it is non-immunogenic, such that it does not, when administered to a subject, generate an immune response which affects, interferes with, or prevents the use of the cells in therapy. A host immune effector cell as disclosed herein may thus be an ex vivo cell. It may alternatively or also be an in vitro cell.

Non-autologous immune effector cells may be naturally non-immunogenic if they are HLA-matched to the patient, i.e. they express the same HLA alleles. Non-autologous immune effector cells, including those which are not HLA-matched to the patient and would therefore be immunogenic, and those which are HLA-matched to the patient and may not be immunogenic, may be modified to eliminate expression of MHC molecules, or to only weakly express MHC molecules at their surface. Alternatively, such cells may be modified to express non-functional MHC molecules.

Any means by which the expression of a functional MHC molecule is disrupted is encompassed. Hence, this may include knocking out or knocking down a molecule of the MHC complex, and/or it may include a modification which prevents appropriate transport to and/or correct expression of an MHC molecule, or of the whole complex, at the cell surface.

In particular, the expression of one or more functional MHC class-I proteins at the surface of an immune effector cell of the invention may be disrupted. In one embodiment the immune effector cells may be human cells which are HLA-negative, such as cells in which the expression of one or more HLA molecules is disrupted (e.g. knocked out), e.g. molecules of the HLA Class I MHC complex.

In a preferred embodiment, disruption of Class-I MHC expression may be performed by knocking out the gene encoding $\beta_2$-microglobulin ($\beta_2$-m), a component of the mature Class-I MHC complex. Expression of $\beta_2$-m may be eliminated through targeted disruption of the $\beta_2$-m gene, for instance by site-directed mutagenesis of the $\beta_2$-m promoter (to inactivate the promoter), or within the gene encoding the $\beta_2$-m protein to introduce an inactivating mutation that prevents expression of the $\beta_2$-m protein, e.g. a frame-shift mutation or premature 'STOP' codon within the gene. Alternatively, site-directed mutagenesis may be used to generate non-functional $\beta_2$-m protein that is not capable of forming an active MHC protein at the cell surface. In this manner the $\beta_2$-m protein or MHC may be retained intracellularly, or may be present but non-functional at the cell surface.

Immune effector cells may alternatively be irradiated prior to being administered to a subject. Without wishing to be bound by theory, it is thought that the irradiation of cells results in the cells only being transiently present in a subject, thus reducing the time available for a subject's immune system to mount an immunological response against the cells. Whilst such cells may express a functional MHC molecule at their cell surface, they may also be considered to be non-immunogenic. Radiation may be from any source of $\alpha$, $\beta$ or $\gamma$ radiation, or may be X-ray radiation or ultraviolet light. A radiation dose of 5-10 Gy may be sufficient to abrogate proliferation, however other suitable radiation doses may be 1-10, 2-10, 3-10, 4-10, 6-10, 7-10, 8-10 or 9-10 Gy, or higher doses such as 11, 12, 13, 14, 15 or 20 Gy. Alternatively, the cells may be modified to express a 'suicide gene', which allows the cells to be inducibly killed or prevented from replicating in response to an external stimulus.

Thus, an immune effector cell according to the invention may be modified to be non-immunogenic by reducing its ability, or capacity, to proliferate, that is by reducing its proliferative capacity.

The host immune effector cells of the invention may also be subject to modification in other ways, for example to alter or modify other aspects of cell function or behaviour, and/or to express other proteins. For instance, the cells may be modified to express a homing receptor, or localisation receptor, which acts to target or improve the localisation of the cells to a particular tissue or location in the body.

A T-cell or NK cell comprising a nucleic acid molecule, construct or vector as described herein may be obtained by transfecting a target T-cell or NK cell. The T-cells or NK cells to be transfected may be derived from an existing cell line, as described above. Alternatively, the T-cells or NK cells to be transfected may be isolated from a subject (who may be a patient to be treated or a donor). In an embodiment, the T-cells or NK cells are isolated from a subject and modified by introduction of the nucleic acid molecule without further manipulation in vitro. Such cells can then be directly administered to a patient. In other embodiments, the T-cells or NK cells are first activated and stimulated to proliferate in vitro (such activation and stimulation to proliferate may be referred to as expansion) before and/or after being modified to express the specific binding molecule. NK cells may be expanded and activated using the methods described in WO 2014/037422.

T-cells can be obtained from a number of sources, including peripheral blood mononuclear cells (PBMCs), bone marrow, lymph node tissue, cord blood, thymus tissue, tissue from a site of infection, ascites, pleural effusion, spleen tissue and tumours. In certain embodiments, T-cells can be obtained from a unit of blood collected from the subject using any number of techniques known to the skilled person, such as FICOLL™ separation. In one embodiment, cells from the circulating blood of a subject are obtained by apheresis. The apheresis product typically contains lymphocytes, including T-cells, monocytes, granulocytes, B-cells, other nucleated white blood cells, red blood cells, and platelets. In one embodiment, the cells collected by apheresis are washed to remove the plasma fraction and to place the cells in an appropriate buffer or medium for subsequent processing. In an embodiment of the invention, the cells are washed with PBS. In an alternative embodiment, the wash solution lacks calcium and/or magnesium or may lack many if not all divalent cations. As would be appreciated by those of ordinary skill in the art, a washing step may be accomplished by methods known to those in the art, such as by using a semiautomated flowthrough centrifuge (for example, the Cobe™ 2991 cell processor, the Baxter CytoMate™ or the like). After washing, the cells may be resuspended in a variety of biocompatible buffers or other saline solution with or without buffer. In certain embodiments, the undesirable components of the apheresis sample may be removed and the cell directly resuspended culture media.

In certain embodiments, T-cells are isolated from PBMCs. PBMCs may be isolated from buffy coats obtained by density gradient centrifugation of whole blood, for instance centrifugation through a LYMPHOPREP™ gradient, a PERCOLL™ gradient or a FICOLL™ gradient. T-cells may be isolated from PBMCs by depletion of the monocytes, for instance by using CD14 DYNABEADS®. In some embodiments, red blood cells may be lysed prior to the density gradient centrifugation.

A specific subpopulation of T-cells, such as CD28$^+$, CD4$^+$, CD8$^+$, CD45RA$^+$ or CD45RO$^+$ T-cells, can, if desired, be further isolated by positive or negative selection techniques. For example, enrichment of a T-cell population by negative selection can be accomplished with a combination of antibodies directed to surface markers unique to the negatively-selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4$^+$ cells by negative selection, a monoclonal antibody cocktail typically includes antibodies to CD14, CD20, CDIIb, CD16, HLA-DR and CD8. Flow cytometry and cell sorting may also be used to isolate cell populations of interest for use in the present invention.

In certain embodiments, both cytotoxic and helper T-cells can be sorted into naïve, memory, and effector T-cell sub-populations either before or after genetic modification and/or expansion. CD8$^+$ or CD4$^+$ T-cells can be obtained by using standard methods as described above. In some embodiments, CD8⁺ and/or CD4⁺ T-cells are further sorted into naive, central memory, and effector cells by identifying cell-surface antigens that are associated with each of those types of T-cell. Memory T-cells may be present in both CD62L⁺ and CD62L⁻ subsets of peripheral blood T-cells. T-cells may be sorted into CD62L⁻/CD8⁺, CD62L⁺/CD8⁺, CD62L⁻/CD4⁺ and CD62L⁺/CD4⁺ fractions after staining with anti-CD8/anti-CD4 and anti-CD62L antibodies. Phenotypic markers of central memory T-cells (TCM) may include expression of CD45RO, CD62L, CCR7, CD28, CD3 and CD127, and lack of expression of granzyme B. TCMs may be CD45RO⁺/CD62L⁺/CD8⁺ or CD45RO⁺/CD62L⁺/CD4⁺ T-cells. Effector T-cells may be negative for CD62L, CCR7, CD28, and CD127 expression, and positive for granzyme B and perforin expression. Naïve CD8⁺ or CD4⁺ T-cells may be characterised by the expression of phenotypic markers of naïve T-cells including CD62L, CCR7, CD28, CD3, CD127 and CD45RA.

Isolated immune effector cells can be modified following isolation, or they can be activated and expanded (or, in the case of progenitors, differentiated) in vitro prior to being modified. In an embodiment, the cells are modified by introduction of the nucleic acid molecule, construct or vector and then are activated and expanded in vitro. In another embodiment, the cells are activated and expanded in vitro then modified by introduction of the nucleic acid molecule, construct or vector. Methods for activating and expanding T-cells are known in the art and are described, for example, in U.S. Pat. Nos. 6,905,874, 6,867,041, 6,797,514, and WO 2012/079000. Generally, such methods include contacting PBMC or isolated T-cells with a stimulatory agent and co-stimulatory agent, such as anti-CD3 and anti-CD28 antibodies, generally attached to a bead or other surface (for instance in the form of CD3/CD28 DYNABEADS®), in a culture medium supplemented with appropriate cytokines, such as IL-2. A bead with both anti-CD3 and anti-CD28 antibodies attached serves as a surrogate antigen presenting cell (APC). In other embodiments, the T-cells may be activated and stimulated to proliferate with feeder cells and appropriate antibodies and cytokines using methods such as those described in U.S. Pat. Nos. 6,040,177, 5,827,642 and WO 2012/129514.

In one embodiment, T-cells are transfected with the nucleic acid molecule, construct or vector, as described above. In another embodiment, CD34⁺ cells are transfected with a nucleic acid molecule, construct or vector, as described above. In certain embodiments, the modified (i.e. transfected) CD34⁺ cells differentiate into mature immune effector cells in vivo following administration into a subject, generally the subject from whom the cells were originally isolated. In another embodiment, CD34⁺ cells may be stimulated in vitro prior to or after transfection, with one or more of the following cytokines: Flt-3 ligand (FL), stem cell factor (SF), megakaryocyte growth and differentiation factor (TPO), IL-3 and IL-6 according to the methods known in the art.

NK cells may be obtained from the same sources as T-cells using standard methods known in the art.

In a particular embodiment the host cell is a production host and the nucleic acid molecule, recombinant construct or vector encodes a soluble specific binding molecule as described above, e.g. a soluble TCR or a TCR-antibody construct. A production host cell is any cell suitable for use in protein production. Appropriate production hosts are known in the art. The production host may be a prokaryote, e.g. an *E. coli* strain optimised for eukaryotic protein production, such as a Rosetta strain. Preferably the production host is a eukaryotic cell, for instance a fungal cell such as a yeast cell, e.g. *Pichia pastoris*. Most preferably the production host is a mammalian cell. The mammalian cell may be a human cell, or a non-human cell. If a non-human mammalian cell is used, the cell is preferably optimised for human protein expression. Suitable mammalian cells include Cos cells, e.g. COS-7 cells, HEK293 cells and CHO cells, though suitable cell line or type may be used. CHO (Chinese hamster ovary) cells are commonly used in the art for protein production, and may be used according to the current disclosure. In a particular embodiment, CHO cells lacking the DHFR (dihydrofolate reductase) gene are transfected with a vector carrying the DHFR gene, restoring DHFR function in the cells. Transfected cells are then selected by culture in medium lacking thymidine, which DHFR is required to synthesise. If non-human cells are used as a production host, the gene encoding the specific binding molecule may be codon-optimised for expression in the chosen host.

In another aspect of the disclosure, a method of generating a host cell as defined above is provided. The method comprises introducing a nucleic acid molecule, recombinant construct or vector as defined herein into a cell which does not encode a specific binding molecule as defined above, i.e. a cell which does not encode a specific binding molecule as encoded by the nucleic acid molecule of the disclosure.

The cell into which the nucleic acid molecule, recombinant construct or vector is introduced may be any cell, as described above. For instance, the cell may be suitable for use as a cloning host or a production host, or may be an immune effector cell able to functionally express a membrane-bound specific binding molecule. Such cells are described above. Preferably the cell is a human T-cell or NK cell. Methods for introducing nucleic acid molecules into cells are also described above.

A cell which does not encode a specific binding molecule as defined above may be easily identified by the skilled person. A non-mammalian cell will not encode such a specific binding molecule unless modified to do so. Similarly, a mammalian cell which is not an immune effector cell will not encode such a specific binding molecule unless modified to do so. In the case of uncertainty as to whether a particular cell or cell line encodes such a specific binding molecule, the genome of the cell or cell line may be sequenced. In general, with the exception of the CD4+ T-cell from which hTERT-TCR-1 was isolated, no cell or cell line would be expected to encode such a specific binding molecule.

In another aspect of the disclosure, a specific binding molecule is provided, the specific binding molecule being capable of binding a hTERT peptide comprising the sequence set forth in SEQ ID NO: 1 when the peptide is presented by a Class II MHC, and comprising:
  (i) a first polypeptide comprising a variable region of an α-chain of a TCR comprising CDR sequences CDR1, CDR2 and CDR3 which respectively have the amino acid sequences set forth in SEQ ID NOs: 2, 3 and 4; and
  (ii) a second polypeptide comprising a variable region of a β-chain of a TCR comprising CDR sequences CDR1, CDR2 and CDR3 which respectively have the sequences set forth in SEQ ID NOs: 5, 6 and 7.

The specific binding molecule is soluble. That is to say, neither the first nor the second polypeptide of the specific binding molecule comprises a transmembrane domain. Preferably, the specific binding molecule provided herein is as described above with respect to the soluble specific binding molecules encoded by the nucleic acid molecule of the disclosure.

The first and second polypeptides of the specific binding molecule are joined. The first and second polypeptides may be located within a single amino acid chain, but preferably constitute separate amino acid chains. When the polypeptides constitute separate amino acid chains, they may be joined by any suitable method. Suitable methods are described above, and include covalent linkages (e.g. disulphide bonds) and non-covalent linkages, e.g. hydrophobic interactions, which may be driven by the use of leucine zippers.

The specific binding molecule may be synthesised by any method known in the art. In particular, the specific binding molecule may be synthesised using a protein expression system, such as a cellular expression system using prokaryotic (e.g. bacterial) cells or eukaryotic (e.g. yeast, fungus, insect or mammalian) cells. Cells which may be used in the production of the specific binding molecule are discussed above. An alternative protein expression system is a cell-free, in vitro expression system, in which a DNA sequence encoding the specific binding molecule is transcribed into mRNA, and the mRNA translated into a protein, in vitro. Cell-free expression system kits are widely available, and can be purchased from e.g. ThermoFisher Scientific (USA). Alternatively, specific binding molecules may be chemically synthesised in a non-biological system. Liquid-phase synthesis or solid-phase synthesis may be used to generate polypeptides which may form or be comprised within the specific binding molecule. The skilled person can readily produce specific binding molecules using appropriate methodology common in the art.

Following synthesis, the specific binding molecule is isolated and purified, using techniques known in the art. In particular, the specific binding molecule may be produced using a host eukaryotic cell. The specific binding molecule may be expressed such that the first and second polypeptide each comprise a leader sequence which directs the polypeptide for export. Leader sequences are discussed above. The specific binding molecule is thus exported from the production cell into the culture medium. The culture medium is then separated from the production cell, e.g. by centrifugation. The specific binding molecule may then be purified. For instance, the specific binding molecule may be expressed such that it comprises a tag for use in affinity chromatography. Suitable tags are described above and are well-known in the art. If a protease cleavage site is present between the tag and the mature specific binding molecule, the tag may be cleaved following purification of the specific binding molecule using the appropriate protease. Suitable proteases are known in the art and are described above. Methods of affinity chromatography are well-known in the art. If the specific binding molecule is a TCR-antibody construct, the specific binding molecule may be purified using an agent which specifically binds the Fc domain of an antibody, e.g. protein G, protein A or protein A/G.

If the specific binding molecule is produced in a host cell, but no leader sequences are included such that the first and second polypeptides are not secreted from the host cells, the specific binding molecule may be collected by harvesting and lysing the host cells producing the molecule. The individual skilled in the art can readily perform this task. Host cells may be harvested by centrifugation, and lysed by e.g. sonication, French Press, chemical lysis using a protein extraction reagent (e.g. BugBuster®, EMD Millipore (USA)), or a mammalian cell lysis kit as produced by e.g. AbCam (UK) or Sigma-Aldrich (USA)). Thereafter the soluble fraction of the lysate may be isolated using methods known in the art, e.g. centrifugation, and the specific binding molecule purified as described above.

If desired, the specific binding molecule may be multimerised to form a multimer. Such multimers form an aspect of the disclosure. For instance, multimerisation may be performed by conjugation of specific binding molecules to nanobeads, e.g. magnetic nanobeads. Methods for such conjugations are well known in the art. In another embodiment, specific binding molecules can be biotinylated and conjugated to streptavidin, to yield tetrameric specific binding molecule complexes. In order to biotinylate a specific binding molecule, one of the polypeptide chains should be expressed with a BirA sequence (SEQ ID NO: 65) at its C-terminus. Biotinylation of the specific binding molecule at the BirA sequence can then be performed using E. coli BirA (biotin ligase). Once biotinylated, the specific binding molecules can be incubated with streptavidin to produce tetramers.

In a particular embodiment, the specific binding molecule comprises a first polypeptide comprising a variable region of an α-chain as defined above, and a variable region of a β-chain as defined above. The variable region of an α-chain may in particular comprise or consist of the amino acid sequence set forth in SEQ ID NO: 8 or SEQ ID NO: 9, or a variant of SEQ ID NO: 8 or SEQ ID NO: 9. The variable region of a β-chain may in particular comprise or consist of the amino acid sequence set forth in SEQ ID NO: 10 or SEQ ID NO: 11, or a variant of SEQ ID NO: 10 or SEQ ID NO: 11. Preferably the full-length α-chain variable region of SEQ ID NO: 9 is paired with the full-length β-chain variable region of SEQ ID NO: 11. Sequence variants in this and other embodiments of the specific binding molecule are as defined above with respect to the encoding nucleic acid molecules.

The first polypeptide may further comprise a constant region of an α-chain, and the second polypeptide a constant region of a β-chain. As described above, the constant regions of TCR chains may be rendered soluble by C-terminal truncation, which results in removal of the transmembrane domain of the chain. Such constant regions are described above. The constant region of an α-chain may in particular comprise or consist of the amino acid sequence set forth in SEQ ID NO: 21 or a variant thereof. The constant region of a β-chain may in particular comprise or consist of the amino acid sequence set forth in SEQ ID NO: 22 or a variant thereof. As described above, the constant regions of these amino acid sequences comprise cysteine residues between which disulphide bonds may be formed, in order to join the first and second polypeptides.

In another embodiment, the constant region of an α-chain comprises or consists of the amino acid sequence set forth in SEQ ID NO: 29, or a variant thereof, and/or the constant region of a β-chain comprises or consists of the amino acid sequence set forth in SEQ ID NO: 30, or a variant thereof.

The first polypeptide may comprise or consist of the amino acid sequence set forth in SEQ ID NO: 41 or SEQ ID NO: 42, or a variant of SEQ ID NO: 41 or SEQ ID NO: 42. The second polypeptide may comprise or consist of the amino acid sequence set forth in SEQ ID NO: 43 or SEQ ID NO: 44, or a variant of SEQ ID NO: 43 or SEQ ID NO: 44. Preferably a first polypeptide of SEQ ID NO: 42, which comprises a full-length variable region of an α-chain, is paired with a second polypeptide of SEQ ID NO: 44, which comprises a full-length variable region of a β-chain.

In a particular embodiment, the specific binding molecule is a soluble TCR. As detailed above, the soluble TCR may be encoded as single chain, and in particular a 2A linker, such as that with the amino acid sequence set forth in SEQ ID NO: 18, may be used to join the first and second polypeptides. As detailed above, following self-splicing of a 2A linker, all but the C-terminal amino acid remain at the C-terminus of the polypeptide formed from the N-terminus of the original single chain. This segment of SEQ ID NO: 18 corresponds to amino acids 1-25 of SEQ ID NO: 18, the sequence of which is set forth in SEQ ID NO: 66.

The amino acid sequence of SEQ ID NO: 41 with the amino acid sequence of SEQ ID NO: 66 at its C-terminus is set forth in SEQ ID NO: 33. The amino acid sequence of SEQ ID NO: 42 with the amino acid sequence of SEQ ID NO: 66 at its C-terminus is set forth in SEQ ID NO: 34. The amino acid sequence of SEQ ID NO: 43 with the amino acid sequence of SEQ ID NO: 66 at its C-terminus is set forth in SEQ ID NO: 35. The amino acid sequence of SEQ ID NO: 44 with the amino acid sequence of SEQ ID NO: 66 at its C-terminus is set forth in SEQ ID NO: 36.

Thus in an embodiment the soluble TCR comprises a first polypeptide consisting of the amino acid sequence set forth in SEQ ID NO: 33 or SEQ ID NO: 34, or a variant of SEQ ID NO: 33 or SEQ ID NO: 34. A variant of SEQ ID NO: 33 or SEQ ID NO: 34 is an amino acid sequence having at least 95%, 96%, 97%, 98% or 99% sequence identity to SEQ ID NO: 33 or SEQ ID NO: 34, respectively, with the proviso that the VαCDR sequences are as defined above.

In an embodiment, the soluble TCR comprises a second polypeptide consisting of the amino acid sequence set forth in SEQ ID NO: 35 or SEQ ID NO: 36, or a variant of SEQ ID NO: 35 or SEQ ID NO: 36. A variant of SEQ ID NO: 35 or SEQ ID NO: 36 is an amino acid sequence having at least 95%, 96%, 97%, 98% or 99% sequence identity to SEQ ID NO: 35 or SEQ ID NO: 36, respectively, with the proviso that the VβCDR sequences are as defined above.

The soluble TCR may be linked or conjugated to a therapeutic or diagnostic agent, or a carrier which comprises or contains a therapeutic or diagnostic agent. A therapeutic agent is an agent used in therapy. By therapy is meant the treatment or prevention of a disease. In particular, the therapeutic agent may be an agent useful in the treatment of a neoplastic condition, particularly cancer.

The therapeutic agent may be a drug molecule, e.g. a toxin to kill a target cell. A suitable toxin is a toxin which, alone, is unable to enter, kill or otherwise disrupt a human cell but, when taken up by a human cell via a conjugated molecule, is able to exert its toxic effects. Such a toxin will thus only be taken up by, and exert its target effects on, a cell bound by a soluble TCR, into which the soluble TCR is taken up. The toxin may be any known appropriate cytotoxic species, i.e. it may be any suitable cytotoxin. By "cytotoxin" as used herein is meant any toxin which inhibits the growth and/or viability of a cell. Growth includes the division of a target cell (i.e. a cell into which it enters). The toxin may thus be any toxin which reduces or has a negative impact on the viability or survival of a cell and in particular includes any toxin which induces death of a target cell, e.g. the toxin may induce apoptosis or necrosis of a target cell.

Such a toxin may be a peptide toxin lacking a targeting domain. For instance, it may be a peptide toxin which natively lacks a targeting domain, or it may be a peptide toxin modified relative to its native form to remove its targeting domain. Examples of such toxins include saporin and gelonin, which are ribosome-inactivating proteins (RIPs) of the same family as e.g. ricin, but which are unable to cross the plasma membrane of a cell. Similarly, the enzymatic domains (i.e. catalytic domains) of a cytotoxin of a pathogen may be used, such as the enzymatic domain of a bacterial cytotoxin, e.g. the enzymatic domain of diphtheria toxin, *Pseudomonas* exotoxin A or a Clostridial cytotoxin, e.g. TcsL of *Clostridium sordellii*.

The soluble TCR may be encoded as a fusion protein, with a toxin located at the C-terminus of either the first or second polypeptide. Alternatively, the toxin may be conjugated to the soluble TCR using any suitable method known in the art. For instance, the soluble TCR molecule may be biotinylated on either its first or second polypeptide and conjugated to streptavidin-conjugated toxin (or vice versa) using the technique described above. Other suitable methods are known to those skilled in the art.

The therapeutic agent may be any other useful therapeutic agent, for instance a chemotherapy agent, or any other anti-cancer agent (e.g. an immunotherapeutic agent, checkpoint inhibitor, or any anti-cancer antibody), or anti-viral agent or suchlike.

A diagnostic agent is an agent useful for diagnostic purposes. Such an agent may in particular be a tracer or a label, i.e. an agent which can be detected in order to follow its passage through a human body. A tracer or label may in particular be detected by a scan, e.g. a PET scan or a CT scan. Many tracers and labels are known in the art, including radiolabels. Any suitable tracer or label may be used according to the present disclosure, including the common radioisotopes $^{11}C$, $^{13}N$, $^{15}O$, $^{18}F$, $^{99}Tc$ and $^{123}I$ and $^{125}I$. A diagnostic agent may be conjugated to a soluble TCR using any suitable labelling group, such as are known in the art. For instance, the soluble TCR may be radiolabelled using radiolabelled biotin.

The soluble TCR may be conjugated to a carrier comprising or containing a therapeutic or diagnostic agent. Pharmaceutical carriers are known in the art. Examples of suitable carriers include in particular micelles and liposomes. As is known to the skilled person, a micelle is an aggregate of surfactants (e.g. fatty acids) in an aqueous liquid, in which the hydrophilic head groups of the surfactants form the surface of the aggregate and the hydrophobic tail groups the core. A liposome is a spherical vesicle formed from a lipid bilayer surrounding an aqueous core. The therapeutic or diagnostic agent may be located within the core of a micelle or liposome.

Liposomes and micelles may be synthesised using any method known in the art.

Suitable methods for liposome synthesis and drug loading are described in e.g. Akbarzadeh et al., Nanoscale Res Lett 8(1): 102, 2013. Liposomes and micelles may be conjugated to soluble TCR molecules using methods known in the art, e.g. the methods taught in Reulen et al., Bioconjug Chem 18(2): 590-596, 2007; or Kung & Redemann, Biochim Biophys Acta 862(2): 435-439, 1986.

A soluble TCR conjugated to a therapeutic agent, or a carrier comprising a therapeutic agent, may be used in therapy. A soluble TCR conjugated to a diagnostic agent, or a carrier comprising a diagnostic agent, may be used in in vivo diagnostic methods.

In another embodiment, the specific binding molecule is a TCR-antibody construct. A TCR-antibody construct comprises a first polypeptide and a second polypeptide as described above, one of which further comprises the Fc domain of an antibody. The Fc domain of an antibody is preferably as described above.

In another aspect, the disclosure provides a composition comprising a specific binding molecule as provided herein or a host immune effector cell as provided herein and at least one pharmaceutically-acceptable diluent, carrier or excipient. The composition may be formulated in any convenient manner according to techniques and procedures known in the pharmaceutical art. The term "pharmaceutically-acceptable" as used herein refers to ingredients that are compatible with other ingredients of the compositions as well as physiologically acceptable to the recipient. The nature of the composition and carriers or excipient materials, dosages etc. may be selected in routine manner according to choice and the desired route of administration, purpose of treatment etc.

The pharmaceutical composition may be prepared for administration to a subject by any suitable means. Such administration may be e.g. oral, rectal, nasal, topical, vaginal or parenteral. Oral administration as used herein includes buccal and sublingual administration. Topical administration as used herein includes transdermal administration. Parenteral administration as defined herein includes subcutaneous, intramuscular, intravenous, intraperitoneal and intradermal administration.

Pharmaceutical compositions as disclosed herein include liquid solutions or syrups, solid compositions such as powders, granules, tablets or capsules, creams, ointments and any other style of composition commonly used in the art. Suitable pharmaceutically acceptable diluents, carriers and excipients for use in such compositions are well known in the art.

For instance, suitable excipients include lactose, maize starch or derivatives thereof, stearic acid or salts thereof, vegetable oils, waxes, fats and polyols. Suitable carriers or diluents include carboxymethylcellulose (CMC), methylcellulose, hydroxypropylmethylcellulose (HPMC), dextrose, trehalose, liposomes, polyvinyl alcohol, pharmaceutical grade starch, mannitol, lactose, magnesium stearate, sodium saccharin, talcum, cellulose, glucose, sucrose (and other sugars), magnesium carbonate, gelatin, oil, alcohol, detergents and emulsifiers such as polysorbates. Stabilising agents, wetting agents, emulsifiers, sweeteners etc. may also be used.

Liquid pharmaceutical compositions, whether they be solutions, suspensions or other like form, may include one or more of the following: sterile diluents such as water for injection, saline solution, preferably physiological, Ringer's solution, isotonic sodium chloride, fixed oils such as synthetic mono- or diglycerides which may serve as a solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as EDTA; buffers such as acetates, citrates or phosphates and agents for the adjustment of tonicity such as sodium chloride or dextrose. A parenteral preparation can be enclosed in ampoules, disposable syringes or multiple dose vials made of glass or plastic. An injectable pharmaceutical composition is preferably sterile.

In another aspect, the disclosure provides a host immune effector cell as provided herein, a specific binding molecule as provided herein or a composition as provided herein for use in therapy. By "therapy" as used herein is meant the treatment of any medical condition. Such treatment may be prophylactic (i.e. preventative), curative (or treatment intended to be curative), or palliative (i.e. treatment designed merely to limit, relieve or improve the symptoms of a condition). The therapy is for treatment of a human subject.

In a preferred embodiment, the therapy using the host immune effector cell or composition comprising the host immune effector cell is adoptive transfer therapy (alternatively known as adoptive cell transfer). Adoptive transfer therapy can be performed using known techniques. In an embodiment, the immune effector cells are formulated by first harvesting them from their culture medium, and then washing and concentrating the cells in a medium and container system suitable for administration (a pharmaceutically-acceptable carrier) in a treatment-effective amount. Suitable infusion medium can be any isotonic medium formulation, typically normal saline, e.g. Normosol™ R (Abbott) or Plasma-Lyte™ A (Baxter), but also 5% dextrose in water or Ringer's lactate can be utilised. The infusion medium can be supplemented with human serum albumin.

A treatment-effective amount of cells in the composition is at least 2 cells (for example, at least 1 CD8$^+$ central memory T-cell and at least 1 CD4$^+$ helper T-cell subset) or is more typically greater than $10^2$ cells, and up to $10^6$, up to and including $10^8$ or $10^9$ cells and can be more than $10^{10}$ cells. The number of cells will depend upon the ultimate use for which the composition is intended as will the type of cells included therein. For uses provided herein, the cells are generally in a volume of a litre or less, 500 ml or less, even 250 ml or 100 ml or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. For example, 2, 3, 4, 5, 6 or more separate infusions may be administered to a patient, at intervals of 24 or 48 hours, or every 3, 4, 5, 6 or 7 days. Infusions may also be spaced at weekly, fortnightly or monthly intervals, or intervals of 6 weeks or 2, 3, 4, 5, or 6 months. It is also possible that yearly infusions may be administered. In some aspects of the present invention, since all the infused cells are redirected to a particular target antigen (namely the hTERT peptide with the sequence of SEQ ID NO: 1), lower numbers of cells, in the range of $10^6$/kilogram ($10^6$-$10^8$ per patient) may be administered. The cell compositions may be administered multiple times at dosages within these ranges. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MFPTα, etc.) to enhance induction of the immune response.

The immune effector cells provided herein, which as described above express a membrane-bound specific binding molecule (e.g. a TCR), may be administered either alone, or as a pharmaceutical composition in combination with diluents and/or with other components such as IL-2 or other cytokines or cell populations. Such pharmaceutical compositions are described above.

In therapy using a specific binding molecule as provided herein, dosages etc. may be selected in routine manner according to choice and the desired route of administration, purpose of treatment, etc. Dosages may likewise depend upon the nature of the patient, e.g. age, size and condition, and the type and severity of the patient's disease. Appropriate dosages may be determined by clinical trials. Conveniently the specific binding molecule may be provided to a subject in a daily, weekly or monthly dose, or a dose in an intermediate frequency, e.g. a dose may be provided every 2, 3, 4, 5 or 6 days, every 2, 3, 4, 5 or 6 weeks, every 2, 3, 4, 5 or 6 months, annually or biannually. The skilled clinician will be able to calculate an appropriate dose for a patient based on all relevant factors, as outlined above.

The immune response induced in a subject by administering immune effector cells as provided herein may include cellular immune responses mediated by cytotoxic T-cells or NK cells capable of killing target cells (i.e. tumour cells expressing the hTERT peptide of SEQ ID NO: 1), regulatory T-cells and helper T-cells, and humoral immune responses, mediated primarily by helper T-cells capable of activating B-cells and thus generating an antibody response.

Administration to a subject of a soluble TCR carrying a drug molecule, e.g. a toxin, as described herein, leads to uptake of the soluble TCR/drug molecule conjugates by target cells, resulting in direct administration of the drug molecule to target cells. If the drug molecule is a toxin, this results in selective killing of the target cells. Administration of a TCR-antibody construct, as described herein, leads to binding of the TCR-antibody construct to target cells and initiation of an immune response against the target cells by Fc receptor-expressing cells of the immune system, e.g. B-cells, NK cells, macrophages, etc.

A specific binding molecule as provided herein may alternatively be used in an in vivo diagnostic method. Appropriate methods are known to the skilled physician, and include the utilisation of a specific binding molecule conjugated to a tracer or suchlike, e.g. a radiolabel, in scanning of a patient.

In a particular embodiment, the disclosure provides a host immune effector cell as provided herein, a specific binding molecule as provided herein or a composition as provided herein for use in the treatment of cancer. Cancer is defined broadly herein to include any neoplastic condition, whether malignant, pre-malignant or non-malignant. Generally, however, it may be a malignant condition. Both solid and non-solid tumours are included and the term "cancer cell" may be taken as synonymous with "tumour cell". The host immune effector cells, specific binding molecule and/or composition may be administered to a subject intravenously. Alternatively the cells, specific binding molecule and/or composition may be administered directly into a tumour via intratumoural injection.

The cancer to be treated is preferably a cancer which expresses hTERT (which is to say that the cells which constitute the cancer express hTERT). Whether a cancer expresses hTERT can be identified by e.g. analysis of a biopsy sample. A solid or liquid sample may be obtained by standard biopsy procedures, and analysed by histology, e.g. immunohistochemistry using an anti-hTERT antibody to identify hTERT expression. Other immunological methods may be used to identify hTERT expression, e.g. Western blot of a biopsy sample. hTERT expression may be identified by mRNA analysis, e.g. qPCR or RNA-Seq.

The cancer may be any cancer, though as noted above it preferably expresses hTERT. In particular embodiments, the cancer is pancreatic cancer, colon cancer or lung cancer. Pancreatic cancer includes pancreatic adenocarcinoma, neuroendocrine tumours of the pancreas, acinar cell carcinoma of the pancreas, pancreatoblastoma, and any other cancer type located within the pancreas. Lung cancer includes small-cell lung carcinoma and non-small cell lung carcinomas, such as large-cell carcinoma and squamous cell carcinoma of the lung.

In a related aspect the present disclosure provides a method of treatment comprising administering to a subject a host immune effector cell as provided herein, a specific binding molecule as provided herein or a composition as provided herein. Preferably, the host immune effector cell, specific binding molecule or composition is administered to the subject in a therapeutically effective amount. By "therapeutically effective amount" is meant an amount sufficient to show benefit to the condition of the subject. Whether an amount is sufficient to show benefit to the condition of the subject may be determined by the subject him/herself or a physician. Preferably, the method of treatment is for cancer, as described above.

In another related aspect, the present disclosure provides the use of a host immune effector cell as provided herein or a specific binding molecule as provided herein in the manufacture of a medicament for use in the treatment of cancer. The cancer may be as defined above.

In another aspect, the disclosure provides a kit comprising a first vector and a second vector. The first vector comprises a nucleotide sequence which encodes a first polypeptide as defined above, and the second vector comprises a nucleotide sequence which encodes a second polypeptide as defined above. As detailed above, the first polypeptide comprises a variable region of an α-chain, comprising CDR sequences CDR1, CDR2 and CDR3 which respectively have the amino acid sequences set forth in SEQ ID NOs: 2, 3 and 4; and the second polypeptide comprises a variable region of a β-chain, comprising CDR sequences CDR1, CDR2 and CDR3 which respectively have the sequences set forth in SEQ ID NOs: 5, 6 and 7. Variable and constant region sequences, and leader sequences, are described above, as are specific binding molecules which may be formed by the first and second polypeptides. In a particular embodiment the first vector encodes the α-chain of a TCR and the second vector encodes the β-chain of a TCR. In another specific embodiment the first vector encodes the C-terminally truncated α-chain of a soluble TCR and the second vector encodes the C-terminally truncated β-chain of a soluble TCR.

The first and second vectors may be co-introduced into a host cell, for co-expression of the first and second polypeptides and hence expression of the specific binding molecule. Suitable vectors and host cells are described above, as are methods of generating vectors and introducing vectors into cells. As noted above, a vector may comprise a selectable marker such that a cell which has taken up the vector can be positively selected. In a preferred embodiment, the first vector and the second marker each contain a selectable marker. The markers of the first and second vectors are preferably different, such that a cell which has taken up both vectors may be selected over a cell which has taken up only one of the two vectors (or neither vector). Suitable selectable markers are discussed above.

The two vectors may be provided in a single container (i.e. in a mixture of the two vectors) or in separate containers. The vectors may be provided in an aqueous solution (e.g. in water or a suitable buffer such as TE buffer) or may be provided in a lyophilised form.

The present invention may be more fully understood from the non-limiting Examples below and in reference to the drawings, in which:

FIGURE LEGENDS

Figure 1:
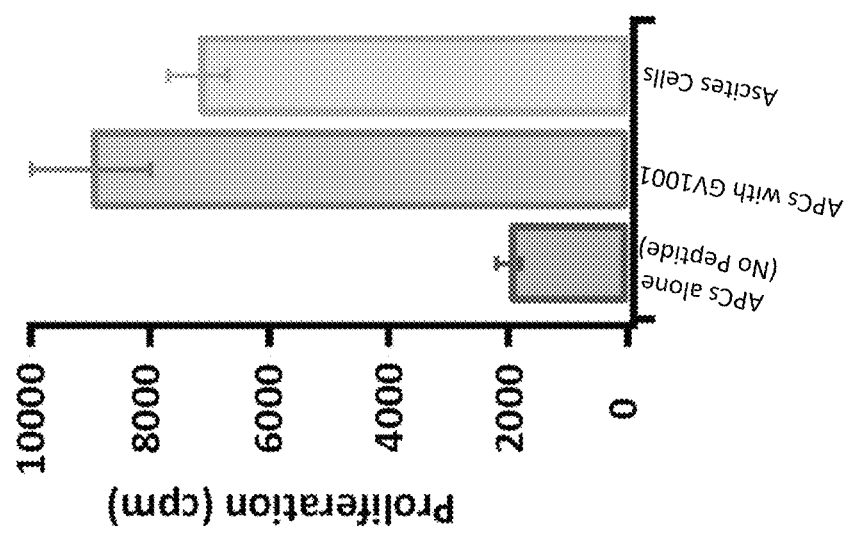

FIG. 1 shows that the original hTERT-TCR-1-expressing T-cell clone recognised autologous cancer cells in ascites. The clone was incubated with empty antigen-presenting cells (i.e. antigen-presenting cells (APCs) with no exogenous peptide added), APCs loaded with the GV1001 peptide and autologous ascites containing hTERT-expressing cancer cells. Target recognition was analysed by measurement of T-cell proliferation; proliferation demonstrates target recognition. Error bars indicate one standard deviation.

FIG. 2 shows that TCR-negative Jurkat T-cells expressed hTERT-TCR-1 following transduction with a vector encoding the TCR. Jurkat T-cells become CD3+ when expressing a functional TCR; CD3 staining demonstrated successful hTERT-TCR-1 expression.

Figure 3A:
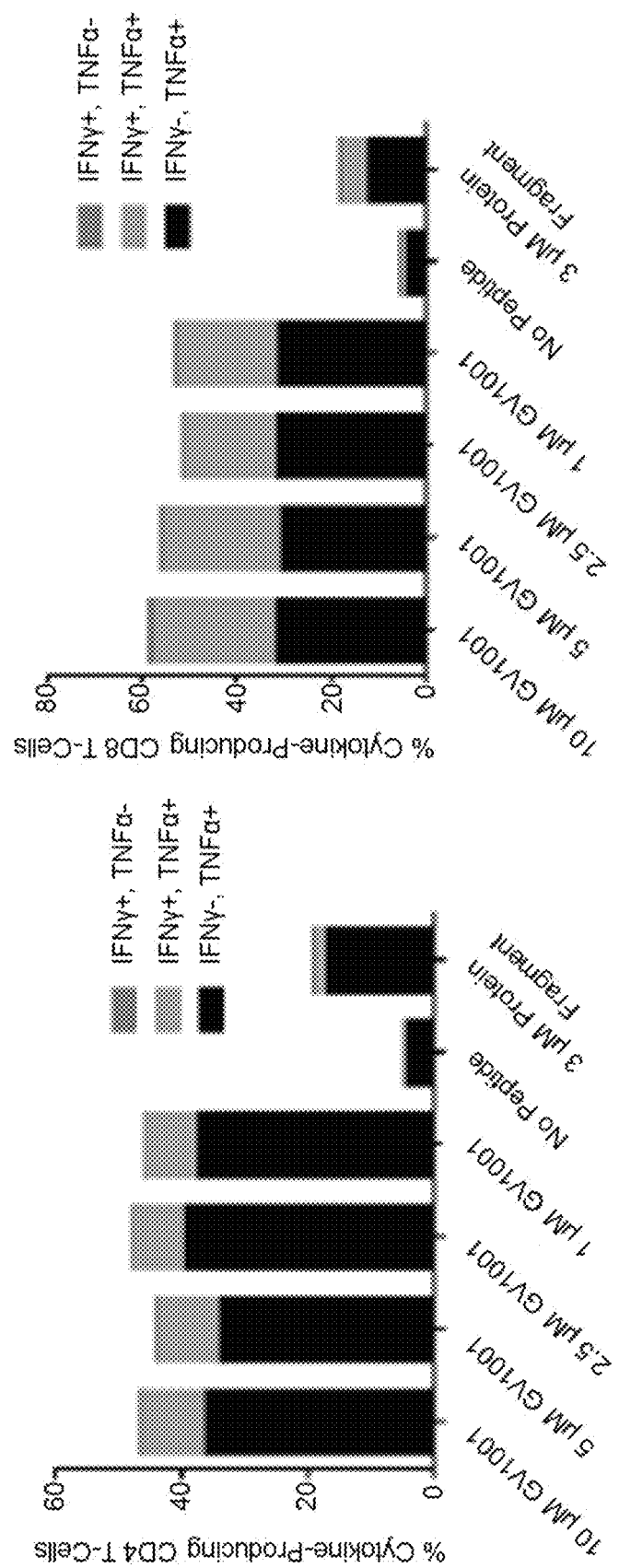
Figure 3B:
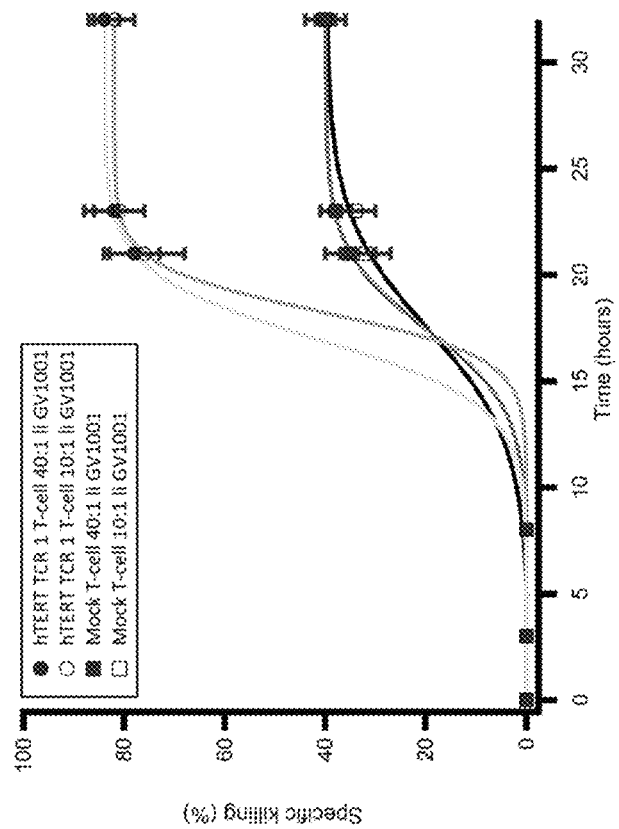

FIGS. 3A and 3B show that primary T-cells expressing hTERT-TCR-1 recognise GV1001 peptide-loaded target cells. T-cells were incubated with target cells, and target cell recognition determined based on cytokine production by the T-cells. Recognition by both CD4+ and CD8+ T-cells was demonstrated. FIG. 3A shows the proportion of CD4+ (left-hand side) and CD8+ (right-hand side) T-cells which produced the IFNγ and/or TNFα following challenge with the various target cells. FIG. 3B presents the same data in a different format, demonstrating the total proportion of CD4+ and CD8+ T-cells which produced cytokines following challenge with target cells loaded with the defined concentrations of GV1001 peptide. Error bars indicate one standard deviation.

Figure 4:
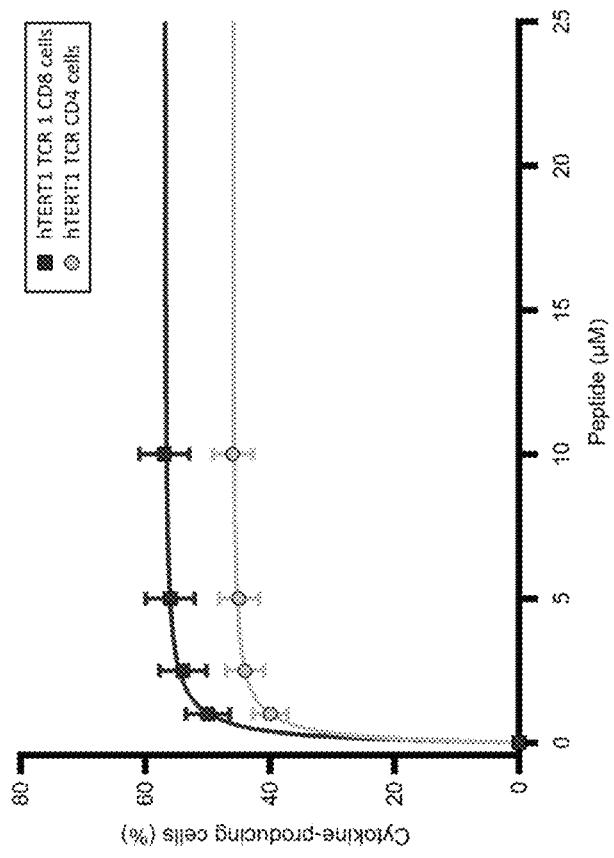

FIG. 4 shows that primary T-cells expressing hTERT-TCR-1 can specifically kill target melanoma cells (ESTDAB-039, DP4+ hTERT+), whereas control (mock-transfected) T-cells had no activity against the melanoma cells. Error bars indicate one standard deviation. Effector:target ratios are indicated.

Figure 5:
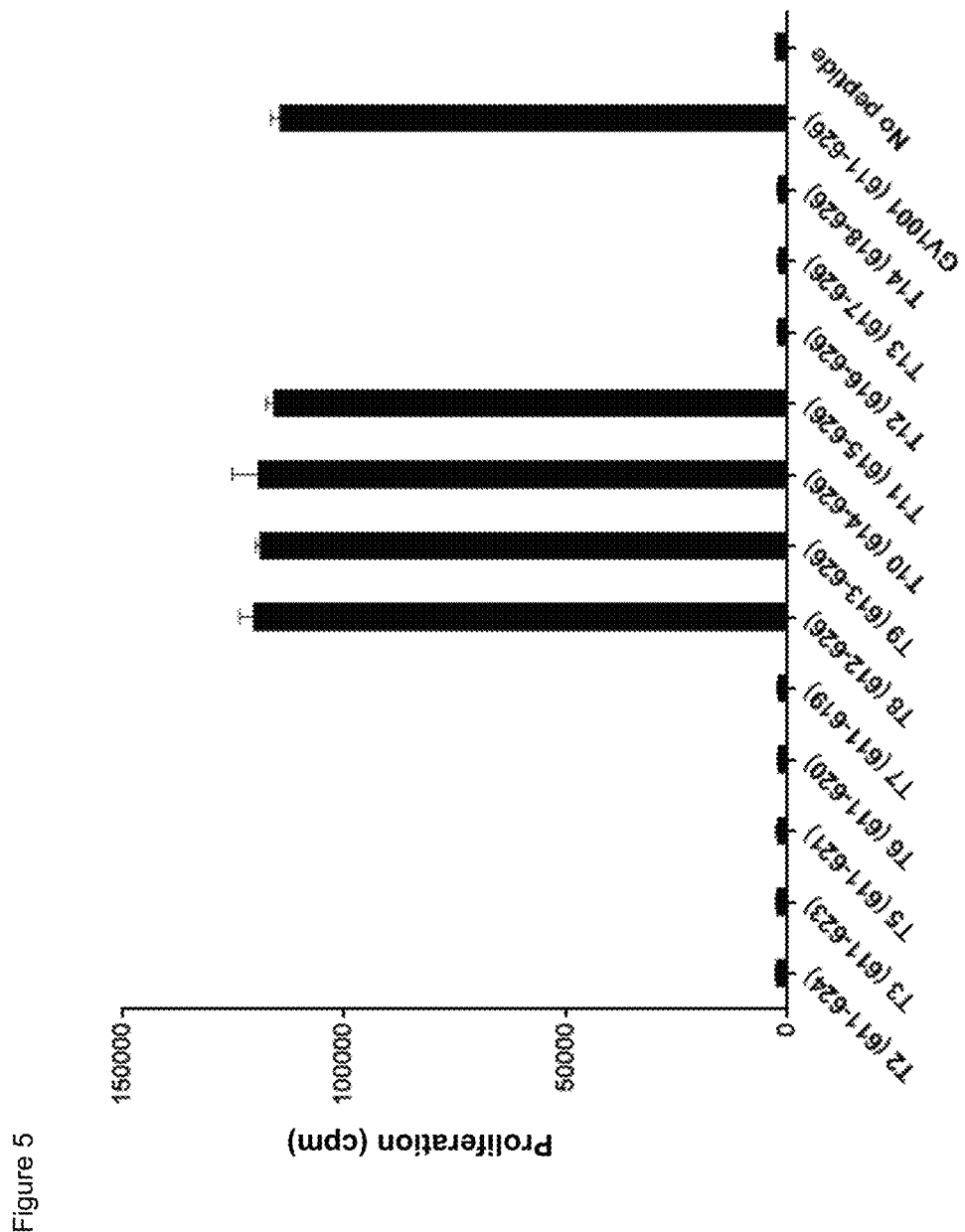

FIG. 5 shows the identification of the minimal hTERT-TCR-1 epitope. EBV-LCL (Epstein-Barr virus-transformed lymphoblastoid cell line) cells were used as APCs, and loaded with hTERT peptides. The peptides are defined by their sequence locations within hTERT (x-axis), and target recognition determined based on T-cell proliferation. Error bars indicate one standard deviation.

Figure 6A:
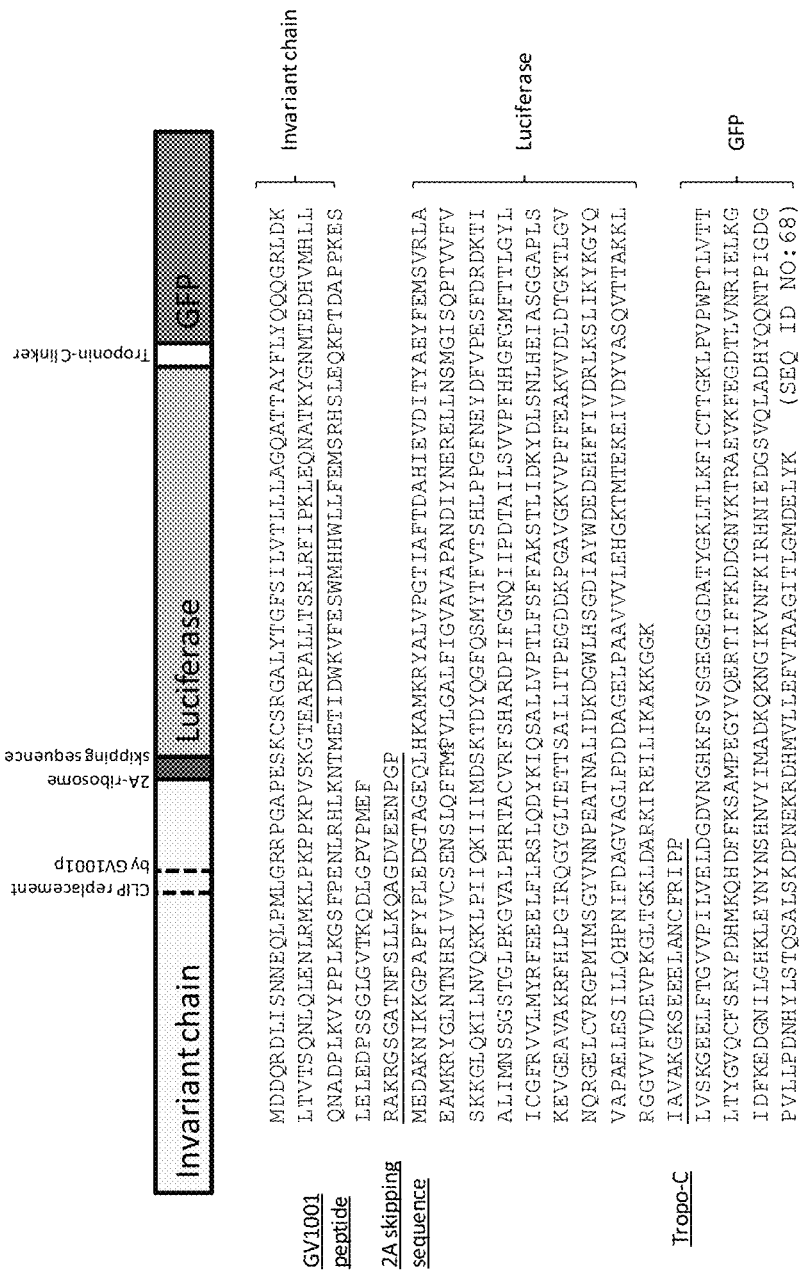
Figure 6C:
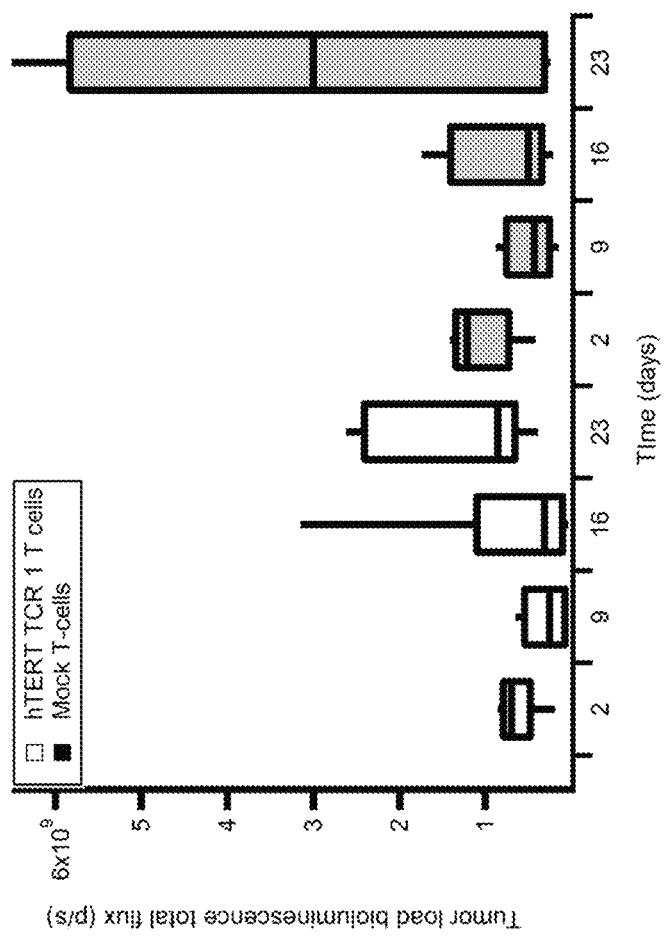
Figure 6B:
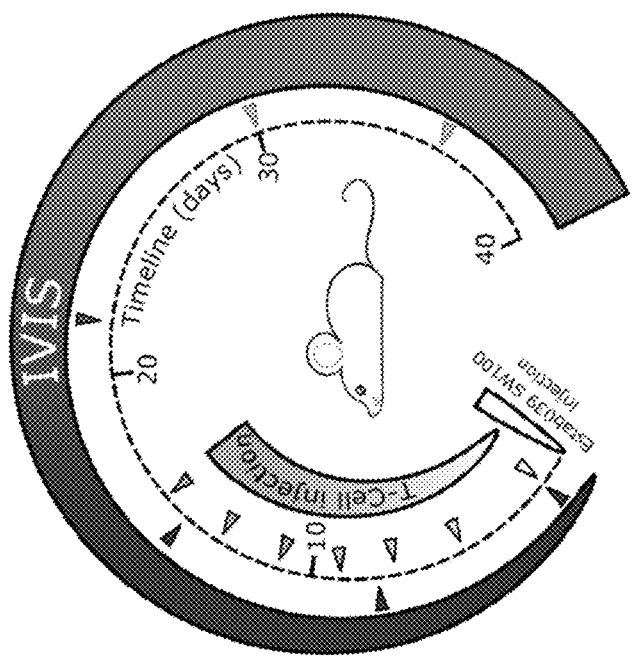

FIGS. 6A, 6B, and 6C show the results of xenograft studies in mice. Mice were injected with ESTDAB-039 tumour cells engineered with a retroviral vector, SW1000, to express the hTERT-TCR-1 antigen (GV1001), firefly luciferase and EGFP. SW1000 encoded these three genes within a single open reading frame, the structure and amino acid sequence of which (SEQ ID NO: 68) is shown in FIG. 6A. FIG. 6B is a schematic diagram showing the time-line for the xenograft experiments. The time-line shows the days of the study, when mice were injected and when they were imaged. As shown, mice were injected with SW1000-engineered ESTDAB-039 tumour cells at the beginning of the experiment. Mice were injected with hTERT-TCR-1-expressing T-cells at the points shown (the arrows pointing from "T-cell injection" to the timeline) and imaged in the IVIS in vivo imaging system at the point shown (the arrows pointing from "IVIS" to the timeline).

FIG. 6C shows the results of the experiments. Tumour load was measured by IVIS based on total bioluminescence at the days indicated (following SW1000-engineered ESTDAB-039 cell injection). Tumour load of mice injected with T-cells transfected with hTERT-TCR-1 is compared to the tumour load of mock-transfected T-cells.

FIGS. 7A and 7B show that hTERT-TCR-1 T-cells promote specific tumour apoptosis. FIG. 7A shows the lysis kinetics obtained by bioluminescence (BLI) assay of effector T-cells co-cultured with two different tumour cell lines stably transduced with Ii-hTERT (Granta-519 and HLA-DP04+ EBV-LCL). Data represent mean±standard deviation (SD) of quadruplicates. Statistics were calculated on the 9.5-hour time point. FIG. 7B shows the density of Annexin V+ cells (i.e. apoptotic cells) after co-culture of effector T-cells and patient ascites cells is shown. Data represent mean±SD of dodecaplicates. Statistics were calculated on the 10-hour time point.

Figure 8B:
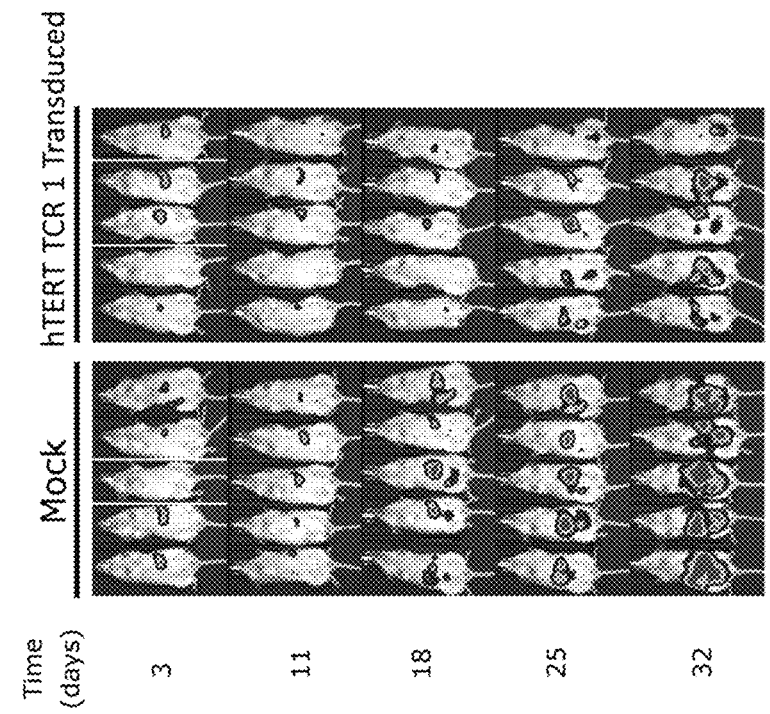
Figure 8A:
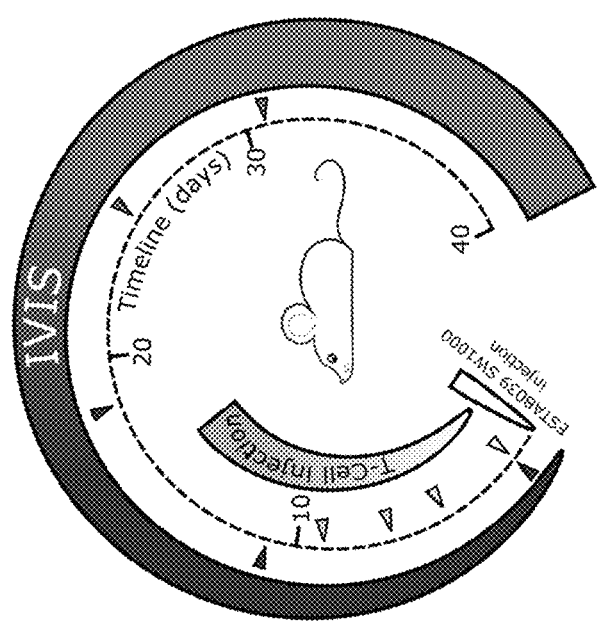
Figure 8C:
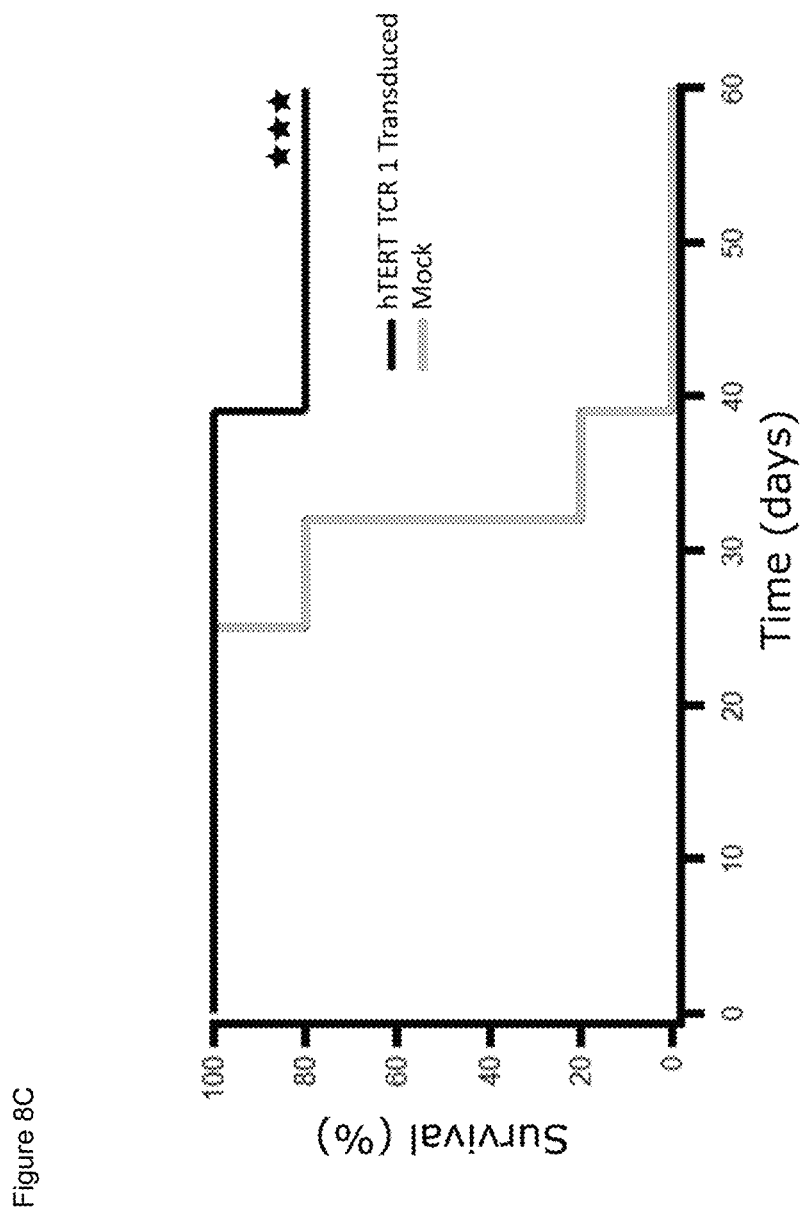

FIGS. 8A, 8B and 8C show that hTERT-TCR-1 T-cells control tumour load in vivo. NSG mice were engrafted with GFP/Luc+ ESTDAB-1000 tumors intra-peritoneally (i.p.) and 3 days after tumor inoculation, mice were randomized and received i.p. injections of mock T-cells, hTERT-TCR-1 transduced T-cells or medium (n=10 for each group) for a total of 4 injections. This experiment timeline is shown in FIG. 8A.

FIG. 8B shows luminescence images obtained from IVIS of mice inoculated with ESTDAB-1000 and treated with mock or hTERT-TCR-1 transduced T-cells.

FIG. 8C shows Kaplan-Meier survival curves of the mice shown in FIG. 8B. Survival curves were analysed by Mantel-Cox (log-rank) test. Data represent mean±SD.

Figure 9:
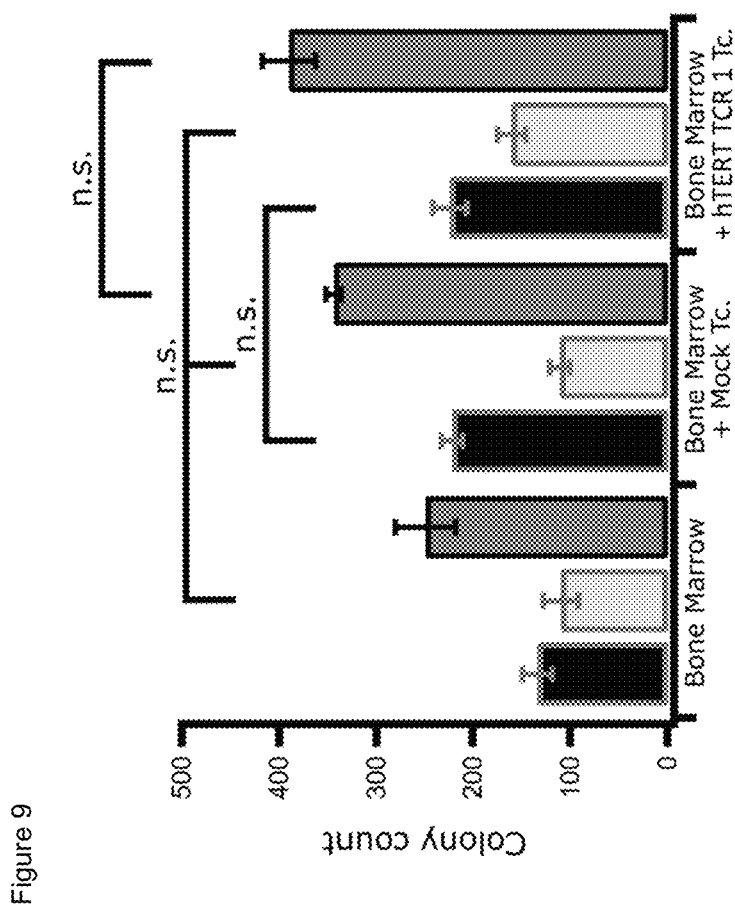

FIG. 9 shows that hTERT-TCR-1 T-cells do not react against bone marrow. Healthy donor bone marrow progenitor cells were co-cultured with hTERT-TCR-1 transduced T-cells or mock-transfected T-cells for 6 hours at an Effector:Target ratio (E:T) of 10:1. The cells were then plated in semisolid methylcellulose progenitor culture for 14 days and scored for the presence of red (CFU-E), white (CFU-GM) and mixed (CFU-GEMM) colonies. For each set of three columns, the left-hand column represents CFU-E colonies, the middle column CFU-GM colonies and the right-hand column CFU-GEMM colonies. Data represent mean±SD of triplicates.

Figure 10:
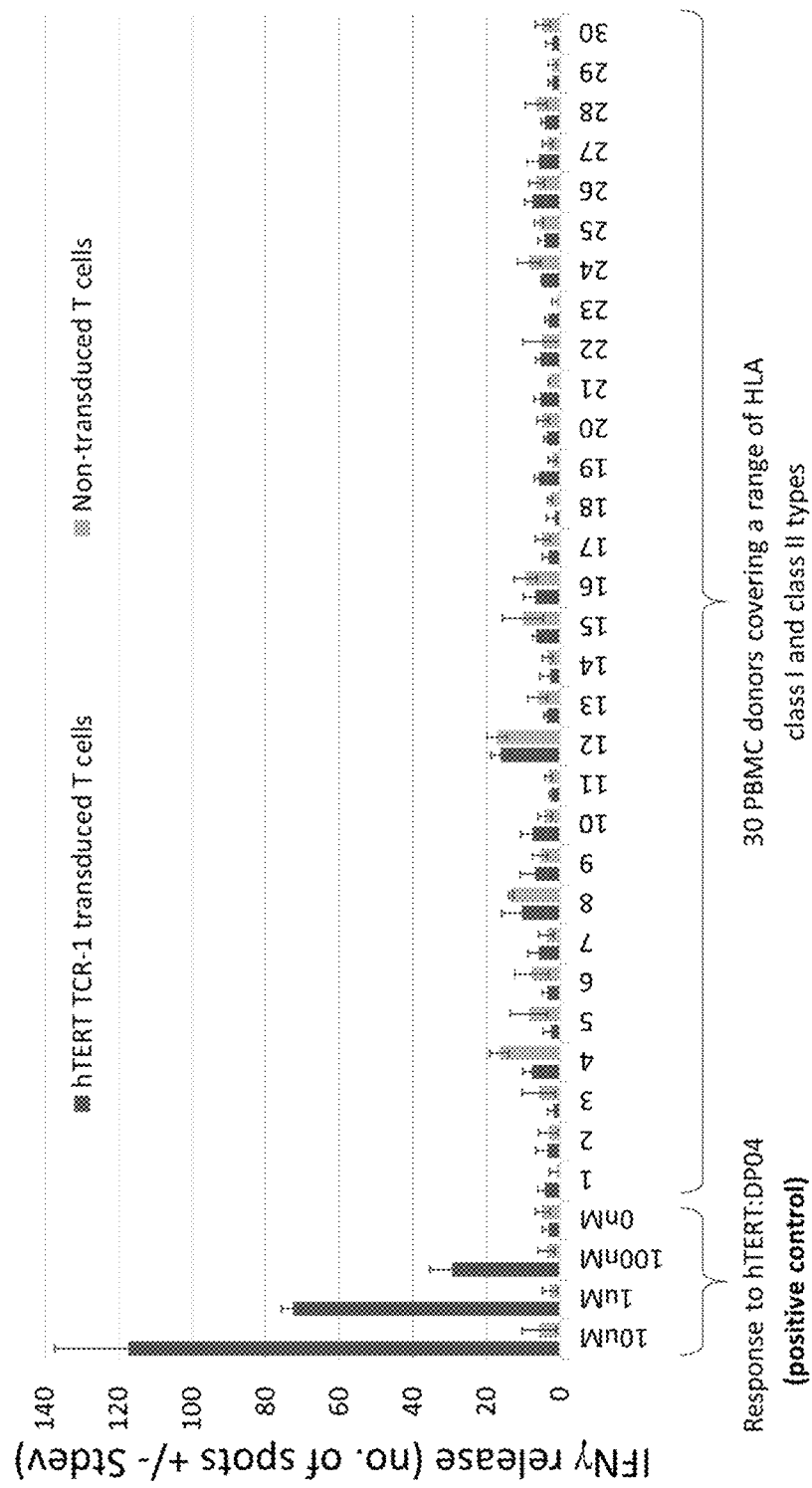

FIG. 10 shows that hTERT-TCR-1-expressing T-cells do not show alloreactivity against PBMCs isolated from a panel of 30 donors. hTERT-TCR-1 transduced T-cells or non-transduced T-cells were incubated with PBMCs at an E:T ratio of 1:5. Controls included incubation of T-cells with titrating concentrations of hTERT peptide with HLA-DPB1*0401 PBMCs. Following overnight incubation at 37° C., IFNγ release was measured by ELISPOT. The figure shows mean IFNγ release and error bars represent SD.

EXAMPLES

Methods
Cell Lines, Media and Reagents

T-cells were isolated from blood from healthy donors. Epstein Barr Virus-transformed lymphoblastoid cell lines (EBV-LCLs) used as target cells were generated by transformation of B-cells from HLA-A2+ donors as previously described (Gjertsen et al., *Int. J. Cancer* 72: 784-790, 1997). Melanoma cell line ESTDAB-039 was a kind gift from Graham Pawelec (University of Tübingen, Germany). J76 cells were a kind gift from Mirjam Heemskerk (Leiden University, Netherlands). Cell lines were cultured in RPMI-1640 (Gibco, Thermo Fisher Scientific, USA) supplemented with gentamicin and 10% heat-inactivated FCS (Life Technologies, Thermo Fisher Scientific). All T-cells were grown in CellGro™ DC medium (CellGenix GmbH, Germany) supplemented with 5% heat-inactivated human pooled serum (PAN-Biotech GmbH, Germany), 10 mM N-acetyl-cysteine (Mucomyst™ 200 mg/ml, AstraZeneca AS, UK), 0.01 M HEPES (Life Technologies, Thermo Fisher Scientific) gentamycin 0.05 mg/ml (Garamycin, Schering-Plough Europe, Belgium), and 100 U/ml IL-2 (Chiron, USA), denoted complete medium hereafter, unless otherwise stated.

$^3$H-Thymidine Incorporation Assays for Measuring Proliferation (FIGS. 1 and 5)

The peptide-specific proliferative response was determined by seeding T-cells in 96-well plates at $0.5 \times 10^5$ cells/well in CellGro™ DC medium (CellGenix GmbH, Germany) supplemented with HEPES buffer, N-acetyl cysteine and gentamycin. Autologous antigen-presenting cells (APCs), either autologous peripheral blood mononuclear cells (PBMCs) or EBV-LCLs irradiated at 3000 rad or 10 000 rad, respectively, to prevent proliferation, were washed and seeded at 0.5×10⁵ cells/well. All conditions were tested in triplicate: T-cells and irradiated APCs alone (included as a control), T cells and irradiated APCs with GV1001 peptide (FIG. 1) or truncated peptides with indicated amino acid sequences (FIG. 5), at 10-25 µM peptide making a total volume of 200 µl/well. T-cells were also tested for reactivity against autologous cancer cells isolated from patient ascites (FIG. 1). On day 2 the cells were subjected to $^3$H-thymidine, (20 µl/well, a total of 0.037 MBq/well) overnight (between 16-20 hours). The proliferation is shown as mean counts per minute (cpm).

In Vitro mRNA Transcription of TCR Targeting hTERT

A telomerase (hTERT)-specific, HLA-DP4-restricted TCR was identified in a T-cell clone from a GV1001 peptide-vaccinated pancreatic cancer patient (Bernhardt, S. L. et al., supra) and named hTERT-TCR-1. The in vitro mRNA synthesis was performed essentially as previously described (Almåsbak, H. et al. *Cytotherapy* 13(5): 629-640, 2011). Anti-Reverse Cap Analog (Trilink Biotechnologies Inc., San Diego, CA, USA) was used to cap the RNA. The mRNA was assessed by agarose gel electrophoresis and Nanodrop™ spectrophotometer (Thermo Fisher Scientific, Waltham, MA, USA).

In Vitro Expansion of Human T-Cells

T-cells from healthy donors were expanded using a protocol adapted for GMP production of T-cells employing Dynabeads™ CD3/CD28 essentially as previously described (Almåsbak H., et al., supra). In brief, PBMCs were isolated from buffy coats by density gradient centrifugation and cultured with Dynabeads (Dynabeads® ClinExVivo™ CD3/CD28, kindly provided by Dynal, Thermo Fisher Scientific) at a 3:1 ratio in complete Cell-Gro™ DC Medium with 100 U/ml recombinant human interleukin-2 (IL-2) (Proleukin, Prometheus Laboratories, USA) for 10 days. The cells were frozen and aliquots were thawed and rested in complete medium before transfection.

Electroporation of J76 Jurkat Cells and Expanded T-Cells

Expanded T-cells were washed twice and resuspended in CellGro™ DC medium (CellGenix GmbH) and resuspended to 70×10⁶ cells/m. The mRNA was mixed with the cell suspension at 100 µg/ml, and electroporated in a 4 mm gap cuvette at 500 V and 2 ms using a BTX 830 Square Wave Electroporator (BTX Technologies Inc., Hawthorne, NY, USA). Immediately after transfection, T-cells were transferred to complete culture medium at 37° C. in 5% CO₂ overnight to allow TCR expression. The same protocol was used to electroporate J76 Jurkat cells.

In Vitro Functional Assay, Antibodies and Flow Cytometry (FIGS. 2, 3A and 3B)

For extracellular staining only, cells were washed in staining buffer (SB) consisting of phosphate buffered saline (PBS) containing 2% FCS before staining for 20 min at RT. The cells were then washed in SB and fixed in SB containing 1% paraformaldehyde.

Peptide GV1001, EARPALLTSRLRFIPK (SEQ ID NO: 52) from the hTERT protein (hTERT sequence, GenBank accession number: AB085628) was provided by ProImmune Ltd, UK. For intracellular staining, T-cells were stimulated for 6 hours with APCs loaded with GV1001 peptide or a 173 amino acid (563-735) recombinant hTERT protein fragment (GenScript, USA) at the indicated concentrations, at an effector to target (E:T) ratio of 2:1 and in the presence of BD GolgiPlug™ inhibitor and BD Golgistop™ inhibitor at recommended concentrations. Cells were stained extracellularly and intracellularly using the PerFix-nc™ kit according to the manufacturer's instructions (Beckman Coulter Inc, USA). The following antibodies were used: CD3-APC, CD4-BV421 (BioLegend), CD8-PE-Cy7, IFN-γ-FITC, TNF-α-PE (BD Biosciences, USA). Antibodies were purchased from eBioscience, USA, except where noted. Cells were acquired on a BD FACSCanto10™ flow cytometer and the data analysed using FlowJo™ software (Treestar Inc., Ashland, OR, USA).

Bioluminescence-Based Cytotoxicity Assay (FIGS. 4, 7A, and 7B)

Luciferase-expressing tumour cells were counted and resuspended at a concentration of 3×10⁵ cells/ml. Cells were given Xenolight™ D-Luciferin potassium salt (75 µg/ml; Perkin Elmer) and were placed in 96-well white round bottomed plates at 100 µl cells/well in triplicate. Effector T-cells were added at indicated E:T ratios. In order to determine spontaneous and maximal killing, wells with target cells only or with target cells in 1% Triton™ X-100 (Sigma-Aldrich), respectively, were seeded. Cells were left at 37° C. and the bioluminescence (BLI) was measured with a luminometer (VICTOR Multilabel Plate Reader) as relative light units (RLU) at indicated time points. Target cells that were incubated without any effector cells were used to determine baseline spontaneous death RLU in each time point. Triplicate wells were averaged and lysis percentage was calculated using the following equation: % specific lysis=100×(spontaneous cell death RLU−sample RLU)/(spontaneous death RLU−maximal killing RLU). Sigmoid curves (no Hill equation) were fitted for every set of points (using Igor Pro 6.36 or 8.1) as guide for the eye with standard deviation as weighting factor, base hold to 0 and max lysis kept below 100.

Mouse Xenograft Studies (FIGS. 6A, 6B, 6C, 8A, 8B, and 8C) NOD.Cg-Prkdc$^{scid}$ Il2rg$^{tm1WT}$/SzJ (NSG) mice were bred in-house under an approved institutional animal care protocol and maintained under pathogen-free conditions. 6-8 week-old mice were injected intra-peritoneally (i.p.) with 1-1.5×10⁶ ESTDAB-039 tumour cells. The ESTDAB-039 cells were engineered with a retroviral vector, SW1000, to express the hTERT-TCR-1 antigen (for TCR testing) in combination with firefly luciferase (for in vivo analysis) and EGFP (to detect the transfected cells and sort them). The structure of the construct is shown in FIG. 6A; it consists of the coding sequence of the invariant chain (CD74) containing a CLIP peptide replacement in order to load MHCI (Wälchli et al., *Eur. J. Immunol.* 44: 774-784, 2014) and MHCII (Mensali et al., in preparation) molecules. The peptide used to replace the CLIP sequence is GV1001 (SEQ ID NO: 52). This sequence was introduced after opening the vector using unique restriction sites at both ends of the CLIP region and using an oligonucleotide fusion method. Invariant chain was then fused with a Luciferase-GFP module through a picornavirus 2A ribosome skipping sequence after removing its natural STOP codon by PCR. The Luciferase-GFP module was extracted from an initial construct (Löw et al., *BMC Biotechnol.* 20:81, 2010) and rendered compatible to the fusion with invariant chain-2A fragment by adding unique restriction sites by PCR, then subcloned into the pENTR™ vector (Invitrogen). The full construct was sequence verified and finally subcloned into the pMP71 retroviral vector. The antigen construct is referred to as li-hTERT.

The sequence of the whole fusion protein is set out in SEQ ID NO: 68 and provided in FIG. 6A, with an indication of the different regions of interest. Retroviral particles were produced as depicted in Wälchli et al. (*PLoS One,* 6(11): e27930, 2011) and used to transduce ESTDAB-039 cells.

Cells were sorted on the basis of their GFP expression and a pure GFP-positive population was expanded and stocked. The reactivity of the hTERT-TCR-1-redirected T-cells was checked against these cells before they were injected into animals.

Tumour growth was monitored by bioluminescent imaging using the Xenogen™ Spectrum system and Living Image™ v3.2 software. Anaesthetised mice were injected i.p. with 150 mg/kg body weight of D-luciferin (Caliper Life Sciences, Hopkinton, MA). Animals were imaged 10 minutes after luciferin injection. 8-10×10$^6$ hTERT-TCR-1 mRNA-electroporated T-cells (FIGS. 6A, 6B and 6C) or 10$^7$ hTERT-TCR-1 transduced T-cells (FIGS. 8A, 8B, and 8C), or 10$^7$ mock-transfected T-cells as a control were injected i.p. as indicated. Schematic diagrams showing the timelines for animal injections for the two experiments are shown in FIGS. 6B and 8B.

Retroviral Particle Production for T-Cell Transduction 1.2×10$^6$ HEK293T cells (Cellbiolabs, US) cells were plated in 6 cm plates. Transfection was performed using X-treme-GENE 9™ transfection reagent (Roche) with a mix of DNA including the retroviral packaging vectors and the hTERT-TCR-1 expression vector to an equimolar ratio. After 24 hours, the medium was replaced with 1% HyClone™ FCS-containing DMEM and the cells were transferred to a 32° C. incubator. Supernatants were harvested after 24 h and 48 h incubation.

Retroviral Transduction of Expanded T-cells PBMCs were incubated for 2 days in a 24-well plate coated with CD3 and CD28 at 1×10$^6$ cells/mL. A 24-well plate was coated with 50 μg/mL RetroNectin™ reagent for 3 hours at room temperature before being washed with PBS and blocked with a solution of PBS supplemented with 0.1% FBS for 30 minutes. 1 mL virus solution was then deposited in each well, which was then topped with 500 μL activated T-cells at a concentration of 0.3×10$^5$ cells/mL. The plate was then incubated for 30 minutes under a controlled atmosphere (37° C., 5% $CO_2$) for 30 minutes, sealed and then spun down at 750×g at 32° C. for 60 minutes before being placed back in the incubator.

The same spinoculation step was repeated the following day before the cells were collected, spun down, washed and resuspended in complete X-Vivo 15 medium for 2 days before the expression of the TCR was checked and the cells expanded using the procedure described above.

Annexin V-Based Cytotoxicity Assay (FIGS. 7A and 7B)

10$^4$ tumour cells (patient ascites cells) were incubated in a 96-well flat-bottomed plate in 200 μL complete RPMI 1640 medium for 24 hours under a controlled atmosphere (37° C., 5% $CO_2$). The following day, the plate was centrifuged at 100×g for 1 min and 100 μL supernatant was discarded. 50 μL of a 1:200 solution of IncuCyte™ Annexin V Red (Essen Biosciences, UK) diluted in complete RPMI 1640 was added to each well and the plate was then incubated at 37° C., 5% $CO_2$ for 15 min.

Effector cells (hTERT-TCR-1 transduced or electroporated primary T-cells or patient T-cell clones, or mock-transfected T-cells) previously washed and resuspended in complete RPMI 1640 medium were introduced into each well at a final concentration of 5×10$^4$ cells/mL (100 μL/well). The plate was then put into an IncuCyte™ S3 live cell analysis system (Essen Biosciences, UK) with the following settings: 12 images/day, 4 images/well, 2 channels (phase and red), 12 wells per condition. Analysis of cytotoxicity was performed using IncuCyte™ software. Metrics were then extracted and corrected using Igor Pro™ 8.1 (Wavemetrics, USA). Background was calculated on mock images and consecutively subtracted from all the other conditions.

Testing Against Bone Marrow in a Colony Forming Unit (CFU) Assay (FIG. 9)

Healthy HLA-DP04+ donor bone marrow (n=4 in total) progenitor cells were co-cultured with hTERT-TCR-1 transduced T-cells or mock-transfected T-cells for 6 hours at an E:T of 10:1. The cells were then plated in semisolid methylcellulose progenitor culture for 14 days and scored for the presence of red (CFU-E, i.e. erythroid), white (CFU-GM, i.e. granulocyte and monocyte) and mixed (CFU-GEMM, i.e. granulocyte, erythrocyte, monocyte and megakaryocyte) colonies. Data represent mean±SD of triplicates.

Alloreactivity Study (FIG. 10)

PBMCs were isolated from 30 donors as described above. hTERT-TCR-1 transduced T-cells or non-transduced controls were incubated with the PBMCs at an Effector:Target ratio of 1:5 (10000:50000). Controls included incubation of T-cells with titrating concentrations of hTERT peptide GV1001 (10 μM, 1 μM and 100 μM) with HLA-DPB1*0401 PBMC, and T-cells incubated with HLA-DPB1*0401 PBMC in the absence of hTERT peptide GV1001. The assay was incubated at 37° C. overnight and IFNγ release measured by ELISpot (R&D Systems, US) according to the manufacturer's protocol. Bars represent mean and error bars are SD (n=3).

Statistical Analysis

Continuous data were described with mean and standard deviation Unless stated otherwise all statistics were obtained using the multi-variated bidirectional Student t-test. The Mantel-Haenszel test was used as log-rank estimator for survival curves. *p<0.05, p<0.01, *p<0.001, All statistical analyses were performed using R software.

Results hTERT-TCR-1 is Functionally Expressed by T-Cells

To confirm expression of hTERT-TCR-1 following transfection of T-cells, Jurkat T-cells were transfected and expression of hTERT-TCR-1 detected. Successful hTERT-TCR-1 expression was determined based on surface CD3 expression. CD3 is only expressed on the surface of Jurkat cells when a TCR is co-expressed. Jurkat T-cells were transfected with hTERT-TCR-1 or mock-transfected, stained with allophycocyanin-conjugated anti-CD3 antibody and analysed by flow cytometry. As shown in FIG. 2, transfected T-cells were stained with the anti-CD3 antibody, while mock-transfected T-cells were not, demonstrating successful expression of the TCR, To confirm TCR functionality in vitro, T-cells transfected to express hTERT-TCR-1 were incubated with antigen-presenting cells (APCs) with GV1001 peptide or autologous cancer cells from ascites; as a control, the same T-cells were also incubated with APCs without any exogenous peptide. T-cell activation was measured based on proliferation. Proliferation was analysed by $^3$H-thymidine incorporation assays. The T-cells incubated with the APCs and GV1001 peptide proliferated more than four-fold more than the control T-cells (FIG. 1) demonstrating that T-cells expressing the hTERT-TCR-1 TCR are activated by exposure to APCs presenting the GV1001 peptide.

T-cells expressing hTERT-TCR-1 were also incubated with APCs loaded with GV1001 peptide at a series of concentrations. As a control, unloaded APCs were also tested. As shown in FIGS. 3A and 3B, both CD4+ and CD8+ T-cells transfected with hTERT-TCR-1 were stimulated to produce the cytokines IFNγ and/or TNFα in response to APCs loaded with GV1001 (FIG. 3A). As shown in FIG. 3B, the response to APCs loaded with increased concentrations of GV1001 rapidly plateaus for both CD4+ and CD8+ T-cells; a greater proportion of CD8+ T-cells were activated than CD4+ T-cells. This demonstrated that both CD4+ and CD8+ T-cells expressing hTERT-TCR-1 are stimulated to produce cytokines upon recognition of the hTERT-TCR-1 antigen GV1001 when presented by an APC.

To test target cell-killing by hTERT-TCR-1-expressing T-cells, transfected T-cells were incubated with hTERT+, HLA-DP4+ melanoma cells (ESTDAB-039 cell line) at two different effector:target ratios (as shown in FIG. 4). As a control, mock-transfected T-cells were also incubated with the same melanoma cell line. Target cell killing was measured based on bioluminescence. As shown in FIG. 4, T-cells transfected with hTERT-TCR-1 displayed approximately twice the level of specific killing of target cells as that displayed by mock-transfected T-cells. This demonstrates that the hTERT-TCR-1 TCR is able to activate T-cells to kill target cells expressing the antigen (hTERT).

To identify the minimal epitope recognised by hTERT-TCR-1, T-cells expressing hTERT-TCR-1 were incubated with APCs and GV1001 (as a positive control), APCs with no exogenous peptide (as a negative control) and APCs with a variety of shorter peptides located with GV1001. GV1001 corresponds to amino acids 611-626 of hTERT; it was found that the 4 N-terminal amino acids of GV1001 were not required for peptide recognition (removal of these residues did not affect T-cell activation), but removal of further cells from the N-terminus of GV1001, or of any amino acids from the C-terminus of GV1001, prevented recognition of the peptide by hTERT-TCR-1 (FIG. 5). Accordingly, the minimal sequence epitope was defined as amino acids 5-16 of GV1001, corresponding to amino acids 615-626 of hTERT.

T-Cells Expressing hTERT-TCR-1 Reduce Tumour Load In Vivo

As shown in FIG. 6A, a construct was generated which co-expressed a modified MHC II invariant chain and a luciferase-GFP fusion protein in a single ORF. The MHC II invariant chain was modified by replacement of the CLIP (Class 11-associated invariant chain peptide) sequence with GV1001. The GV1001-modified invariant chain was encoded at the N-terminus of the ORF, followed by a luciferase-GFP fusion protein. The GV1001-modified invariant chain and luciferase-GFP fusion were separated by a self-cleaving 2A linker. Within the luciferase-GFP fusion protein, firefly luciferase was located at the N-terminus and GFP at the C-terminus, separated by a troponin-C linker. This is a highly flexible sequence, preventing disruption of the activity of firefly luciferase or GFP by the other.

Mice were injected with ESTDAB-039 tumour cells transfected with the SW1000 construct. These thus present the GV1001 peptide, and tumour load can be readily determined by bioluminescence measurements. Two days after injection of the mice with the tumour cells, they were injected with a first infusion of T-cells, which had either been transfected with hTERT-TCR-1 or mock-transfected. Six further T-cell infusions were given to the mice over the course of the next fortnight, and tumour load measured at regular time-points. As shown in FIG. 6C, mice administered T-cells transfected with hTERT-TCR-1 displayed, on average, a much lower tumour load by day 23 than did the mice administered mock transfected T-cells, demonstrating that in vivo T-cells expressing hTERT-TCR-1 can significantly slow progression of hTERT+ cancers, indicating the strong therapeutic potential of the TCR.

hTERT-TCR-1 T-Cells Recognise and Specifically Kill Tumour Cells

The ability of hTERT-TCR-1-expressing T-cells to lyse antigen-positive targets was evaluated using bioluminescence (BLI) cytotoxicity assays (FIG. 7A). In these investigations hTERT-TCR-1 TCR mRNA-electroporated or transduced T-cells as well as mock-transfected T-cells were incubated in the presence of HLA-DP04+ B-cell lymphoma (Granta-519) or Epstein Barr Virus-transformed lymphoblastoid cell lines (EBV-LCLs) stably transduced with the agonist li-hTERT. Both transduced and electroporated hTERT-TCR-1-expressing T-cells were able to kill the vast majority of the two target cells compared to the mock controls (FIG. 7A).

Additionally, the cytotoxic capabilities of hTERT-TCR-1 T-cells were evaluated through Annexin V real time assays. hTERT-TCR-1 transduced or electroporated donor T-cells, the original patient T-cell clone (from which the TCR was extracted) and mock-transfected T-cells were co-cultured with ascites cells extracted from the peritoneum of the pancreatic cancer patient from which the original TCR was sourced. hTERT-TCR-1 T-cells showed lysis of ascites cells compared to the mock control, demonstrating the recognition of the naturally occurring antigen by the TCR (FIG. 7B).

hTERT-TCR-1 T-Cells Improve Survival of Melanoma-Carrying Mice

NSG mice were injected intraperitoneally (i.p.) with the melanoma cancer cell line ESTDAB-1000, stably transduced with li-hTERT. After confirmation of tumour engraftment (at 3 days), mice were randomised and injected i.p. 4 times with $10^7$ effector cells every other day (FIG. 8A). Treatment with hTERT-TCR-1 transduced cells significantly reduced the tumour load compared to mock-transfected T-cells (FIG. 8B) and greatly enhanced survival of the treated mice (FIG. 8C).

hTERT-TCR-1 T-Cells do not React Against Bone Marrow

As hematological stem cells have been reported to express telomerase but exhibit relatively low levels of MHC class II compared to other cell types, potential reactivity of hTERT-TCR-1-expressing T-cells against this compartment was evaluated. This was investigated by probing the colony-forming ability of bone marrow progenitor cells in the presence of the hTERT-TCR-1 T-cells. A colony forming unit assay was used to demonstrate that myeloid and erythroid colony formation in HLA-DP04+ bone marrow samples was not affected by co-culture with hTERT-TCR-1-expressing T-cells at an Effector:Target (E:T) ratio of 10:1 (FIG. 9, exemplar donor). These observations demonstrated that hTERT-specific TCR redirected T-cells were not cytotoxic against autologous stem cells from bone marrow (4 donors showed similar results).

hTERT-TCR-1-Expressing T-Cells do not Show Alloreactivity Against a PBMC Panel

Most human TCRs only recognise and bind effectively to specific self-HLA molecules loaded with peptides. A small proportion (less than 10%) of TCRs have the ability to recognise non-self HLA molecules. This phenomenon is termed "alloreactivity". In a study evaluating the potential for an alloreactive response, hTERT-TCR-1-expressing T-cells were exposed to a range of MHC class I and MHC class II typed peripheral blood mononuclear cells (PBMCs) covering the majority (>90%) of HLA-types in the population (FIG. 10). Following exposure, T-cell target recognition was assessed according to whether exposure to the PBMCs led to activation (determined by intracellular cytokine production). The data show that hTERT-TCR-1 transduced T-cells do not recognise this panel of PBMCs, and thus do not demonstrate alloreactivity. As a positive control, hTERT-TCR-1-expressing T-cells were shown to be functional when exposed to specific peptide loaded onto HLA-DPB1*0401 PBMCs with sensitivity down to a concentration of at least 100 nM peptide.

The invention claimed is:

1. An isolated nucleic acid molecule encoding a T-cell receptor (TCR) molecule capable of binding an hTERT peptide comprising the amino acid sequence set forth in SEQ ID NO: 1 when the peptide is presented by an HLA-DP4 Class II Major Histocompatibility Complex (MHC), wherein the TCR molecule comprises a first polypeptide comprising a variable region of an α-chain and a constant region of an α-chain of a TCR and a second polypeptide comprising a variable region of a β-chain and a constant region of a β-chain of a TCR, and wherein:
   (a) the variable region of an α-chain comprises the amino acid sequence set forth in SEQ ID NO: 9, comprising CDR sequences CDR1, CDR2 and CDR3 which respectively comprise the amino acid sequences set forth in SEQ ID NOs: 2, 3 and 4, and the constant region of an α-chain comprises the amino acid sequence set forth in SEQ ID NO:12; and
   (b) the variable region of a β-chain comprises the amino acid sequence set forth in SEQ ID NO: 11, comprising CDR sequences CDR1, CDR2 and CDR3 which respectively comprise the sequences set forth in SEQ ID NOs: 5, 6 and 7, and the constant region of a β-chain comprises the amino acid sequence set forth in SEQ ID NO:13;
   wherein the TCR molecule is encoded as a single chain comprising the first polypeptide linked to the second polypeptide; and
   wherein the TCR molecule, when expressed by an immune effector cell, is located on the surface of the cell.

2. The isolated nucleic acid molecule of claim 1, wherein the the first and second polypeptides of the TCR molecule are joined by a self-splicing linker, wherein the self-splicing linker is a 2A peptide.

3. The isolated nucleic acid molecule of claim 2, wherein the self-splicing linker is a 2A peptide comprising the amino acid sequence set forth in SEQ ID NO: 18.

4. The isolated nucleic acid molecule of claim 1, wherein the amino acid sequence of the first polypeptide comprises the amino acid sequence set forth in SEQ ID NO: 38; and
   the amino acid sequence of the second polypeptide comprises the amino acid sequence set forth in SEQ ID NO: 40.

5. The isolated nucleic acid molecule of claim 4, wherein the amino acid sequence of the first polypeptide comprises the amino acid sequence set forth in SEQ ID NO: 15 and the amino acid sequence of the second polypeptide comprises the amino acid sequence set forth in SEQ ID NO: 17.

6. The isolated nucleic acid molecule of claim 1, wherein the nucleic acid is DNA or RNA.

7. An isolated recombinant construct comprising the isolated nucleic acid molecule of claim 1 linked to a nucleic acid sequence which is heterologous to the nucleic acid molecule.

8. An isolated vector comprising the isolated nucleic acid molecule of claim 1.

9. The isolated vector of claim 8, wherein the vector is:
   (i) an expression vector or a cloning vector; and/or
   (ii) a viral vector; and/or
   (iii) an mRNA vector.

10. An isolated host cell comprising:
    (i) the isolated nucleic acid molecule of claim 1;
    (ii) a recombinant construct comprising the isolated nucleic acid molecule of claim 1 linked to a nucleic acid sequence which is heterologous to the nucleic acid molecule; or
    (iii) a vector comprising the isolated nucleic acid molecule of claim 1.

11. The isolated host cell of claim 10, wherein the host cell is a cytotoxic immune effector cell, and said TCR molecule comprises a transmembrane domain and is expressed on the surface of the cytotoxic immune effector cell.

12. The isolated host cell of claim 11, wherein the cytotoxic immune effector cell is a T-cell or an NK cell.

13. A composition comprising the isolated host cell of claim 11 and at least one physiologically-acceptable diluent, carrier or excipient.

14. A kit comprising a first vector and a second vector, wherein;
    (i) the first vector comprises a nucleic acid molecule encoding a first polypeptide comprising a variable region of an α-chain and a constant region of an α-chain of a TCR, wherein the variable region of the α-chain comprises the amino acid sequence set forth in SEQ ID NO: 9 comprising CDR sequences CDR1, CDR2 and CDR3 which respectively comprise the amino acid sequences set forth in SEQ ID NOs: 2, 3 and 4; and the constant region of an α-chain comprises the amino acid sequence set forth in SEQ ID NO: 12; and
    (ii) the second vector comprises a nucleic acid molecule encoding a second polypeptide comprising a variable region of a β-chain and a constant region of a β-chain of a TCR, wherein the variable region of a β-chain comprises the amino acid sequence set forth in SEQ ID NO: 11 comprising CDR sequences CDR1, CDR2 and CDR3 which respectively comprise the sequences set forth in SEQ ID NOs: 5, 6 and 7 and 12, and the constant region of a β-chain comprises the amino acid sequence set forth in SEQ ID NO: 13.

* * * * *

```
                           SEQUENCE LISTING

<160> NUMBER OF SEQ ID NOS: 68

<210> SEQ ID NO 1
<211> LENGTH: 12
<212> TYPE: PRT
<213> ORGANISM: Homo sapiens

<400> SEQUENCE: 1

Ala Leu Leu Thr Ser Arg Leu Arg Phe Ile Pro Lys
1               5                   10

<210> SEQ ID NO 2
<211> LENGTH: 7
<212> TYPE: PRT
<213> ORGANISM: Homo sapiens

<400> SEQUENCE: 2

Thr Ser Asp Gln Ser Tyr Gly
1               5

<210> SEQ ID NO 3
<211> LENGTH: 8
<212> TYPE: PRT
<213> ORGANISM: Homo sapiens

<400> SEQUENCE: 3

Gln Gly Ser Tyr Asp Glu Gln Asn
1               5

<210> SEQ ID NO 4
<211> LENGTH: 15
<212> TYPE: PRT
<213> ORGANISM: Homo sapiens

<400> SEQUENCE: 4

Cys Ala Met Arg Glu Ile Tyr Ser Ser Ala Ser Lys Ile Ile Phe
1               5                   10                  15

<210> SEQ ID NO 5
<211> LENGTH: 5
<212> TYPE: PRT
<213> ORGANISM: Homo sapiens

<400> SEQUENCE: 5

Ser Gly His Thr Ala
1               5

<210> SEQ ID NO 6
<211> LENGTH: 6
<212> TYPE: PRT
<213> ORGANISM: Homo sapiens

<400> SEQUENCE: 6

Phe Gln Gly Asn Ser Ala
1               5

<210> SEQ ID NO 7
<211> LENGTH: 16
<212> TYPE: PRT
<213> ORGANISM: Homo sapiens
```

```
<400> SEQUENCE: 7

Cys Ala Ser Ser Leu Gly Gly Gly Asp His Thr Asp Thr Gln Tyr Phe
1               5                   10                  15

<210> SEQ ID NO 8
<211> LENGTH: 112
<212> TYPE: PRT
<213> ORGANISM: Homo sapiens

<400> SEQUENCE: 8

Ile Thr Gln Thr Gln Pro Gly Met Phe Val Gln Glu Lys Glu Ala Val
1               5                   10                  15

Thr Leu Asp Cys Thr Tyr Asp Thr Ser Asp Gln Ser Tyr Gly Leu Phe
                20                  25                  30

Trp Tyr Lys Gln Pro Ser Ser Gly Glu Met Ile Phe Leu Ile Tyr Gln
            35                  40                  45

Gly Ser Tyr Asp Glu Gln Asn Ala Thr Glu Gly Arg Tyr Ser Leu Asn
        50                  55                  60

Phe Gln Lys Ala Arg Lys Ser Ala Asn Leu Val Ile Ser Ala Ser Gln
65                  70                  75                  80

Leu Gly Asp Ser Ala Met Tyr Phe Cys Ala Met Arg Glu Ile Tyr Ser
                85                  90                  95

Ser Ala Ser Lys Ile Ile Phe Gly Ser Gly Thr Arg Leu Ser Ile Arg
                100                 105                 110

<210> SEQ ID NO 9
<211> LENGTH: 115
<212> TYPE: PRT
<213> ORGANISM: Homo sapiens

<400> SEQUENCE: 9

Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Gln Ser Tyr
                20                  25                  30

Gly Leu Phe Trp Tyr Lys Gln Pro Ser Ser Gly Glu Met Ile Phe Leu
            35                  40                  45

Ile Tyr Gln Gly Ser Tyr Asp Glu Gln Asn Ala Thr Glu Gly Arg Tyr
        50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Glu
                85                  90                  95

Ile Tyr Ser Ser Ala Ser Lys Ile Ile Phe Gly Ser Gly Thr Arg Leu
                100                 105                 110

Ser Ile Arg
        115

<210> SEQ ID NO 10
<211> LENGTH: 113
<212> TYPE: PRT
<213> ORGANISM: Homo sapiens

<400> SEQUENCE: 10

Val Ser Gln Ser Pro Ser Asn Lys Val Thr Glu Lys Gly Lys Asp Val
1               5                   10                  15

Glu Leu Arg Cys Asp Pro Ile Ser Gly His Thr Ala Leu Tyr Trp Tyr
                20                  25                  30
```

Arg Gln Ser Leu Gly Gln Gly Leu Glu Phe Leu Ile Tyr Phe Gln Gly
                35                  40                  45

Asn Ser Ala Pro Asp Lys Ser Gly Leu Pro Ser Asp Arg Phe Ser Ala
        50                  55                  60

Glu Arg Thr Gly Gly Ser Val Ser Thr Leu Thr Ile Gln Arg Thr Gln
65                  70                  75                  80

Gln Glu Asp Ser Ala Val Tyr Leu Cys Ala Ser Ser Leu Gly Gly Gly
                85                  90                  95

Asp His Thr Asp Thr Gln Tyr Phe Gly Pro Gly Thr Arg Leu Thr Val
            100                 105                 110

Leu

<210> SEQ ID NO 11
<211> LENGTH: 116
<212> TYPE: PRT
<213> ORGANISM: Homo sapiens

<400> SEQUENCE: 11

Gly Ala Gly Val Ser Gln Ser Pro Ser Asn Lys Val Thr Glu Lys Gly
1               5                   10                  15

Lys Asp Val Glu Leu Arg Cys Asp Pro Ile Ser Gly His Thr Ala Leu
                20                  25                  30

Tyr Trp Tyr Arg Gln Ser Leu Gly Gln Gly Leu Glu Phe Leu Ile Tyr
                35                  40                  45

Phe Gln Gly Asn Ser Ala Pro Asp Lys Ser Gly Leu Pro Ser Asp Arg
        50                  55                  60

Phe Ser Ala Glu Arg Thr Gly Gly Ser Val Ser Thr Leu Thr Ile Gln
65                  70                  75                  80

Arg Thr Gln Gln Glu Asp Ser Ala Val Tyr Leu Cys Ala Ser Ser Leu
                85                  90                  95

Gly Gly Gly Asp His Thr Asp Thr Gln Tyr Phe Gly Pro Gly Thr Arg
            100                 105                 110

Leu Thr Val Leu
        115

<210> SEQ ID NO 12
<211> LENGTH: 142
<212> TYPE: PRT
<213> ORGANISM: Homo sapiens

<400> SEQUENCE: 12

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
                20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Lys Val
            115                 120                 125

Ala Gly Phe Asn Leu Leu Met Thr Leu Arg Leu Trp Ser Ser
    130                 135                 140

<210> SEQ ID NO 13
<211> LENGTH: 179
<212> TYPE: PRT
<213> ORGANISM: Homo sapiens

<400> SEQUENCE: 13

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 14
<211> LENGTH: 274
<212> TYPE: PRT
<213> ORGANISM: Artificial Sequence
<220> FEATURE:
<223> OTHER INFORMATION: Full length hTERT-TCR-1 alpha-chain with
      truncated variable region.

<400> SEQUENCE: 14

Met Ser Leu Ser Ser Leu Leu Lys Val Val Thr Ala Ser Leu Trp Leu
1               5                   10                  15

Gly Pro Gly Ile Ile Thr Gln Thr Gln Pro Gly Met Phe Val Gln Glu
            20                  25                  30

Lys Glu Ala Val Thr Leu Asp Cys Thr Tyr Asp Thr Ser Asp Gln Ser
        35                  40                  45

Tyr Gly Leu Phe Trp Tyr Lys Gln Pro Ser Ser Gly Glu Met Ile Phe
    50                  55                  60

Leu Ile Tyr Gln Gly Ser Tyr Asp Glu Gln Asn Ala Thr Glu Gly Arg
65                  70                  75                  80

Tyr Ser Leu Asn Phe Gln Lys Ala Arg Lys Ser Ala Asn Leu Val Ile
                85                  90                  95

Ser Ala Ser Gln Leu Gly Asp Ser Ala Met Tyr Phe Cys Ala Met Arg

-continued

Glu Ile Tyr Ser Ser Ala Ser Lys Ile Ile Phe Gly Ser Gly Thr Arg
100                 105                 110

Leu Ser Ile Arg Pro Asn Ile Gln Asn Pro Asp Pro Ala Val Tyr Gln
115                 120                 125

Leu Arg Asp Ser Lys Ser Ser Asp Lys Ser Val Cys Leu Phe Thr Asp
130                 135                 140

Phe Asp Ser Gln Thr Asn Val Ser Gln Ser Lys Asp Ser Asp Val Tyr
145                 150                 155                 160

Ile Thr Asp Lys Thr Val Leu Asp Met Arg Ser Met Asp Phe Lys Ser
        165                 170                 175

Asn Ser Ala Val Ala Trp Ser Asn Lys Ser Asp Phe Ala Cys Ala Asn
    180                 185                 190

Ala Phe Asn Asn Ser Ile Ile Pro Glu Asp Thr Phe Phe Pro Ser Pro
195                 200                 205

Glu Ser Ser Cys Asp Val Lys Leu Val Glu Lys Ser Phe Glu Thr Asp
210                 215                 220

Thr Asn Leu Asn Phe Gln Asn Leu Ser Val Ile Gly Phe Arg Ile Leu
225                 230                 235                 240

Leu Leu Lys Val Ala Gly Phe Asn Leu Met Thr Leu Arg Leu Trp
        245                 250                 255

Ser Ser
260                 265                 270

<210> SEQ ID NO 15
<211> LENGTH: 277
<212> TYPE: PRT
<213> ORGANISM: Homo sapiens

<400> SEQUENCE: 15

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Ile Tyr Ser Ser Ala Ser Lys Ile Ile Phe Gly Ser
        115                 120                 125

Gly Thr Arg Leu Ser Ile Arg Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala

```
                195                 200                 205
Cys Ala Asn Ala Phe Asn Asn Ser Ile Ile Pro Glu Asp Thr Phe Phe
210                 215                 220
Pro Ser Pro Glu Ser Ser Cys Asp Val Lys Leu Val Glu Lys Ser Phe
225                 230                 235                 240
Glu Thr Asp Thr Asn Leu Asn Phe Gln Asn Leu Ser Val Ile Gly Phe
                245                 250                 255
Arg Ile Leu Leu Leu Lys Val Ala Gly Phe Asn Leu Leu Met Thr Leu
                260                 265                 270
Arg Leu Trp Ser Ser
                275

<210> SEQ ID NO 16
<211> LENGTH: 311
<212> TYPE: PRT
<213> ORGANISM: Artificial Sequence
<220> FEATURE:
<223> OTHER INFORMATION: Full length hTERT-TCR-1 beta-chain with
      truncated variable region

<400> SEQUENCE: 16

Met Gly Thr Arg Leu Leu Phe Trp Val Ala Phe Cys Leu Leu Gly Ala
1               5                   10                  15
Asp His Thr Val Ser Gln Ser Pro Ser Asn Lys Val Thr Glu Lys Gly
                20                  25                  30
Lys Asp Val Glu Leu Arg Cys Asp Pro Ile Ser Gly His Thr Ala Leu
            35                  40                  45
Tyr Trp Tyr Arg Gln Ser Leu Gly Gln Gly Leu Glu Phe Leu Ile Tyr
        50                  55                  60
Phe Gln Gly Asn Ser Ala Pro Asp Lys Ser Gly Leu Pro Ser Asp Arg
65                  70                  75                  80
Phe Ser Ala Glu Arg Thr Gly Gly Ser Val Ser Thr Leu Thr Ile Gln
                85                  90                  95
Arg Thr Gln Gln Glu Asp Ser Ala Val Tyr Leu Cys Ala Ser Ser Leu
                100                 105                 110
Gly Gly Gly Asp His Thr Asp Thr Gln Tyr Phe Gly Pro Gly Thr Arg
            115                 120                 125
Leu Thr Val Leu Glu Asp Leu Lys Asn Val Phe Pro Pro Glu Val Ala
130                 135                 140
Val Phe Glu Pro Ser Glu Ala Glu Ile Ser His Thr Gln Lys Ala Thr
145                 150                 155                 160
Leu Val Cys Leu Ala Thr Gly Phe Tyr Pro Asp His Val Glu Leu Ser
                165                 170                 175
Trp Trp Val Asn Gly Lys Glu Val His Ser Gly Val Ser Thr Asp Pro
                180                 185                 190
Gln Pro Leu Lys Glu Gln Pro Ala Leu Asn Asp Ser Arg Tyr Cys Leu
            195                 200                 205
Ser Ser Arg Leu Arg Val Ser Ala Thr Phe Trp Gln Asn Pro Arg Asn
        210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
                245                 250                 255
Ala Trp Gly Arg Ala Asp Cys Gly Phe Thr Ser Glu Ser Tyr Gln Gln
                260                 265                 270
```

```
Gly Val Leu Ser Ala Thr Ile Leu Tyr Glu Ile Leu Gly Lys Ala
            275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 17
<211> LENGTH: 314
<212> TYPE: PRT
<213> ORGANISM: Homo sapiens

<400> SEQUENCE: 17

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ser Leu Gly Gly Gly Asp His Thr Asp Thr Gln Tyr Phe Gly Pro
        115                 120                 125

Gly Thr Arg Leu Thr Val Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310

<210> SEQ ID NO 18
```

```
<211> LENGTH: 26
<212> TYPE: PRT
<213> ORGANISM: Unknown
<220> FEATURE:
<223> OTHER INFORMATION: Picornaviridae

<400> SEQUENCE: 18

Arg Ala Lys Arg Gly Ser Gly Ala Thr Asn Phe Ser Leu Leu Lys Gln
1               5                   10                  15

Ala Gly Asp Val Glu Glu Asn Pro Gly Pro
            20                  25

<210> SEQ ID NO 19
<211> LENGTH: 611
<212> TYPE: PRT
<213> ORGANISM: Artificial Sequence
<220> FEATURE:
<223> OTHER INFORMATION: hTERT-TCR-1 scTCR with truncated variable
      regions

<400> SEQUENCE: 19

Met Ser Leu Ser Ser Leu Leu Lys Val Val Thr Ala Ser Leu Trp Leu
1               5                   10                  15

Gly Pro Gly Ile Ile Thr Gln Thr Gln Pro Gly Met Phe Val Gln Glu
            20                  25                  30

Lys Glu Ala Val Thr Leu Asp Cys Thr Tyr Asp Thr Ser Asp Gln Ser
        35                  40                  45

Tyr Gly Leu Phe Trp Tyr Lys Gln Pro Ser Ser Gly Glu Met Ile Phe
    50                  55                  60

Leu Ile Tyr Gln Gly Ser Tyr Asp Glu Gln Asn Ala Thr Glu Gly Arg
65                  70                  75                  80

Tyr Ser Leu Asn Phe Gln Lys Ala Arg Lys Ser Ala Asn Leu Val Ile
                85                  90                  95

Ser Ala Ser Gln Leu Gly Asp Ser Ala Met Tyr Phe Cys Ala Met Arg
            100                 105                 110

Glu Ile Tyr Ser Ser Ala Ser Lys Ile Ile Phe Gly Ser Gly Thr Arg
        115                 120                 125

Leu Ser Ile Arg Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser Arg Ala Lys Arg Gly Ser Gly Ala Thr Asn Phe Ser Leu Leu
        275                 280                 285
```

-continued

```
Lys Gln Ala Gly Asp Val Glu Glu Asn Pro Gly Pro Met Gly Thr Arg
290                 295                 300
Leu Leu Phe Trp Val Ala Phe Cys Leu Leu Gly Ala Asp His Thr Val
305                 310                 315                 320
Ser Gln Ser Pro Ser Asn Lys Val Thr Glu Lys Gly Lys Asp Val Glu
            325                 330                 335
Leu Arg Cys Asp Pro Ile Ser Gly His Thr Ala Leu Tyr Trp Tyr Arg
        340                 345                 350
Gln Ser Leu Gly Gln Gly Leu Glu Phe Leu Ile Tyr Phe Gln Gly Asn
    355                 360                 365
Ser Ala Pro Asp Lys Ser Gly Leu Pro Ser Asp Arg Phe Ser Ala Glu
370                 375                 380
Arg Thr Gly Gly Ser Val Ser Thr Leu Thr Ile Gln Arg Thr Gln Gln
385                 390                 395                 400
Glu Asp Ser Ala Val Tyr Leu Cys Ala Ser Ser Leu Gly Gly Gly Asp
            405                 410                 415
His Thr Asp Thr Gln Tyr Phe Gly Pro Gly Thr Arg Leu Thr Val Leu
        420                 425                 430
Glu Asp Leu Lys Asn Val Phe Pro Pro Glu Val Ala Val Phe Glu Pro
    435                 440                 445
Ser Glu Ala Glu Ile Ser His Thr Gln Lys Ala Thr Leu Val Cys Leu
450                 455                 460
Ala Thr Gly Phe Tyr Pro Asp His Val Glu Leu Ser Trp Trp Val Asn
465                 470                 475                 480
Gly Lys Glu Val His Ser Gly Val Ser Thr Asp Pro Gln Pro Leu Lys
            485                 490                 495
Glu Gln Pro Ala Leu Asn Asp Ser Arg Tyr Cys Leu Ser Ser Arg Leu
        500                 505                 510
Arg Val Ser Ala Thr Phe Trp Gln Asn Pro Arg Asn His Phe Arg Cys
    515                 520                 525
Gln Val Gln Phe Tyr Gly Leu Ser Glu Asn Asp Glu Trp Thr Gln Asp
530                 535                 540
Arg Ala Lys Pro Val Thr Gln Ile Val Ser Ala Glu Ala Trp Gly Arg
545                 550                 555                 560
Ala Asp Cys Gly Phe Thr Ser Glu Ser Tyr Gln Gln Gly Val Leu Ser
            565                 570                 575
Ala Thr Ile Leu Tyr Glu Ile Leu Leu Gly Lys Ala Thr Leu Tyr Ala
        580                 585                 590
Val Leu Val Ser Ala Leu Val Leu Met Ala Met Val Lys Arg Lys Asp
    595                 600                 605
Ser Arg Gly
    610

<210> SEQ ID NO 20
<211> LENGTH: 617
<212> TYPE: PRT
<213> ORGANISM: Artificial Sequence
<220> FEATURE:
<223> OTHER INFORMATION: hTERT-TCR-1 scTCR

<400> SEQUENCE: 20

Met Ser Leu Ser Ser Leu Leu Lys Val Val Thr Ala Ser Leu Trp Leu
1               5                   10                  15
Gly Pro Gly Ile Ala Gln Lys Ile Thr Gln Thr Gln Pro Gly Met Phe
            20                  25                  30
```

```
Val Gln Glu Lys Glu Ala Val Thr Leu Asp Cys Thr Tyr Asp Thr Ser
             35                  40                  45

Asp Gln Ser Tyr Gly Leu Phe Trp Tyr Lys Gln Pro Ser Ser Gly Glu
 50                  55                  60

Met Ile Phe Leu Ile Tyr Gln Gly Ser Tyr Asp Glu Gln Asn Ala Thr
 65                  70                  75                  80

Glu Gly Arg Tyr Ser Leu Asn Phe Gln Lys Ala Arg Lys Ser Ala Asn
             85                  90                  95

Leu Val Ile Ser Ala Ser Gln Leu Gly Asp Ser Ala Met Tyr Phe Cys
            100                 105                 110

Ala Met Arg Glu Ile Tyr Ser Ser Ala Ser Lys Ile Ile Phe Gly Ser
            115                 120                 125

Gly Thr Arg Leu Ser Ile Arg Pro Asn Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Thr Val Leu Asp Met Arg Ser Met Asp
            180                 185                 190

Phe Lys Ser Asn Ser Ala Val Ala Trp Ser Asn Lys Ser Asp Phe Ala
            195                 200                 205

Cys Ala Asn Ala Phe Asn Asn Ser Ile Ile Pro Glu Asp Thr Phe Phe
            210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser Arg Ala Lys Arg Gly Ser Gly Ala Thr Asn Phe
            275                 280                 285

Ser Leu Leu Lys Gln Ala Gly Asp Val Glu Glu Asn Pro Gly Pro Met
290                 295                 300

Gly Thr Arg Leu Leu Phe Trp Val Ala Phe Cys Leu Leu Gly Ala Asp
305                 310                 315                 320

His Thr Gly Ala Gly Val Ser Gln Ser Pro Ser Asn Lys Val Thr Glu
                325                 330                 335

Lys Gly Lys Asp Val Glu Leu Arg Cys Asp Pro Ile Ser Gly His Thr
            340                 345                 350

Ala Leu Tyr Trp Tyr Arg Gln Ser Leu Gly Gln Gly Leu Glu Phe Leu
            355                 360                 365

Ile Tyr Phe Gln Gly Asn Ser Ala Pro Asp Lys Ser Gly Leu Pro Ser
            370                 375                 380

Asp Arg Phe Ser Ala Glu Arg Thr Gly Gly Ser Val Ser Thr Leu Thr
385                 390                 395                 400

Ile Gln Arg Thr Gln Gln Glu Asp Ser Ala Val Tyr Leu Cys Ala Ser
                405                 410                 415

Ser Leu Gly Gly Gly Asp His Thr Asp Thr Gln Tyr Phe Gly Pro Gly
            420                 425                 430

Thr Arg Leu Thr Val Leu Glu Asp Leu Lys Asn Val Phe Pro Pro Glu
            435                 440                 445

Val Ala Val Phe Glu Pro Ser Glu Ala Glu Ile Ser His Thr Gln Lys
```

```
                    450                 455                 460
Ala Thr Leu Val Cys Leu Ala Thr Gly Phe Tyr Pro Asp His Val Glu
465                 470                 475                 480

Leu Ser Trp Trp Val Asn Gly Lys Glu Val His Ser Gly Val Ser Thr
                    485                 490                 495

Asp Pro Gln Pro Leu Lys Glu Gln Pro Ala Leu Asn Asp Ser Arg Tyr
                500                 505                 510

Cys Leu Ser Ser Arg Leu Arg Val Ser Ala Thr Phe Trp Gln Asn Pro
                515                 520                 525

Arg Asn His Phe Arg Cys Gln Val Gln Phe Tyr Gly Leu Ser Glu Asn
            530                 535                 540

Asp Glu Trp Thr Gln Asp Arg Ala Lys Pro Val Thr Gln Ile Val Ser
545                 550                 555                 560

Ala Glu Ala Trp Gly Arg Ala Asp Cys Gly Phe Thr Ser Glu Ser Tyr
                565                 570                 575

Gln Gln Gly Val Leu Ser Ala Thr Ile Leu Tyr Glu Ile Leu Leu Gly
                580                 585                 590

Lys Ala Thr Leu Tyr Ala Val Leu Val Ser Ala Leu Val Leu Met Ala
                595                 600                 605

Met Val Lys Arg Lys Asp Ser Arg Gly
610                 615

<210> SEQ ID NO 21
<211> LENGTH: 96
<212> TYPE: PRT
<213> ORGANISM: Artificial Sequence
<220> FEATURE:
<223> OTHER INFORMATION: Soluble truncated human alpha-chain constant
      region containing cysteine substitution.

<400> SEQUENCE: 21

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
                20                  25                  30

Thr Asn Val Ser Gln Ser Lys Asp Ser Asp Val Tyr Ile Thr Asp Lys
            35                  40                  45

Cys Val Leu Asp Met Arg Ser Met Asp Phe Lys Ser Asn Ser Ala Val
        50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

<210> SEQ ID NO 22
<211> LENGTH: 132
<212> TYPE: PRT
<213> ORGANISM: Artificial Sequence
<220> FEATURE:
<223> OTHER INFORMATION: Soluble truncated human beta-chain constant
      region containing cysteine substitution.

<400> SEQUENCE: 22

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
```

```
                35                  40                  45
Gly Lys Glu Val His Ser Gly Val Cys Thr Asp Pro Gln Pro Leu Lys
             50                  55                  60
Glu Gln Pro Ala Leu Asn Asp Ser Arg Tyr Cys Leu Ser Ser Arg Leu
65                  70                  75                  80
Arg Val Ser Ala Thr Phe Trp Gln Asn Pro Arg Asn His Phe Arg Cys
                 85                  90                  95
Gln Val Gln Phe Tyr Gly Leu Ser Glu Asn Asp Glu Trp Thr Gln Asp
                100                 105                 110
Arg Ala Lys Pro Val Thr Gln Ile Val Ser Ala Glu Ala Trp Gly Arg
                115                 120                 125
Ala Asp Cys Gly
        130

<210> SEQ ID NO 23
<211> LENGTH: 228
<212> TYPE: PRT
<213> ORGANISM: Artificial Sequence
<220> FEATURE:
<223> OTHER INFORMATION: Soluble hTERT-TCR-1 alpha-chain, with truncated
      variable region and truncated constant regioncontaining cysteine
      substitution.

<400> SEQUENCE: 23

Met Ser Leu Ser Ser Leu Leu Lys Val Val Thr Ala Ser Leu Trp Leu
1               5                  10                  15
Gly Pro Gly Ile Ile Thr Gln Thr Gln Pro Gly Met Phe Val Gln Glu
                20                  25                  30
Lys Glu Ala Val Thr Leu Asp Cys Thr Tyr Asp Thr Ser Asp Gln Ser
             35                  40                  45
Tyr Gly Leu Phe Trp Tyr Lys Gln Pro Ser Ser Gly Glu Met Ile Phe
         50                  55                  60
Leu Ile Tyr Gln Gly Ser Tyr Asp Glu Gln Asn Ala Thr Glu Gly Arg
65                  70                  75                  80
Tyr Ser Leu Asn Phe Gln Lys Ala Arg Lys Ser Ala Asn Leu Val Ile
                 85                  90                  95
Ser Ala Ser Gln Leu Gly Asp Ser Ala Met Tyr Phe Cys Ala Met Arg
                100                 105                 110
Glu Ile Tyr Ser Ser Ala Ser Lys Ile Ile Phe Gly Ser Gly Thr Arg
                115                 120                 125
Leu Ser Ile Arg Pro Asn Ile Gln Asn Pro Asp Pro Ala Val Tyr Gln
         130                 135                 140
Leu Arg Asp Ser Lys Ser Ser Asp Lys Ser Val Cys Leu Phe Thr Asp
145                 150                 155                 160
Phe Asp Ser Gln Thr Asn Val Ser Gln Ser Lys Asp Ser Asp Val Tyr
                165                 170                 175
Ile Thr Asp Lys Cys Val Leu Asp Met Arg Ser Met Asp Phe Lys Ser
                180                 185                 190
Asn Ser Ala Val Ala Trp Ser Asn Lys Ser Asp Phe Ala Cys Ala Asn
             195                 200                 205
Ala Phe Asn Asn Ser Ile Ile Pro Glu Asp Thr Phe Phe Pro Ser Pro
         210                 215                 220
Glu Ser Ser Cys
225

<210> SEQ ID NO 24
```

```
<211> LENGTH: 231
<212> TYPE: PRT
<213> ORGANISM: Artificial Sequence
<220> FEATURE:
<223> OTHER INFORMATION: Soluble hTERT-TCR-1 alpha-chain with full
      length variable region and truncated constant region containing
      cysteine substitution.

<400> SEQUENCE: 24

Met Ser Leu Ser Ser Leu Leu Lys Val Thr Ala Ser Leu Trp Leu
1               5                   10                  15

Gly Pro Gly Ile Ala Gln Lys Ile Thr Gln Thr Gln Pro Gly Met Phe
                20                  25                  30

Val Gln Glu Lys Glu Ala Val Thr Leu Asp Cys Thr Tyr Asp Thr Ser
            35                  40                  45

Asp Gln Ser Tyr Gly Leu Phe Trp Tyr Lys Gln Pro Ser Ser Gly Glu
        50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Ile Tyr Ser Ser Ala Ser Lys Ile Ile Phe Gly Ser
        115                 120                 125

Gly Thr Arg Leu Ser Ile Arg Pro Asn Ile Gln Asn Pro Asp Pro Ala
130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Cys Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys
225                 230

<210> SEQ ID NO 25
<211> LENGTH: 264
<212> TYPE: PRT
<213> ORGANISM: Artificial Sequence
<220> FEATURE:
<223> OTHER INFORMATION: Soluble hTERT-TCR-1 beta-chain with truncated
      variable region and truncated constant region containing cysteine
      substitution.

<400> SEQUENCE: 25

Met Gly Thr Arg Leu Leu Phe Trp Val Ala Phe Cys Leu Leu Gly Ala
1               5                   10                  15

Asp His Thr Val Ser Gln Ser Pro Ser Asn Lys Val Thr Glu Lys Gly
                20                  25                  30

Lys Asp Val Glu Leu Arg Cys Asp Pro Ile Ser Gly His Thr Ala Leu
            35                  40                  45

Tyr Trp Tyr Arg Gln Ser Leu Gly Gln Gly Leu Glu Phe Leu Ile Tyr
        50                  55                  60
```

Phe Gln Gly Asn Ser Ala Pro Asp Lys Ser Gly Leu Pro Ser Asp Arg
65                  70                  75                  80

Phe Ser Ala Glu Arg Thr Gly Gly Ser Val Ser Thr Leu Thr Ile Gln
                85                  90                  95

Arg Thr Gln Gln Glu Asp Ser Ala Val Tyr Leu Cys Ala Ser Ser Leu
            100                 105                 110

Gly Gly Gly Asp His Thr Asp Thr Gln Tyr Phe Gly Pro Gly Thr Arg
            115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly
            260

<210> SEQ ID NO 26
<211> LENGTH: 267
<212> TYPE: PRT
<213> ORGANISM: Artificial Sequence
<220> FEATURE:
<223> OTHER INFORMATION: Soluble hTERT-TCR-1 beta-chain with full-length
      variable region and truncated constant region containing cysteine
      substitution.

<400> SEQUENCE: 26

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ser Leu Gly Gly Gly Asp His Thr Asp Thr Gln Tyr Phe Gly Pro
            115                 120                 125

Gly Thr Arg Leu Thr Val Leu Glu Asp Leu Lys Asn Val Phe Pro Pro
    130                 135                 140

Glu Val Ala Val Phe Glu Pro Ser Glu Ala Glu Ile Ser His Thr Gln

```
145                 150                 155                 160
Lys Ala Thr Leu Val Cys Leu Ala Thr Gly Phe Tyr Pro Asp His Val
                165                 170                 175
Glu Leu Ser Trp Trp Val Asn Gly Lys Glu Val His Ser Gly Val Cys
            180                 185                 190
Thr Asp Pro Gln Pro Leu Lys Glu Gln Pro Ala Leu Asn Asp Ser Arg
        195                 200                 205
Tyr Cys Leu Ser Ser Arg Leu Arg Val Ser Ala Thr Phe Trp Gln Asn
    210                 215                 220
Pro Arg Asn His Phe Arg Cys Gln Val Gln Phe Tyr Gly Leu Ser Glu
225                 230                 235                 240
Asn Asp Glu Trp Thr Gln Asp Arg Ala Lys Pro Val Thr Gln Ile Val
                245                 250                 255
Ser Ala Glu Ala Trp Gly Arg Ala Asp Cys Gly
            260                 265

<210> SEQ ID NO 27
<211> LENGTH: 518
<212> TYPE: PRT
<213> ORGANISM: Artificial Sequence
<220> FEATURE:
<223> OTHER INFORMATION: Soluble hTERT-TCR-1 scTCR with truncated
      variable regions.

<400> SEQUENCE: 27

Met Ser Leu Ser Ser Leu Leu Lys Val Val Thr Ala Ser Leu Trp Leu
1               5                   10                  15
Gly Pro Gly Ile Ile Thr Gln Thr Gln Pro Gly Met Phe Val Gln Glu
            20                  25                  30
Lys Glu Ala Val Thr Leu Asp Cys Thr Tyr Asp Thr Ser Asp Gln Ser
        35                  40                  45
Tyr Gly Leu Phe Trp Tyr Lys Gln Pro Ser Ser Gly Glu Met Ile Phe
    50                  55                  60
Leu Ile Tyr Gln Gly Ser Tyr Asp Glu Gln Asn Ala Thr Glu Gly Arg
65                  70                  75                  80
Tyr Ser Leu Asn Phe Gln Lys Ala Arg Lys Ser Ala Asn Leu Val Ile
                85                  90                  95
Ser Ala Ser Gln Leu Gly Asp Ser Ala Met Tyr Phe Cys Ala Met Arg
            100                 105                 110
Glu Ile Tyr Ser Ser Ala Ser Lys Ile Ile Phe Gly Ser Gly Thr Arg
        115                 120                 125
Leu Ser Ile Arg Pro Asn Ile Gln Asn Pro Asp Pro Ala Val Tyr Gln
    130                 135                 140
Leu Arg Asp Ser Lys Ser Ser Asp Lys Ser Val Cys Leu Phe Thr Asp
145                 150                 155                 160
Phe Asp Ser Gln Thr Asn Val Ser Gln Ser Lys Asp Ser Asp Val Tyr
                165                 170                 175
Ile Thr Asp Lys Cys Val Leu Asp Met Arg Ser Met Asp Phe Lys Ser
            180                 185                 190
Asn Ser Ala Val Ala Trp Ser Asn Lys Ser Asp Phe Ala Cys Ala Asn
        195                 200                 205
Ala Phe Asn Asn Ser Ile Ile Pro Glu Asp Thr Phe Phe Pro Ser Pro
    210                 215                 220
Glu Ser Ser Cys Arg Ala Lys Arg Gly Ser Gly Ala Thr Asn Phe Ser
225                 230                 235                 240
```

```
Leu Leu Lys Gln Ala Gly Asp Val Glu Asn Pro Gly Pro Met Gly
            245                 250                 255

Thr Arg Leu Leu Phe Trp Val Ala Phe Cys Leu Leu Gly Ala Asp His
        260                 265                 270

Thr Val Ser Gln Ser Pro Ser Asn Lys Val Thr Glu Lys Gly Lys Asp
        275                 280                 285

Val Glu Leu Arg Cys Asp Pro Ile Ser Gly His Thr Ala Leu Tyr Trp
    290                 295                 300

Tyr Arg Gln Ser Leu Gly Gln Gly Leu Glu Phe Leu Ile Tyr Phe Gln
305                 310                 315                 320

Gly Asn Ser Ala Pro Asp Lys Ser Gly Leu Pro Ser Asp Arg Phe Ser
            325                 330                 335

Ala Glu Arg Thr Gly Gly Ser Val Ser Thr Leu Thr Ile Gln Arg Thr
        340                 345                 350

Gln Gln Glu Asp Ser Ala Val Tyr Leu Cys Ala Ser Ser Leu Gly Gly
        355                 360                 365

Gly Asp His Thr Asp Thr Gln Tyr Phe Gly Pro Gly Thr Arg Leu Thr
    370                 375                 380

Val Leu Glu Asp Leu Lys Asn Val Phe Pro Pro Glu Val Ala Val Phe
385                 390                 395                 400

Glu Pro Ser Glu Ala Glu Ile Ser His Thr Gln Lys Ala Thr Leu Val
            405                 410                 415

Cys Leu Ala Thr Gly Phe Tyr Pro Asp His Val Glu Leu Ser Trp Trp
        420                 425                 430

Val Asn Gly Lys Glu Val His Ser Gly Val Cys Thr Asp Pro Gln Pro
        435                 440                 445

Leu Lys Glu Gln Pro Ala Leu Asn Asp Ser Arg Tyr Cys Leu Ser Ser
    450                 455                 460

Arg Leu Arg Val Ser Ala Thr Phe Trp Gln Asn Pro Arg Asn His Phe
465                 470                 475                 480

Arg Cys Gln Val Gln Phe Tyr Gly Leu Ser Glu Asn Asp Glu Trp Thr
            485                 490                 495

Gln Asp Arg Ala Lys Pro Val Thr Gln Ile Val Ser Ala Glu Ala Trp
        500                 505                 510

Gly Arg Ala Asp Cys Gly
        515

<210> SEQ ID NO 28
<211> LENGTH: 524
<212> TYPE: PRT
<213> ORGANISM: Artificial Sequence
<220> FEATURE:
<223> OTHER INFORMATION: Soluble hTERT-TCR-1 scTCR with full-length
      variable regions.

<400> SEQUENCE: 28

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80
```

```
Glu Gly Arg Tyr Ser Leu Asn Phe Gln Lys Ala Arg Lys Ser Ala Asn
                 85                  90                  95
Leu Val Ile Ser Ala Ser Gln Leu Gly Asp Ser Ala Met Tyr Phe Cys
            100                 105                 110
Ala Met Arg Glu Ile Tyr Ser Ala Ser Lys Ile Ile Phe Gly Ser
        115                 120                 125
Gly Thr Arg Leu Ser Ile Arg Pro Asn Ile Gln Asn Pro Asp Pro Ala
130                 135                 140
Val Tyr Gln Leu Arg Asp Ser Lys Ser Ser Asp Lys Ser Val Cys Leu
145                 150                 155                 160
Phe Thr Asp Phe Asp Ser Gln Thr Asn Val Ser Gln Ser Lys Asp Ser
                165                 170                 175
Asp Val Tyr Ile Thr Asp Lys Cys Val Leu Asp Met Arg Ser Met Asp
                180                 185                 190
Phe Lys Ser Asn Ser Ala Val Ala Trp Ser Asn Lys Ser Asp Phe Ala
            195                 200                 205
Cys Ala Asn Ala Phe Asn Asn Ser Ile Ile Pro Glu Asp Thr Phe Phe
210                 215                 220
Pro Ser Pro Glu Ser Ser Cys Arg Ala Lys Arg Gly Ser Gly Ala Thr
225                 230                 235                 240
Asn Phe Ser Leu Leu Lys Gln Ala Gly Asp Val Glu Glu Asn Pro Gly
                245                 250                 255
Pro Met Gly Thr Arg Leu Leu Phe Trp Val Ala Phe Cys Leu Leu Gly
                260                 265                 270
Ala Asp His Thr Gly Ala Gly Val Ser Gln Ser Pro Ser Asn Lys Val
            275                 280                 285
Thr Glu Lys Gly Lys Asp Val Glu Leu Arg Cys Asp Pro Ile Ser Gly
            290                 295                 300
His Thr Ala Leu Tyr Trp Tyr Arg Gln Ser Leu Gly Gln Gly Leu Glu
305                 310                 315                 320
Phe Leu Ile Tyr Phe Gln Gly Asn Ser Ala Pro Asp Lys Ser Gly Leu
                325                 330                 335
Pro Ser Asp Arg Phe Ser Ala Glu Arg Thr Gly Gly Ser Val Ser Thr
                340                 345                 350
Leu Thr Ile Gln Arg Thr Gln Gln Glu Asp Ser Ala Val Tyr Leu Cys
            355                 360                 365
Ala Ser Ser Leu Gly Gly Gly Asp His Thr Asp Thr Gln Tyr Phe Gly
        370                 375                 380
Pro Gly Thr Arg Leu Thr Val Leu Glu Asp Leu Lys Asn Val Phe Pro
385                 390                 395                 400
Pro Glu Val Ala Val Phe Glu Pro Ser Glu Ala Glu Ile Ser His Thr
                405                 410                 415
Gln Lys Ala Thr Leu Val Cys Leu Ala Thr Gly Phe Tyr Pro Asp His
            420                 425                 430
Val Glu Leu Ser Trp Trp Val Asn Gly Lys Glu Val His Ser Gly Val
            435                 440                 445
Cys Thr Asp Pro Gln Pro Leu Lys Glu Gln Pro Ala Leu Asn Asp Ser
450                 455                 460
Arg Tyr Cys Leu Ser Ser Arg Leu Arg Val Ser Ala Thr Phe Trp Gln
465                 470                 475                 480
Asn Pro Arg Asn His Phe Arg Cys Gln Val Gln Phe Tyr Gly Leu Ser
                485                 490                 495
```

```
Glu Asn Asp Glu Trp Thr Gln Asp Arg Ala Lys Pro Val Thr Gln Ile
            500                 505                 510

Val Ser Ala Glu Ala Trp Gly Arg Ala Asp Cys Gly
        515                 520
```

<210> SEQ ID NO 29
<211> LENGTH: 96
<212> TYPE: PRT
<213> ORGANISM: Homo sapiens

<400> SEQUENCE: 29

```
Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95
```

<210> SEQ ID NO 30
<211> LENGTH: 132
<212> TYPE: PRT
<213> ORGANISM: Homo sapiens

<400> SEQUENCE: 30

```
Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly
    130
```

<210> SEQ ID NO 31
<211> LENGTH: 20
<212> TYPE: PRT
<213> ORGANISM: Homo sapiens

<400> SEQUENCE: 31

```
Met Ser Leu Ser Ser Leu Leu Lys Val Val Thr Ala Ser Leu Trp Leu
1               5                   10                  15

Gly Pro Gly Ile
```

-continued

```
<210> SEQ ID NO 32
<211> LENGTH: 19
<212> TYPE: PRT
<213> ORGANISM: Homo sapiens

<400> SEQUENCE: 32

Met Gly Thr Arg Leu Leu Phe Trp Val Ala Phe Cys Leu Leu Gly Ala
1               5                   10                  15

Asp His Thr

<210> SEQ ID NO 33
<211> LENGTH: 233
<212> TYPE: PRT
<213> ORGANISM: Artificial Sequence
<220> FEATURE:
<223> OTHER INFORMATION: Mature soluble hTERT-TCR-1 alpha-chain with
      truncated variable region, cysteine-substituted constant region
      and residual 2A amino acids at C-terminus.

<400> SEQUENCE: 33

Ile Thr Gln Thr Gln Pro Gly Met Phe Val Gln Glu Lys Glu Ala Val
1               5                   10                  15

Thr Leu Asp Cys Thr Tyr Asp Thr Ser Asp Gln Ser Tyr Gly Leu Phe
                20                  25                  30

Trp Tyr Lys Gln Pro Ser Ser Gly Glu Met Ile Phe Leu Ile Tyr Gln
            35                  40                  45

Gly Ser Tyr Asp Glu Gln Asn Ala Thr Glu Gly Arg Tyr Ser Leu Asn
        50                  55                  60

Phe Gln Lys Ala Arg Lys Ser Ala Asn Leu Val Ile Ser Ala Ser Gln
65                  70                  75                  80

Leu Gly Asp Ser Ala Met Tyr Phe Cys Ala Met Arg Glu Ile Tyr Ser
                85                  90                  95

Ser Ala Ser Lys Ile Ile Phe Gly Ser Gly Thr Arg Leu Ser Ile Arg
                100                 105                 110

Pro Asn Ile Gln Asn Pro Asp Pro Ala Val Tyr Gln Leu Arg Asp Ser
            115                 120                 125

Lys Ser Ser Asp Lys Ser Val Cys Leu Phe Thr Asp Phe Asp Ser Gln
        130                 135                 140

Thr Asn Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
                180                 185                 190

Ser Ile Ile Pro Glu Asp Thr Phe Phe Pro Ser Pro Glu Ser Ser Cys
            195                 200                 205

Arg Ala Lys Arg Gly Ser Gly Ala Thr Asn Phe Ser Leu Leu Lys Gln
        210                 215                 220

Ala Gly Asp Val Glu Glu Asn Pro Gly
225                 230

<210> SEQ ID NO 34
<211> LENGTH: 236
<212> TYPE: PRT
<213> ORGANISM: Artificial Sequence
<220> FEATURE:
<223> OTHER INFORMATION: Mature soluble hTERT-TCR-1 alpha-chain with
```

-continued full-length variable region, cysteine-substituted constant region
and residual 2A amino acids at C-terminus.

<400> SEQUENCE: 34

Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Gln Ser Tyr
                20                  25                  30

Gly Leu Phe Trp Tyr Lys Gln Pro Ser Ser Gly Glu Met Ile Phe Leu
            35                  40                  45

Ile Tyr Gln Gly Ser Tyr Asp Glu Gln Asn Ala Thr Glu Gly Arg Tyr
        50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Glu
                85                  90                  95

Ile Tyr Ser Ser Ala Ser Lys Ile Ile Phe Gly Ser Gly Thr Arg Leu
            100                 105                 110

Ser Ile Arg Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Cys Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Arg Ala Lys Arg Gly Ser Gly Ala Thr Asn Phe Ser Leu
210                 215                 220

Leu Lys Gln Ala Gly Asp Val Glu Glu Asn Pro Gly
225                 230                 235

<210> SEQ ID NO 35
<211> LENGTH: 270
<212> TYPE: PRT
<213> ORGANISM: Artificial Sequence
<220> FEATURE:
<223> OTHER INFORMATION: Mature soluble hTERT-TCR-1 beta-chain with
      truncated variable region, cysteine-substituted constant region
      and residual 2A amino acids at C-terminus.

<400> SEQUENCE: 35

Val Ser Gln Ser Pro Ser Asn Lys Val Thr Glu Lys Gly Lys Asp Val
1               5                   10                  15

Glu Leu Arg Cys Asp Pro Ile Ser Gly His Thr Ala Leu Tyr Trp Tyr
                20                  25                  30

Arg Gln Ser Leu Gly Gln Gly Leu Glu Phe Leu Ile Tyr Phe Gln Gly
            35                  40                  45

Asn Ser Ala Pro Asp Lys Ser Gly Leu Pro Ser Asp Arg Phe Ser Ala
        50                  55                  60

Glu Arg Thr Gly Gly Ser Val Ser Thr Leu Thr Ile Gln Arg Thr Gln
65                  70                  75                  80

Gln Glu Asp Ser Ala Val Tyr Leu Cys Ala Ser Ser Leu Gly Gly Gly
                85                  90                  95

Asp His Thr Asp Thr Gln Tyr Phe Gly Pro Gly Thr Arg Leu Thr Val
                100                 105                 110

Leu Glu Asp Leu Lys Asn Val Phe Pro Pro Glu Val Ala Val Phe Glu
            115                 120                 125

Pro Ser Glu Ala Glu Ile Ser His Thr Gln Lys Ala Thr Leu Val Cys
        130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
        210                 215                 220

Asp Arg Ala Lys Pro Val Thr Gln Ile Val Ser Ala Glu Ala Trp Gly
225                 230                 235                 240

Arg Ala Asp Cys Gly Arg Ala Lys Arg Gly Ser Gly Ala Thr Asn Phe
                245                 250                 255

Ser Leu Leu Lys Gln Ala Gly Asp Val Glu Glu Asn Pro Gly
            260                 265                 270

<210> SEQ ID NO 36
<211> LENGTH: 273
<212> TYPE: PRT
<213> ORGANISM: Artificial Sequence
<220> FEATURE:
<223> OTHER INFORMATION: Mature soluble hTERT-TCR-1 beta-chain with
      full-length variable region, cysteine-substituted constant region
      and residual 2A amino acids at C-terminus.

<400> SEQUENCE: 36

Gly Ala Gly Val Ser Gln Ser Pro Ser Asn Lys Val Thr Glu Lys Gly
1               5                   10                  15

Lys Asp Val Glu Leu Arg Cys Asp Pro Ile Ser Gly His Thr Ala Leu
            20                  25                  30

Tyr Trp Tyr Arg Gln Ser Leu Gly Gln Gly Leu Glu Phe Leu Ile Tyr
        35                  40                  45

Phe Gln Gly Asn Ser Ala Pro Asp Lys Ser Gly Leu Pro Ser Asp Arg
    50                  55                  60

Phe Ser Ala Glu Arg Thr Gly Gly Ser Val Ser Thr Leu Thr Ile Gln
65                  70                  75                  80

Arg Thr Gln Gln Glu Asp Ser Ala Val Tyr Leu Cys Ala Ser Ser Leu
                85                  90                  95

Gly Gly Gly Asp His Thr Asp Thr Gln Tyr Phe Gly Pro Gly Thr Arg
            100                 105                 110

Leu Thr Val Leu Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Cys Thr Asp Pro
                165                 170                 175

```
Gln Pro Leu Lys Glu Gln Pro Ala Leu Asn Asp Ser Arg Tyr Cys Leu
            180                 185                 190

Ser Ser Arg Leu Arg Val Ser Ala Thr Phe Trp Gln Asn Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp Cys Gly Arg Ala Lys Arg Gly Ser Gly Ala
                245                 250                 255

Thr Asn Phe Ser Leu Leu Lys Gln Ala Gly Asp Val Glu Glu Asn Pro
            260                 265                 270

Gly
```

```
<210> SEQ ID NO 37
<211> LENGTH: 254
<212> TYPE: PRT
<213> ORGANISM: Homo sapiens

<400> SEQUENCE: 37

Ile Thr Gln Thr Gln Pro Gly Met Phe Val Gln Glu Lys Glu Ala Val
1               5                   10                  15

Thr Leu Asp Cys Thr Tyr Asp Thr Ser Asp Gln Ser Tyr Gly Leu Phe
            20                  25                  30

Trp Tyr Lys Gln Pro Ser Ser Gly Glu Met Ile Phe Leu Ile Tyr Gln
        35                  40                  45

Gly Ser Tyr Asp Glu Gln Asn Ala Thr Glu Gly Arg Tyr Ser Leu Asn
    50                  55                  60

Phe Gln Lys Ala Arg Lys Ser Ala Asn Leu Val Ile Ser Ala Ser Gln
65                  70                  75                  80

Leu Gly Asp Ser Ala Met Tyr Phe Cys Ala Met Arg Glu Ile Tyr Ser
                85                  90                  95

Ser Ala Ser Lys Ile Ile Phe Gly Ser Gly Thr Arg Leu Ser Ile Arg
            100                 105                 110

Pro Asn Ile Gln Asn Pro Asp Pro Ala Val Tyr Gln Leu Arg Asp Ser
        115                 120                 125

Lys Ser Ser Asp Lys Ser Val Cys Leu Phe Thr Asp Phe Asp Ser Gln
    130                 135                 140

Thr Asn Val Ser Gln Ser Lys Asp Ser Asp Val Tyr Ile Thr Asp Lys
145                 150                 155                 160

Thr Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser Cys
        195                 200                 205

Asp Val Lys Leu Val Glu Lys Ser Phe Glu Thr Asp Thr Asn Leu Asn
    210                 215                 220

Phe Gln Asn Leu Ser Val Ile Gly Phe Arg Ile Leu Leu Leu Lys Val
225                 230                 235                 240

Ala Gly Phe Asn Leu Leu Met Thr Leu Arg Leu Trp Ser Ser
                245                 250
```

```
<210> SEQ ID NO 38
<211> LENGTH: 257
```

<212> TYPE: PRT
<213> ORGANISM: Homo sapiens

<400> SEQUENCE: 38

```
Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Gln Ser Tyr
            20                  25                  30

Gly Leu Phe Trp Tyr Lys Gln Pro Ser Ser Gly Glu Met Ile Phe Leu
        35                  40                  45

Ile Tyr Gln Gly Ser Tyr Asp Glu Gln Asn Ala Thr Glu Gly Arg Tyr
    50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Glu
                85                  90                  95

Ile Tyr Ser Ser Ala Ser Lys Ile Ile Phe Gly Ser Gly Thr Arg Leu
            100                 105                 110

Ser Ile Arg Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Asp Val Lys Leu Val Glu Lys Ser Phe Glu Thr Asp Thr
    210                 215                 220

Asn Leu Asn Phe Gln Asn Leu Ser Val Ile Gly Phe Arg Ile Leu Leu
225                 230                 235                 240

Leu Lys Val Ala Gly Phe Asn Leu Leu Met Thr Leu Arg Leu Trp Ser
                245                 250                 255

Ser
```

<210> SEQ ID NO 39
<211> LENGTH: 292
<212> TYPE: PRT
<213> ORGANISM: Homo sapiens

<400> SEQUENCE: 39

```
Val Ser Gln Ser Pro Ser Asn Lys Val Thr Glu Lys Gly Lys Asp Val
1               5                   10                  15

Glu Leu Arg Cys Asp Pro Ile Ser Gly His Thr Ala Leu Tyr Trp Tyr
            20                  25                  30

Arg Gln Ser Leu Gly Gln Gly Leu Glu Phe Leu Ile Tyr Phe Gln Gly
        35                  40                  45

Asn Ser Ala Pro Asp Lys Ser Gly Leu Pro Ser Asp Arg Phe Ser Ala
    50                  55                  60

Glu Arg Thr Gly Gly Ser Val Ser Thr Leu Thr Ile Gln Arg Thr Gln
65                  70                  75                  80

Gln Glu Asp Ser Ala Val Tyr Leu Cys Ala Ser Ser Leu Gly Gly Gly
```

```
                    85                  90                  95
Asp His Thr Asp Thr Gln Tyr Phe Gly Pro Gly Thr Arg Leu Thr Val
                100                 105                 110

Leu Glu Asp Leu Lys Asn Val Phe Pro Pro Glu Val Ala Val Phe Glu
            115                 120                 125

Pro Ser Glu Ala Glu Ile Ser His Thr Gln Lys Ala Thr Leu Val Cys
        130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Cys Gly Phe Thr Ser Glu Ser Tyr Gln Gln Gly Val Leu
                245                 250                 255

Ser Ala Thr Ile Leu Tyr Glu Ile Leu Leu Gly Lys Ala Thr Leu Tyr
            260                 265                 270

Ala Val Leu Val Ser Ala Leu Val Leu Met Ala Met Val Lys Arg Lys
        275                 280                 285

Asp Ser Arg Gly
    290

<210> SEQ ID NO 40
<211> LENGTH: 295
<212> TYPE: PRT
<213> ORGANISM: Homo sapiens

<400> SEQUENCE: 40

Gly Ala Gly Val Ser Gln Ser Pro Ser Asn Lys Val Thr Glu Lys Gly
1               5                   10                  15

Lys Asp Val Glu Leu Arg Cys Asp Pro Ile Ser Gly His Thr Ala Leu
            20                  25                  30

Tyr Trp Tyr Arg Gln Ser Leu Gly Gln Gly Leu Glu Phe Leu Ile Tyr
        35                  40                  45

Phe Gln Gly Asn Ser Ala Pro Asp Lys Ser Gly Leu Pro Ser Asp Arg
    50                  55                  60

Phe Ser Ala Glu Arg Thr Gly Gly Ser Val Ser Thr Leu Thr Ile Gln
65                  70                  75                  80

Arg Thr Gln Gln Glu Asp Ser Ala Val Tyr Leu Cys Ala Ser Ser Leu
                85                  90                  95

Gly Gly Gly Asp His Thr Asp Thr Gln Tyr Phe Gly Pro Gly Thr Arg
            100                 105                 110

Leu Thr Val Leu Glu Asp Leu Lys Asn Val Phe Pro Pro Glu Val Ala
        115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160
```

```
Trp Trp Val Asn Gly Lys Glu Val His Ser Gly Val Ser Thr Asp Pro
                165                 170                 175

Gln Pro Leu Lys Glu Gln Pro Ala Leu Asn Asp Ser Arg Tyr Cys Leu
            180                 185                 190

Ser Ser Arg Leu Arg Val Ser Ala Thr Phe Trp Gln Asn Pro Arg Asn
            195                 200                 205

His Phe Arg Cys Gln Val Gln Phe Tyr Gly Leu Ser Glu Asn Asp Glu
210                 215                 220

Trp Thr Gln Asp Arg Ala Lys Pro Val Thr Gln Ile Val Ser Ala Glu
225                 230                 235                 240

Ala Trp Gly Arg Ala Asp Cys Gly Phe Thr Ser Glu Ser Tyr Gln Gln
            245                 250                 255

Gly Val Leu Ser Ala Thr Ile Leu Tyr Glu Ile Leu Leu Gly Lys Ala
            260                 265                 270

Thr Leu Tyr Ala Val Leu Val Ser Ala Leu Val Leu Met Ala Met Val
            275                 280                 285

Lys Arg Lys Asp Ser Arg Gly
            290                 295

<210> SEQ ID NO 41
<211> LENGTH: 208
<212> TYPE: PRT
<213> ORGANISM: Artificial Sequence
<220> FEATURE:
<223> OTHER INFORMATION: Mature soluble hTERT-TCR-1 alpha-chain with
      truncated variable region and cysteine-substituted constant
      region.

<400> SEQUENCE: 41

Ile Thr Gln Thr Gln Pro Gly Met Phe Val Gln Glu Lys Glu Ala Val
1               5                   10                  15

Thr Leu Asp Cys Thr Tyr Asp Thr Ser Asp Gln Ser Tyr Gly Leu Phe
            20                  25                  30

Trp Tyr Lys Gln Pro Ser Ser Gly Glu Met Ile Phe Leu Ile Tyr Gln
            35                  40                  45

Gly Ser Tyr Asp Glu Gln Asn Ala Thr Glu Gly Arg Tyr Ser Leu Asn
50                  55                  60

Phe Gln Lys Ala Arg Lys Ser Ala Asn Leu Val Ile Ser Ala Ser Gln
65                  70                  75                  80

Leu Gly Asp Ser Ala Met Tyr Phe Cys Ala Met Arg Glu Ile Tyr Ser
                85                  90                  95

Ser Ala Ser Lys Ile Ile Phe Gly Ser Gly Thr Arg Leu Ser Ile Arg
            100                 105                 110

Pro Asn Ile Gln Asn Pro Asp Pro Ala Val Tyr Gln Leu Arg Asp Ser
            115                 120                 125

Lys Ser Ser Asp Lys Ser Val Cys Leu Phe Thr Asp Phe Asp Ser Gln
            130                 135                 140

Thr Asn Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser Cys
            195                 200                 205
```

```
<210> SEQ ID NO 42
<211> LENGTH: 211
<212> TYPE: PRT
<213> ORGANISM: Artificial Sequence
<220> FEATURE:
<223> OTHER INFORMATION: Mature soluble hTERT-TCR-1 alpha-chain with
      full-length variable region and cysteine-substituted constant
      region.

<400> SEQUENCE: 42
```

Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Gln Ser Tyr
            20                  25                  30

Gly Leu Phe Trp Tyr Lys Gln Pro Ser Ser Gly Glu Met Ile Phe Leu
        35                  40                  45

Ile Tyr Gln Gly Ser Tyr Asp Glu Gln Asn Ala Thr Glu Gly Arg Tyr
50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Glu
            85                  90                  95

Ile Tyr Ser Ser Ala Ser Lys Ile Ile Phe Gly Ser Gly Thr Arg Leu
        100                 105                 110

Ser Ile Arg Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Cys Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys
    210

```
<210> SEQ ID NO 43
<211> LENGTH: 245
<212> TYPE: PRT
<213> ORGANISM: Artificial Sequence
<220> FEATURE:
<223> OTHER INFORMATION: Mature soluble hTERT-TCR-1 beta-chain with
      truncated variable region and cysteine-substituted constant
      region.

<400> SEQUENCE: 43
```

Val Ser Gln Ser Pro Ser Asn Lys Val Thr Glu Lys Gly Lys Asp Val
1               5                   10                  15

Glu Leu Arg Cys Asp Pro Ile Ser Gly His Thr Ala Leu Tyr Trp Tyr
            20                  25                  30

Arg Gln Ser Leu Gly Gln Gly Leu Glu Phe Leu Ile Tyr Phe Gln Gly
        35                  40                  45

Asn Ser Ala Pro Asp Lys Ser Gly Leu Pro Ser Asp Arg Phe Ser Ala
50                  55                  60

Glu Arg Thr Gly Gly Ser Val Ser Thr Leu Thr Ile Gln Arg Thr Gln
65                  70                  75                  80

```
Gln Glu Asp Ser Ala Val Tyr Leu Cys Ala Ser Ser Leu Gly Gly Gly
                85                  90                  95

Asp His Thr Asp Thr Gln Tyr Phe Gly Pro Gly Thr Arg Leu Thr Val
            100                 105                 110

Leu Glu Asp Leu Lys Asn Val Phe Pro Pro Glu Val Ala Val Phe Glu
            115                 120                 125

Pro Ser Glu Ala Glu Ile Ser His Thr Gln Lys Ala Thr Leu Val Cys
130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
            195                 200                 205

Cys Gln Val Gln Phe Tyr Gly Leu Ser Glu Asn Asp Glu Trp Thr Gln
            210                 215                 220

Asp Arg Ala Lys Pro Val Thr Gln Ile Val Ser Ala Glu Ala Trp Gly
225                 230                 235                 240

Arg Ala Asp Cys Gly
                245

<210> SEQ ID NO 44
<211> LENGTH: 248
<212> TYPE: PRT
<213> ORGANISM: Artificial Sequence
<220> FEATURE:
<223> OTHER INFORMATION: Mature soluble hTERT-TCR-1 beta-chain with
      full-length variable region and cysteine-substituted constant
      region.

<400> SEQUENCE: 44

Gly Ala Gly Val Ser Gln Ser Pro Ser Asn Lys Val Thr Glu Lys Gly
1               5                   10                  15

Lys Asp Val Glu Leu Arg Cys Asp Pro Ile Ser Gly His Thr Ala Leu
            20                  25                  30

Tyr Trp Tyr Arg Gln Ser Leu Gly Gln Gly Leu Glu Phe Leu Ile Tyr
            35                  40                  45

Phe Gln Gly Asn Ser Ala Pro Asp Lys Ser Gly Leu Pro Ser Asp Arg
    50                  55                  60

Phe Ser Ala Glu Arg Thr Gly Gly Ser Val Ser Thr Leu Thr Ile Gln
65                  70                  75                  80

Arg Thr Gln Gln Glu Asp Ser Ala Val Tyr Leu Cys Ala Ser Ser Leu
                85                  90                  95

Gly Gly Gly Asp His Thr Asp Thr Gln Tyr Phe Gly Pro Gly Thr Arg
            100                 105                 110

Leu Thr Val Leu Glu Asp Leu Lys Asn Val Phe Pro Pro Glu Val Ala
            115                 120                 125

Val Phe Glu Pro Ser Glu Ala Glu Ile Ser His Thr Gln Lys Ala Thr
130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Cys Thr Asp Pro
                165                 170                 175
```

Gln Pro Leu Lys Glu Gln Pro Ala Leu Asn Asp Ser Arg Tyr Cys Leu
            180                 185                 190

Ser Ser Arg Leu Arg Val Ser Ala Thr Phe Trp Gln Asn Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp Cys Gly
            245

<210> SEQ ID NO 45
<211> LENGTH: 27
<212> TYPE: PRT
<213> ORGANISM: Homo sapiens

<400> SEQUENCE: 45

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 46
<211> LENGTH: 112
<212> TYPE: PRT
<213> ORGANISM: Homo sapiens

<400> SEQUENCE: 46

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
            100                 105                 110

<210> SEQ ID NO 47
<211> LENGTH: 391
<212> TYPE: PRT
<213> ORGANISM: Artificial Sequence
<220> FEATURE:
<223> OTHER INFORMATION: Mature soluble hTERT-TCR-1 alpha-chain with
      full-length variable region, cysteine-substituted constant region
      and CD28-CD3zeta tail.

<400> SEQUENCE: 47

Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Gln Ser Tyr
            20                  25                  30

Gly Leu Phe Trp Tyr Lys Gln Pro Ser Ser Gly Glu Met Ile Phe Leu
        35                  40                  45

Ile Tyr Gln Gly Ser Tyr Asp Glu Gln Asn Ala Thr Glu Gly Arg Tyr
    50                  55                  60

Ser Leu Asn Phe Gln Lys Ala Arg Lys Ser Ala Asn Leu Val Ile Ser
 65                  70                  75                  80

Ala Ser Gln Leu Gly Asp Ser Ala Met Tyr Phe Cys Ala Met Arg Glu
                 85                  90                  95

Ile Tyr Ser Ser Ala Ser Lys Ile Ile Phe Gly Ser Gly Thr Arg Leu
            100                 105                 110

Ser Ile Arg Pro Asn Ile Gln Asn Pro Asp Pro Ala Val Tyr Gln Leu
        115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Cys Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys Phe Trp Val Leu Val Val Val Gly Gly Val Leu Ala Cys
210                 215                 220

Tyr Ser Leu Leu Val Thr Val Ala Phe Ile Ile Phe Trp Val Arg Ser
225                 230                 235                 240

Lys Arg Ser Arg Leu Leu His Ser Asp Tyr Met Asn Met Thr Pro Arg
                245                 250                 255

Arg Pro Gly Pro Thr Arg Lys His Tyr Gln Pro Tyr Ala Pro Pro Arg
            260                 265                 270

Asp Phe Ala Ala Tyr Arg Ser Arg Val Lys Phe Ser Arg Ser Ala Asp
        275                 280                 285

Ala Pro Ala Tyr Gln Gln Gly Gln Asn Gln Leu Tyr Asn Glu Leu Asn
290                 295                 300

Leu Gly Arg Arg Glu Glu Tyr Asp Val Leu Asp Lys Arg Arg Gly Arg
305                 310                 315                 320

Asp Pro Glu Met Gly Gly Lys Pro Arg Arg Lys Asn Pro Gln Glu Gly
                325                 330                 335

Leu Tyr Asn Glu Leu Gln Lys Asp Lys Met Ala Glu Ala Tyr Ser Glu
            340                 345                 350

Ile Gly Met Lys Gly Glu Arg Arg Arg Gly Lys Gly His Asp Gly Leu
        355                 360                 365

Tyr Gln Gly Leu Ser Thr Ala Thr Lys Asp Thr Tyr Asp Ala Leu His
370                 375                 380

Met Gln Ala Leu Pro Pro Arg
385                 390

<210> SEQ ID NO 48
<211> LENGTH: 428
<212> TYPE: PRT
<213> ORGANISM: Artificial Sequence
<220> FEATURE:
<223> OTHER INFORMATION: Mature soluble hTERT-TCR-1 beta-chain with
      full-length variable region, cysteine-substituted constant region
      and CD28-CD3zeta tail.

<400> SEQUENCE: 48

Gly Ala Gly Val Ser Gln Ser Pro Ser Asn Lys Val Thr Glu Lys Gly

-continued

```
1               5                   10                  15
Lys Asp Val Glu Leu Arg Cys Asp Pro Ile Ser Gly His Thr Ala Leu
            20                  25                  30

Tyr Trp Tyr Arg Gln Ser Leu Gly Gln Gly Leu Glu Phe Leu Ile Tyr
            35                  40                  45

Phe Gln Gly Asn Ser Ala Pro Asp Lys Ser Gly Leu Pro Ser Asp Arg
50                      55                  60

Phe Ser Ala Glu Arg Thr Gly Gly Ser Val Ser Thr Leu Thr Ile Gln
65                  70                  75                  80

Arg Thr Gln Gln Glu Asp Ser Ala Val Tyr Leu Cys Ala Ser Ser Leu
                85                  90                  95

Gly Gly Gly Asp His Thr Asp Thr Gln Tyr Phe Gly Pro Gly Thr Arg
                100                 105                 110

Leu Thr Val Leu Glu Asp Leu Lys Asn Val Phe Pro Pro Glu Val Ala
            115                 120                 125

Val Phe Glu Pro Ser Glu Ala Glu Ile Ser His Thr Gln Lys Ala Thr
        130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Cys Thr Asp Pro
                165                 170                 175

Gln Pro Leu Lys Glu Gln Pro Ala Leu Asn Asp Ser Arg Tyr Cys Leu
            180                 185                 190

Ser Ser Arg Leu Arg Val Ser Ala Thr Phe Trp Gln Asn Pro Arg Asn
        195                 200                 205

His Phe Arg Cys Gln Val Gln Phe Tyr Gly Leu Ser Glu Asn Asp Glu
    210                 215                 220

Trp Thr Gln Asp Arg Ala Lys Pro Val Thr Gln Ile Val Ser Ala Glu
225                 230                 235                 240

Ala Trp Gly Arg Ala Asp Cys Gly Phe Trp Val Leu Val Val Val Gly
                245                 250                 255

Gly Val Leu Ala Cys Tyr Ser Leu Leu Val Thr Val Ala Phe Ile Ile
            260                 265                 270

Phe Trp Val Arg Ser Lys Arg Ser Arg Leu Leu His Ser Asp Tyr Met
        275                 280                 285

Asn Met Thr Pro Arg Arg Pro Gly Pro Thr Arg Lys His Tyr Gln Pro
    290                 295                 300

Tyr Ala Pro Pro Arg Asp Phe Ala Ala Tyr Arg Ser Arg Val Lys Phe
305                 310                 315                 320

Ser Arg Ser Ala Asp Ala Pro Ala Tyr Gln Gln Gly Gln Asn Gln Leu
                325                 330                 335

Tyr Asn Glu Leu Asn Leu Gly Arg Arg Glu Glu Tyr Asp Val Leu Asp
            340                 345                 350

Lys Arg Arg Gly Arg Asp Pro Glu Met Gly Gly Lys Pro Arg Arg Lys
        355                 360                 365

Asn Pro Gln Glu Gly Leu Tyr Asn Glu Leu Gln Lys Asp Lys Met Ala
    370                 375                 380

Glu Ala Tyr Ser Glu Ile Gly Met Lys Gly Glu Arg Arg Arg Gly Lys
385                 390                 395                 400

Gly His Asp Gly Leu Tyr Gln Gly Leu Ser Thr Ala Thr Lys Asp Thr
                405                 410                 415

Tyr Asp Ala Leu His Met Gln Ala Leu Pro Pro Arg
            420                 425
```

<210> SEQ ID NO 49
<211> LENGTH: 704
<212> TYPE: PRT
<213> ORGANISM: Artificial Sequence
<220> FEATURE:
<223> OTHER INFORMATION: hTERT-TCR-1 scTCR-CAR with CD28-CD3zeta tail on alpha-chain

<400> SEQUENCE: 49

```
Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Ile Tyr Ser Ser Ala Ser Lys Ile Ile Phe Gly Ser
        115                 120                 125

Gly Thr Arg Leu Ser Ile Arg Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Cys Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Phe Trp Val Leu Val Val Val Gly Gly
225                 230                 235                 240

Val Leu Ala Cys Tyr Ser Leu Leu Val Thr Val Ala Phe Ile Ile Phe
                245                 250                 255

Trp Val Arg Ser Lys Arg Ser Arg Leu Leu His Ser Asp Tyr Met Asn
            260                 265                 270

Met Thr Pro Arg Arg Pro Gly Pro Thr Arg Lys His Tyr Gln Pro Tyr
        275                 280                 285

Ala Pro Pro Arg Asp Phe Ala Ala Tyr Arg Ser Arg Val Lys Phe Ser
    290                 295                 300

Arg Ser Ala Asp Ala Pro Ala Tyr Gln Gln Gly Gln Asn Gln Leu Tyr
305                 310                 315                 320

Asn Glu Leu Asn Leu Gly Arg Arg Glu Glu Tyr Asp Val Leu Asp Lys
                325                 330                 335

Arg Arg Gly Arg Asp Pro Glu Met Gly Gly Lys Pro Arg Arg Lys Asn
            340                 345                 350

Pro Gln Glu Gly Leu Tyr Asn Glu Leu Gln Lys Asp Lys Met Ala Glu
```

```
                    355                 360                 365
Ala Tyr Ser Glu Ile Gly Met Lys Gly Glu Arg Arg Gly Lys Gly
            370                 375                 380

His Asp Gly Leu Tyr Gln Gly Leu Ser Thr Ala Thr Lys Asp Thr Tyr
385                 390                 395                 400

Asp Ala Leu His Met Gln Ala Leu Pro Pro Arg Arg Ala Lys Arg Gly
                405                 410                 415

Ser Gly Ala Thr Asn Phe Ser Leu Leu Lys Gln Ala Gly Asp Val Glu
            420                 425                 430

Glu Asn Pro Gly Pro Met Gly Thr Arg Leu Leu Phe Trp Val Ala Phe
        435                 440                 445

Cys Leu Leu Gly Ala Asp His Thr Gly Ala Gly Val Ser Gln Ser Pro
        450                 455                 460

Ser Asn Lys Val Thr Glu Lys Gly Lys Asp Val Glu Leu Arg Cys Asp
465                 470                 475                 480

Pro Ile Ser Gly His Thr Ala Leu Tyr Trp Tyr Arg Gln Ser Leu Gly
                485                 490                 495

Gln Gly Leu Glu Phe Leu Ile Tyr Phe Gln Gly Asn Ser Ala Pro Asp
            500                 505                 510

Lys Ser Gly Leu Pro Ser Asp Arg Phe Ser Ala Glu Arg Thr Gly Gly
        515                 520                 525

Ser Val Ser Thr Leu Thr Ile Gln Arg Thr Gln Gln Glu Asp Ser Ala
530                 535                 540

Val Tyr Leu Cys Ala Ser Ser Leu Gly Gly Gly Asp His Thr Asp Thr
545                 550                 555                 560

Gln Tyr Phe Gly Pro Gly Thr Arg Leu Thr Val Leu Glu Asp Leu Lys
                565                 570                 575

Asn Val Phe Pro Pro Glu Val Ala Val Phe Glu Pro Ser Glu Ala Glu
            580                 585                 590

Ile Ser His Thr Gln Lys Ala Thr Leu Val Cys Leu Ala Thr Gly Phe
        595                 600                 605

Tyr Pro Asp His Val Glu Leu Ser Trp Trp Val Asn Gly Lys Glu Val
        610                 615                 620

His Ser Gly Val Cys Thr Asp Pro Gln Pro Leu Lys Glu Gln Pro Ala
625                 630                 635                 640

Leu Asn Asp Ser Arg Tyr Cys Leu Ser Ser Arg Leu Arg Val Ser Ala
                645                 650                 655

Thr Phe Trp Gln Asn Pro Arg Asn His Phe Arg Cys Gln Val Gln Phe
            660                 665                 670

Tyr Gly Leu Ser Glu Asn Asp Glu Trp Thr Gln Asp Arg Ala Lys Pro
        675                 680                 685

Val Thr Gln Ile Val Ser Ala Glu Ala Trp Gly Arg Ala Asp Cys Gly
        690                 695                 700

<210> SEQ ID NO 50
<211> LENGTH: 704
<212> TYPE: PRT
<213> ORGANISM: Artificial Sequence
<220> FEATURE:
<223> OTHER INFORMATION: hTERT-TCR-1 scTCR-CAR with CD28-CD3zeta tail on
      beta-chain.

<400> SEQUENCE: 50

Met Ser Leu Ser Ser Leu Leu Lys Val Val Thr Ala Ser Leu Trp Leu
1               5                   10                  15
```

```
Gly Pro Gly Ile Ala Gln Lys Ile Thr Gln Thr Gln Pro Gly Met Phe
                20                  25                  30

Val Gln Glu Lys Glu Ala Val Thr Leu Asp Cys Thr Tyr Asp Thr Ser
            35                  40                  45

Asp Gln Ser Tyr Gly Leu Phe Trp Tyr Lys Gln Pro Ser Ser Gly Glu
        50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Ile Tyr Ser Ser Ala Ser Lys Ile Ile Phe Gly Ser
        115                 120                 125

Gly Thr Arg Leu Ser Ile Arg Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Cys Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220

Pro Ser Pro Glu Ser Ser Cys Arg Ala Lys Arg Gly Ser Gly Ala Thr
225                 230                 235                 240

Asn Phe Ser Leu Leu Lys Gln Ala Gly Asp Val Glu Asn Pro Gly Pro
                245                 250                 255

Pro Met Gly Thr Arg Leu Leu Phe Trp Val Ala Phe Cys Leu Leu Gly
            260                 265                 270

Ala Asp His Thr Gly Ala Gly Val Ser Gln Ser Pro Ser Asn Lys Val
        275                 280                 285

Thr Glu Lys Gly Lys Asp Val Glu Leu Arg Cys Asp Pro Ile Ser Gly
    290                 295                 300

His Thr Ala Leu Tyr Trp Tyr Arg Gln Ser Leu Gly Gln Gly Leu Glu
305                 310                 315                 320

Phe Leu Ile Tyr Phe Gln Gly Asn Ser Ala Pro Asp Lys Ser Gly Leu
                325                 330                 335

Pro Ser Asp Arg Phe Ser Ala Glu Arg Thr Gly Gly Ser Val Ser Thr
            340                 345                 350

Leu Thr Ile Gln Arg Thr Gln Gln Glu Asp Ser Ala Val Tyr Leu Cys
        355                 360                 365

Ala Ser Ser Leu Gly Gly Gly Asp His Thr Asp Thr Gln Tyr Phe Gly
    370                 375                 380

Pro Gly Thr Arg Leu Thr Val Leu Glu Asp Leu Lys Asn Val Phe Pro
385                 390                 395                 400

Pro Glu Val Ala Val Phe Glu Pro Ser Glu Ala Glu Ile Ser His Thr
                405                 410                 415

Gln Lys Ala Thr Leu Val Cys Leu Ala Thr Gly Phe Tyr Pro Asp His
            420                 425                 430

Val Glu Leu Ser Trp Trp Val Asn Gly Lys Glu Val His Ser Gly Val
```

435                 440                 445

Cys Thr Asp Pro Gln Pro Leu Lys Glu Gln Pro Ala Leu Asn Asp Ser
    450                 455                 460

Arg Tyr Cys Leu Ser Ser Arg Leu Arg Val Ser Ala Thr Phe Trp Gln
465                 470                 475                 480

Asn Pro Arg Asn His Phe Arg Cys Gln Val Gln Phe Tyr Gly Leu Ser
                485                 490                 495

Glu Asn Asp Glu Trp Thr Gln Asp Arg Ala Lys Pro Val Thr Gln Ile
            500                 505                 510

Val Ser Ala Glu Ala Trp Gly Arg Ala Asp Cys Gly Phe Trp Val Leu
        515                 520                 525

Val Val Val Gly Gly Val Leu Ala Cys Tyr Ser Leu Leu Val Thr Val
    530                 535                 540

Ala Phe Ile Ile Phe Trp Val Arg Ser Lys Arg Ser Arg Leu Leu His
545                 550                 555                 560

Ser Asp Tyr Met Asn Met Thr Pro Arg Arg Pro Gly Pro Thr Arg Lys
                565                 570                 575

His Tyr Gln Pro Tyr Ala Pro Pro Arg Asp Phe Ala Ala Tyr Arg Ser
            580                 585                 590

Arg Val Lys Phe Ser Arg Ser Ala Asp Ala Pro Ala Tyr Gln Gln Gly
        595                 600                 605

Gln Asn Gln Leu Tyr Asn Glu Leu Asn Leu Gly Arg Arg Glu Glu Tyr
    610                 615                 620

Asp Val Leu Asp Lys Arg Arg Gly Arg Asp Pro Glu Met Gly Gly Lys
625                 630                 635                 640

Pro Arg Arg Lys Asn Pro Gln Glu Gly Leu Tyr Asn Glu Leu Gln Lys
                645                 650                 655

Asp Lys Met Ala Glu Ala Tyr Ser Glu Ile Gly Met Lys Gly Glu Arg
            660                 665                 670

Arg Arg Gly Lys Gly His Asp Gly Leu Tyr Gln Gly Leu Ser Thr Ala
        675                 680                 685

Thr Lys Asp Thr Tyr Asp Ala Leu His Met Gln Ala Leu Pro Pro Arg
    690                 695                 700

<210> SEQ ID NO 51
<211> LENGTH: 1132
<212> TYPE: PRT
<213> ORGANISM: Homo sapiens

<400> SEQUENCE: 51

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
            85                  90                  95

Leu Ala Phe Gly Phe Ala Leu Leu Asp Gly Ala Arg Gly Gly Pro Pro
            100                 105                 110

-continued

```
Glu Ala Phe Thr Thr Ser Val Arg Ser Tyr Leu Pro Asn Thr Val Thr
            115                 120                 125
Asp Ala Leu Arg Gly Ser Gly Ala Trp Gly Leu Leu Arg Arg Val
    130                 135                 140
Gly Asp Val Leu Val His Leu Leu Ala Arg Cys Ala Leu Phe Val
145                 150                 155                 160
Leu Val Ala Pro Ser Cys Ala Tyr Gln Val Cys Gly Pro Pro Leu Tyr
                165                 170                 175
Gln Leu Gly Ala Ala Thr Gln Ala Arg Pro Pro His Ala Ser Gly
            180                 185                 190
Pro Arg Arg Arg Leu Gly Cys Glu Arg Ala Trp Asn His Ser Val Arg
    195                 200                 205
Glu Ala Gly Val Pro Leu Gly Leu Pro Ala Pro Gly Ala Arg Arg Arg
    210                 215                 220
Gly Gly Ser Ala Ser Arg Ser Leu Pro Leu Pro Lys Arg Pro Arg Arg
225                 230                 235                 240
Gly Ala Ala Pro Glu Pro Glu Arg Thr Pro Val Gly Gln Gly Ser Trp
                245                 250                 255
Ala His Pro Gly Arg Thr Arg Gly Pro Ser Asp Arg Gly Phe Cys Val
            260                 265                 270
Val Ser Pro Ala Arg Pro Ala Glu Glu Ala Thr Ser Leu Glu Gly Ala
    275                 280                 285
Leu Ser Gly Thr Arg His Ser His Pro Ser Val Gly Arg Gln His His
    290                 295                 300
Ala Gly Pro Pro Ser Thr Ser Arg Pro Arg Pro Trp Asp Thr Pro
305                 310                 315                 320
Cys Pro Pro Val Tyr Ala Glu Thr Lys His Phe Leu Tyr Ser Ser Gly
                325                 330                 335
Asp Lys Glu Gln Leu Arg Pro Ser Phe Leu Leu Ser Ser Leu Arg Pro
            340                 345                 350
Ser Leu Thr Gly Ala Arg Arg Leu Val Glu Thr Ile Phe Leu Gly Ser
    355                 360                 365
Arg Pro Trp Met Pro Gly Thr Pro Arg Arg Leu Pro Arg Leu Pro Gln
    370                 375                 380
Arg Tyr Trp Gln Met Arg Pro Leu Phe Leu Glu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
            420                 425                 430
Gly Ser Val Ala Ala Pro Glu Glu Asp Thr Asp Pro Arg Arg Leu
    435                 440                 445
Val Gln Leu Leu Arg Gln His Ser Ser Pro Trp Gln Val Tyr Gly Phe
    450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
            500                 505                 510
Ser Val Arg Asp Cys Ala Trp Leu Arg Arg Ser Pro Gly Val Gly Cys
    515                 520                 525
Val Pro Ala Ala Glu His Arg Leu Arg Glu Glu Ile Leu Ala Lys Phe
```

```
              530                 535                 540
Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                    565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
        610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                    645                 650                 655

Arg Val Lys Ala Leu Phe Ser Val Leu Asn Tyr Glu Arg Ala Arg Arg
                660                 665                 670

Pro Gly Leu Leu Gly Ala Ser Val Gly Leu Asp Asp Ile His Arg
            675                 680                 685

Ala Trp Arg Thr Phe Val Leu Arg Val Arg Ala Gln Asp Pro Pro
        690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                    725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
        770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                    805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
            835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                    885                 890                 895

Val Val Asn Leu Arg Lys Thr Val Val Asn Phe Pro Val Glu Asp Glu
                900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
        930                 935                 940

Asp Tyr Ser Ser Tyr Ala Arg Thr Ser Ile Arg Ala Ser Leu Thr Phe
945                 950                 955                 960
```

```
Asn Arg Gly Phe Lys Ala Gly Arg Asn Met Arg Arg Lys Leu Phe Gly
            965                 970                 975

Val Leu Arg Leu Lys Cys His Ser Leu Phe Leu Asp Leu Gln Val Asn
        980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 52
<211> LENGTH: 16
<212> TYPE: PRT
<213> ORGANISM: Homo sapiens

<400> SEQUENCE: 52

Glu Ala Arg Pro Ala Leu Leu Thr Ser Arg Leu Arg Phe Ile Pro Lys
1               5                   10                  15

<210> SEQ ID NO 53
<211> LENGTH: 8
<212> TYPE: PRT
<213> ORGANISM: Unknown
<220> FEATURE:
<223> OTHER INFORMATION: Picornaviridae
<220> FEATURE:
<221> NAME/KEY: X
<222> LOCATION: (2)..(2)
<223> OTHER INFORMATION: Valine or Isoleucine
<220> FEATURE:
<221> NAME/KEY: X
<222> LOCATION: (4)..(4)
<223> OTHER INFORMATION: Any amino acid

<400> SEQUENCE: 53

Asp Xaa Glu Xaa Asn Pro Gly Pro
1               5

<210> SEQ ID NO 54
<211> LENGTH: 208
<212> TYPE: PRT
<213> ORGANISM: Artificial Sequence
<220> FEATURE:
<223> OTHER INFORMATION: Mature soluble hTERT-TCR-1 alpha-chain with
      truncated variable region.

<400> SEQUENCE: 54
```

Ile Thr Gln Thr Gln Pro Gly Met Phe Val Gln Glu Lys Glu Ala Val
1               5                   10                  15

Thr Leu Asp Cys Thr Tyr Asp Thr Ser Asp Gln Ser Tyr Gly Leu Phe
            20                  25                  30

Trp Tyr Lys Gln Pro Ser Ser Gly Glu Met Ile Phe Leu Ile Tyr Gln
        35                  40                  45

Gly Ser Tyr Asp Glu Gln Asn Ala Thr Glu Gly Arg Tyr Ser Leu Asn
    50                  55                  60

Phe Gln Lys Ala Arg Lys Ser Ala Asn Leu Val Ile Ser Ala Ser Gln
65                  70                  75                  80

Leu Gly Asp Ser Ala Met Tyr Phe Cys Ala Met Arg Glu Ile Tyr Ser
                85                  90                  95

Ser Ala Ser Lys Ile Ile Phe Gly Ser Gly Thr Arg Leu Ser Ile Arg
                100                 105                 110

Pro Asn Ile Gln Asn Pro Asp Pro Ala Val Tyr Gln Leu Arg Asp Ser
            115                 120                 125

Lys Ser Ser Asp Lys Ser Val Cys Leu Phe Thr Asp Phe Asp Ser Gln
130                 135                 140

Thr Asn Val Ser Gln Ser Lys Asp Ser Asp Val Tyr Ile Thr Asp Lys
145                 150                 155                 160

Thr Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
                180                 185                 190

Ser Ile Ile Pro Glu Asp Thr Phe Phe Pro Ser Pro Glu Ser Ser Cys
                195                 200                 205

<210> SEQ ID NO 55
<211> LENGTH: 211
<212> TYPE: PRT
<213> ORGANISM: Homo sapiens

<400> SEQUENCE: 55

Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Gln Ser Tyr
            20                  25                  30

Gly Leu Phe Trp Tyr Lys Gln Pro Ser Ser Gly Glu Met Ile Phe Leu
        35                  40                  45

Ile Tyr Gln Gly Ser Tyr Asp Glu Gln Asn Ala Thr Glu Gly Arg Tyr
    50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Glu
                85                  90                  95

Ile Tyr Ser Ser Ala Ser Lys Ile Ile Phe Gly Ser Gly Thr Arg Leu
                100                 105                 110

Ser Ile Arg Pro Asn Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
130                 135                 140

Asp Ser Gln Thr Asn Val Ser Gln Ser Lys Asp Ser Asp Val Tyr Ile
145                 150                 155                 160

Thr Asp Lys Thr Val Leu Asp Met Arg Ser Met Asp Phe Lys Ser Asn

```
                165                 170                 175
Ser Ala Val Ala Trp Ser Asn Lys Ser Asp Phe Ala Cys Ala Asn Ala
            180                 185                 190

Phe Asn Asn Ser Ile Ile Pro Glu Asp Thr Phe Phe Pro Ser Pro Glu
        195                 200                 205

Ser Ser Cys
    210

<210> SEQ ID NO 56
<211> LENGTH: 245
<212> TYPE: PRT
<213> ORGANISM: Artificial Sequence
<220> FEATURE:
<223> OTHER INFORMATION: Mature soluble hTERT-TCR-1 beta-chain with
      truncated variable region.

<400> SEQUENCE: 56

Val Ser Gln Ser Pro Ser Asn Lys Val Thr Glu Lys Gly Lys Asp Val
1               5                   10                  15

Glu Leu Arg Cys Asp Pro Ile Ser Gly His Thr Ala Leu Tyr Trp Tyr
            20                  25                  30

Arg Gln Ser Leu Gly Gln Gly Leu Glu Phe Leu Ile Tyr Phe Gln Gly
        35                  40                  45

Asn Ser Ala Pro Asp Lys Ser Gly Leu Pro Ser Asp Arg Phe Ser Ala
    50                  55                  60

Glu Arg Thr Gly Gly Ser Val Ser Thr Leu Thr Ile Gln Arg Thr Gln
65                  70                  75                  80

Gln Glu Asp Ser Ala Val Tyr Leu Cys Ala Ser Ser Leu Gly Gly Gly
                85                  90                  95

Asp His Thr Asp Thr Gln Tyr Phe Gly Pro Gly Thr Arg Leu Thr Val
            100                 105                 110

Leu Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Cys Gly
                245

<210> SEQ ID NO 57
<211> LENGTH: 248
<212> TYPE: PRT
<213> ORGANISM: Homo sapiens

<400> SEQUENCE: 57

Gly Ala Gly Val Ser Gln Ser Pro Ser Asn Lys Val Thr Glu Lys Gly
```

```
                1               5                  10                 15
Lys Asp Val Glu Leu Arg Cys Asp Pro Ile Ser Gly His Thr Ala Leu
                20                 25                 30

Tyr Trp Tyr Arg Gln Ser Leu Gly Gln Gly Leu Glu Phe Leu Ile Tyr
                35                 40                 45

Phe Gln Gly Asn Ser Ala Pro Asp Lys Ser Gly Leu Pro Ser Asp Arg
                50                 55                 60

Phe Ser Ala Glu Arg Thr Gly Gly Ser Val Ser Thr Leu Thr Ile Gln
65                  70                 75                 80

Arg Thr Gln Gln Glu Asp Ser Ala Val Tyr Leu Cys Ala Ser Ser Leu
                    85                 90                 95

Gly Gly Gly Asp His Thr Asp Thr Gln Tyr Phe Gly Pro Gly Thr Arg
                100                105                110

Leu Thr Val Leu Glu Asp Leu Lys Asn Val Phe Pro Pro Glu Val Ala
                115                120                125

Val Phe Glu Pro Ser Glu Ala Glu Ile Ser His Thr Gln Lys Ala Thr
130                 135                140

Leu Val Cys Leu Ala Thr Gly Phe Tyr Pro Asp His Val Glu Leu Ser
145                 150                155                160

Trp Trp Val Asn Gly Lys Glu Val His Ser Gly Val Ser Thr Asp Pro
                165                170                175

Gln Pro Leu Lys Glu Gln Pro Ala Leu Asn Asp Ser Arg Tyr Cys Leu
                180                185                190

Ser Ser Arg Leu Arg Val Ser Ala Thr Phe Trp Gln Asn Pro Arg Asn
                195                200                205

His Phe Arg Cys Gln Val Gln Phe Tyr Gly Leu Ser Glu Asn Asp Glu
                210                215                220

Trp Thr Gln Asp Arg Ala Lys Pro Val Thr Gln Ile Val Ser Ala Glu
225                 230                235                240

Ala Trp Gly Arg Ala Asp Cys Gly
                245

<210> SEQ ID NO 58
<211> LENGTH: 41
<212> TYPE: PRT
<213> ORGANISM: Homo sapiens

<400> SEQUENCE: 58

Arg Ser Lys Arg Ser Arg Leu Leu His Ser Asp Tyr Met Asn Met Thr
1               5                  10                 15

Pro Arg Arg Pro Gly Pro Thr Arg Lys His Tyr Gln Pro Tyr Ala Pro
                20                 25                 30

Pro Arg Asp Phe Ala Ala Tyr Arg Ser
                35                 40

<210> SEQ ID NO 59
<211> LENGTH: 180
<212> TYPE: PRT
<213> ORGANISM: Artificial Sequence
<220> FEATURE:
<223> OTHER INFORMATION: CD28 transmembrane domain - CD28 intracellular
      domain - CD3zeta intracellular domain CAR signalling tail

<400> SEQUENCE: 59

Phe Trp Val Leu Val Val Val Gly Gly Val Leu Ala Cys Tyr Ser Leu
1               5                  10                 15

Leu Val Thr Val Ala Phe Ile Ile Phe Trp Val Arg Ser Lys Arg Ser
```

```
                    20                  25                  30
Arg Leu Leu His Ser Asp Tyr Met Asn Met Thr Pro Arg Arg Pro Gly
            35                  40                  45

Pro Thr Arg Lys His Tyr Gln Pro Tyr Ala Pro Pro Arg Asp Phe Ala
        50                  55                  60

Ala Tyr Arg Ser Arg Val Lys Phe Ser Arg Ser Ala Asp Ala Pro Ala
65                  70                  75                  80

Tyr Gln Gln Gly Gln Asn Gln Leu Tyr Asn Glu Leu Asn Leu Gly Arg
                85                  90                  95

Arg Glu Glu Tyr Asp Val Leu Asp Lys Arg Arg Gly Arg Asp Pro Glu
            100                 105                 110

Met Gly Gly Lys Pro Arg Arg Lys Asn Pro Gln Glu Gly Leu Tyr Asn
        115                 120                 125

Glu Leu Gln Lys Asp Lys Met Ala Glu Ala Tyr Ser Glu Ile Gly Met
    130                 135                 140

Lys Gly Glu Arg Arg Arg Gly Lys Gly His Asp Gly Leu Tyr Gln Gly
145                 150                 155                 160

Leu Ser Thr Ala Thr Lys Asp Thr Tyr Asp Ala Leu His Met Gln Ala
                165                 170                 175

Leu Pro Pro Arg
            180

<210> SEQ ID NO 60
<211> LENGTH: 411
<212> TYPE: PRT
<213> ORGANISM: Artificial Sequence
<220> FEATURE:
<223> OTHER INFORMATION: Mature soluble hTERT-TCR-1 alpha-chain with
      full-length variable region, cysteine-substituted constant region
      and CD28-CD3zeta tail, and leader sequence.

<400> SEQUENCE: 60

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Ile Tyr Ser Ser Ala Ser Lys Ile Ile Phe Gly Ser
        115                 120                 125

Gly Thr Arg Leu Ser Ile Arg Pro Asn Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Cys Val Leu Asp Met Arg Ser Met Asp
            180                 185                 190
```

```
Phe Lys Ser Asn Ser Ala Val Ala Trp Ser Asn Lys Ser Asp Phe Ala
            195                 200                 205

Cys Ala Asn Ala Phe Asn Asn Ser Ile Ile Pro Glu Asp Thr Phe Phe
        210                 215                 220

Pro Ser Pro Glu Ser Ser Cys Phe Trp Val Leu Val Val Val Gly Gly
225                 230                 235                 240

Val Leu Ala Cys Tyr Ser Leu Leu Val Thr Val Ala Phe Ile Ile Phe
                245                 250                 255

Trp Val Arg Ser Lys Arg Ser Arg Leu Leu His Ser Asp Tyr Met Asn
            260                 265                 270

Met Thr Pro Arg Arg Pro Gly Pro Thr Arg Lys His Tyr Gln Pro Tyr
        275                 280                 285

Ala Pro Pro Arg Asp Phe Ala Ala Tyr Arg Ser Arg Val Lys Phe Ser
    290                 295                 300

Arg Ser Ala Asp Ala Pro Ala Tyr Gln Gln Gly Gln Asn Gln Leu Tyr
305                 310                 315                 320

Asn Glu Leu Asn Leu Gly Arg Arg Glu Glu Tyr Asp Val Leu Asp Lys
                325                 330                 335

Arg Arg Gly Arg Asp Pro Glu Met Gly Gly Lys Pro Arg Arg Lys Asn
            340                 345                 350

Pro Gln Glu Gly Leu Tyr Asn Glu Leu Gln Lys Asp Lys Met Ala Glu
        355                 360                 365

Ala Tyr Ser Glu Ile Gly Met Lys Gly Glu Arg Arg Arg Gly Lys Gly
    370                 375                 380

His Asp Gly Leu Tyr Gln Gly Leu Ser Thr Ala Thr Lys Asp Thr Tyr
385                 390                 395                 400

Asp Ala Leu His Met Gln Ala Leu Pro Pro Arg
                405                 410

<210> SEQ ID NO 61
<211> LENGTH: 447
<212> TYPE: PRT
<213> ORGANISM: Artificial Sequence
<220> FEATURE:
<223> OTHER INFORMATION: Mature soluble hTERT-TCR-1 beta-chain with
      full-length variable region, cysteine-substituted constant region
      and CD28-CD3zeta tail, and leader sequence.

<400> SEQUENCE: 61

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ser Leu Gly Gly Gly Asp His Thr Asp Thr Gln Tyr Phe Gly Pro
        115                 120                 125
```

```
Gly Thr Arg Leu Thr Val Leu Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Cys
                180                 185                 190

Thr Asp Pro Gln Pro Leu Lys Glu Gln Pro Ala Leu Asn Asp Ser Arg
                195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Trp Val Leu Val
                260                 265                 270

Val Val Gly Gly Val Leu Ala Cys Tyr Ser Leu Leu Val Thr Val Ala
    275                 280                 285

Phe Ile Ile Phe Trp Val Arg Ser Lys Arg Ser Arg Leu Leu His Ser
290                 295                 300

Asp Tyr Met Asn Met Thr Pro Arg Arg Pro Gly Pro Thr Arg Lys His
305                 310                 315                 320

Tyr Gln Pro Tyr Ala Pro Pro Arg Asp Phe Ala Ala Tyr Arg Ser Arg
                325                 330                 335

Val Lys Phe Ser Arg Ser Ala Asp Ala Pro Ala Tyr Gln Gln Gly Gln
                340                 345                 350

Asn Gln Leu Tyr Asn Glu Leu Asn Leu Gly Arg Arg Glu Glu Tyr Asp
    355                 360                 365

Val Leu Asp Lys Arg Arg Gly Arg Asp Pro Glu Met Gly Gly Lys Pro
370                 375                 380

Arg Arg Lys Asn Pro Gln Glu Gly Leu Tyr Asn Glu Leu Gln Lys Asp
385                 390                 395                 400

Lys Met Ala Glu Ala Tyr Ser Glu Ile Gly Met Lys Gly Glu Arg Arg
                405                 410                 415

Arg Gly Lys Gly His Asp Gly Leu Tyr Gln Gly Leu Ser Thr Ala Thr
                420                 425                 430

Lys Asp Thr Tyr Asp Ala Leu His Met Gln Ala Leu Pro Pro Arg
    435                 440                 445

<210> SEQ ID NO 62
<211> LENGTH: 834
<212> TYPE: DNA
<213> ORGANISM: Homo sapiens

<400> SEQUENCE: 62
atgtcacttt ctagcctgct gaaggtggtc acagcttcac tgtggctagg acctggcatt        60
gcccagaaga taactcaaac ccaaccagga atgttcgtgc aggaaaagga ggctgtgact       120
ctggactgca catatgacac cagtgatcaa agttatggtc tattctggta caagcagccc       180
agcagtgggg aaatgatttt tcttatttat caggggtctt atgacgagca aaatgcaaca       240
gaaggtcgct actcattgaa tttccagaag gcaagaaaat ccgccaacct tgtcatctcc       300
gcttcacaac tggggactc agcaatgtat ttctgtgcaa tgagagagat ctacagcagt       360
```

```
gcttccaaga taatctttgg atcagggacc agactcagca tccggccaaa tatccagaac    420
cctgaccctg ccgtgtacca gctgagagac tctaaatcca gtgacaagtc tgtctgccta    480
ttcaccgatt tgattctca aacaaatgtg tcacaaagta aggattctga tgtgtatatc     540
acagacaaaa ctgtgctaga catgaggtct atggacttca gagcaacag tgctgtggcc     600 tggagcaaca atctgactt tgcatgtgca aacgccttca caacagcat tattccagaa      660 gacaccttct tccccagccc agaaagttcc tgtgatgtca agctggtcga gaaaagcttt    720
gaaacagata cgaacctaaa ctttcaaaac ctgtcagtga ttgggttccg aatcctcctc    780
ctgaaagtgg ccgggtttaa tctgctcatg acgctgcggc tgtggtccag ctag          834
```

<210> SEQ ID NO 63
<211> LENGTH: 834
<212> TYPE: DNA
<213> ORGANISM: Homo sapiens

<400> SEQUENCE: 63

```
atgtcacttt ctagcctgct gaaggtggtc acagcttcac tgtggctagg acctggcatt    60
gcccagaaga taactcaaac ccaaccagga atgttcgtgc aggaaaagga ggctgtgact    120
ctggactgca catatgacac cagtgatcaa agttatggtc tattctggta caagcagccc    180
agcagtgggg aaatgatttt tcttatttat caggggtctt atgacgagca aaatgcaaca    240
gaaggtcgct actcattgaa tttccagaag gcaagaaaat ccgccaacct tgtcatctcc    300
gcttcacaac tggggactc agcaatgtat ttctgtgcaa tgagagagat ctacagcagt     360
gcttccaaga taatctttgg atcagggacc agactcagca tccggccaaa tatccagaac    420
cctgaccctg ccgtgtacca gctgagagac tctaaatcca gtgacaagtc tgtctgccta    480
ttcaccgatt tgattctca aacaaatgtg tcacaaagta aggattctga tgtgtatatc     540
acagacaaaa ctgtgctaga catgaggtct atggacttca gagcaacag tgctgtggcc     600 tggagcaaca atctgactt tgcatgtgca aacgccttca caacagcat tattccagaa      660 gacaccttct tccccagccc agaaagttcc tgtgatgtca agctggtcga gaaaagcttt    720
gaaacagata cgaacctaaa ctttcaaaac ctgtcagtga ttgggttccg aatcctcctc    780
ctgaaagtgg ccgggtttaa tctgctcatg acgctgcggc tgtggtccag ctag          834
```

<210> SEQ ID NO 64
<211> LENGTH: 78
<212> TYPE: DNA
<213> ORGANISM: Unknown
<220> FEATURE:
<223> OTHER INFORMATION: Picornaviridae

<400> SEQUENCE: 64

```
agagccaaga gaggcagcgg cgccaccaac ttcagcctgc tgaagcaggc cggcgacgtg    60
gaagagaacc ctggacca                                                  78
```

<210> SEQ ID NO 65
<211> LENGTH: 15
<212> TYPE: PRT
<213> ORGANISM: Escherichia coli

<400> SEQUENCE: 65

```
Gly Gly Leu Asn Asp Ile Phe Glu Ala Gln Lys Ile Glu Trp His
1               5                   10                  15
```

<210> SEQ ID NO 66
<211> LENGTH: 25
<212> TYPE: PRT
<213> ORGANISM: Unknown
<220> FEATURE:
<223> OTHER INFORMATION: Picornaviridae

<400> SEQUENCE: 66

```
Arg Ala Lys Arg Gly Ser Gly Ala Thr Asn Phe Ser Leu Leu Lys Gln
1               5                   10                  15

Ala Gly Asp Val Glu Glu Asn Pro Gly
            20                  25
```

<210> SEQ ID NO 67
<211> LENGTH: 5
<212> TYPE: PRT
<213> ORGANISM: Artificial Sequence
<220> FEATURE:
<223> OTHER INFORMATION: G4S linker unit

<400> SEQUENCE: 67

```
Gly Gly Gly Gly Ser
1               5
```

<210> SEQ ID NO 68
<211> LENGTH: 1048
<212> TYPE: PRT
<213> ORGANISM: Artificial Sequence
<220> FEATURE:
<223> OTHER INFORMATION: 68

<400> SEQUENCE: 68

```
Met Asp Asp Gln Arg Asp Leu Ile Ser Asn Asn Glu Gln Leu Pro Met
1               5                   10                  15

Leu Gly Arg Arg Pro Gly Ala Pro Glu Ser Lys Cys Ser Arg Gly Ala
            20                  25                  30

Leu Tyr Thr Gly Phe Ser Ile Leu Val Thr Leu Leu Leu Ala Gly Gln
        35                  40                  45

Ala Thr Thr Ala Tyr Phe Leu Tyr Gln Gln Gln Gly Arg Leu Asp Lys
    50                  55                  60

Leu Thr Val Thr Ser Gln Asn Leu Gln Leu Glu Asn Leu Arg Met Lys
65                  70                  75                  80

Leu Pro Lys Pro Pro Lys Pro Val Ser Lys Gly Thr Glu Ala Arg Pro
                85                  90                  95

Ala Leu Leu Thr Ser Arg Leu Arg Phe Ile Pro Lys Leu Glu Gln Asn
            100                 105                 110

Ala Thr Lys Tyr Gly Asn Met Thr Glu Asp His Val Met His Leu Leu
        115                 120                 125

Gln Asn Ala Asp Pro Leu Lys Val Tyr Pro Pro Leu Lys Gly Ser Phe
    130                 135                 140

Pro Glu Asn Leu Arg His Leu Lys Asn Thr Met Glu Thr Ile Asp Trp
145                 150                 155                 160

Lys Val Phe Glu Ser Trp Met His His Trp Leu Leu Phe Glu Met Ser
                165                 170                 175

Arg His Ser Leu Glu Gln Lys Pro Thr Asp Ala Pro Pro Lys Glu Ser
            180                 185                 190

Leu Glu Leu Glu Asp Pro Ser Ser Gly Leu Gly Val Thr Lys Gln Asp
        195                 200                 205

Leu Gly Pro Val Pro Met Glu Phe Arg Ala Lys Arg Gly Ser Gly Ala
    210                 215                 220
```

-continued

Thr Asn Phe Ser Leu Leu Lys Gln Ala Gly Asp Val Glu Glu Asn Pro
225                 230                 235                 240

Gly Pro Met Glu Asp Ala Lys Asn Ile Lys Lys Gly Pro Ala Pro Phe
            245                 250                 255

Tyr Pro Leu Glu Asp Gly Thr Ala Gly Glu Gln Leu His Lys Ala Met
        260                 265                 270

Lys Arg Tyr Ala Leu Val Pro Gly Thr Ile Ala Phe Thr Asp Ala His
    275                 280                 285

Ile Glu Val Asp Ile Thr Tyr Ala Glu Tyr Phe Glu Met Ser Val Arg
290                 295                 300

Leu Ala Glu Ala Met Lys Arg Tyr Gly Leu Asn Thr Asn His Arg Ile
305                 310                 315                 320

Val Val Cys Ser Glu Asn Ser Leu Gln Phe Phe Met Pro Val Leu Gly
                325                 330                 335

Ala Leu Phe Ile Gly Val Ala Val Ala Pro Ala Asn Asp Ile Tyr Asn
            340                 345                 350

Glu Arg Glu Leu Leu Asn Ser Met Gly Ile Ser Gln Pro Thr Val Val
        355                 360                 365

Phe Val Ser Lys Lys Gly Leu Gln Lys Ile Leu Asn Val Gln Lys Lys
    370                 375                 380

Leu Pro Ile Ile Gln Lys Ile Ile Met Asp Ser Lys Thr Asp Tyr
385                 390                 395                 400

Gln Gly Phe Gln Ser Met Tyr Thr Phe Val Thr Ser His Leu Pro Pro
                405                 410                 415

Gly Phe Asn Glu Tyr Asp Phe Val Pro Glu Ser Phe Asp Arg Asp Lys
            420                 425                 430

Thr Ile Ala Leu Ile Met Asn Ser Ser Gly Ser Thr Gly Leu Pro Lys
        435                 440                 445

Gly Val Ala Leu Pro His Arg Thr Ala Cys Val Arg Phe Ser His Ala
    450                 455                 460

Arg Asp Pro Ile Phe Gly Asn Gln Ile Ile Pro Asp Thr Ala Ile Leu
465                 470                 475                 480

Ser Val Val Pro Phe His His Gly Phe Gly Met Phe Thr Thr Leu Gly
                485                 490                 495

Tyr Leu Ile Cys Gly Phe Arg Val Val Leu Met Tyr Arg Phe Glu Glu
            500                 505                 510

Glu Leu Phe Leu Arg Ser Leu Gln Asp Tyr Lys Ile Gln Ser Ala Leu
        515                 520                 525

Leu Val Pro Thr Leu Phe Ser Phe Phe Ala Lys Ser Thr Leu Ile Asp
    530                 535                 540

Lys Tyr Asp Leu Ser Asn Leu His Glu Ile Ala Ser Gly Gly Ala Pro
545                 550                 555                 560

Leu Ser Lys Glu Val Gly Glu Ala Val Ala Lys Arg Phe His Leu Pro
                565                 570                 575

Gly Ile Arg Gln Gly Tyr Gly Leu Thr Glu Thr Thr Ser Ala Ile Leu
            580                 585                 590

Ile Thr Pro Glu Gly Asp Asp Lys Pro Gly Ala Val Gly Lys Val Val
        595                 600                 605

Pro Phe Phe Glu Ala Lys Val Val Asp Leu Asp Thr Gly Lys Thr Leu
    610                 615                 620

Gly Val Asn Gln Arg Gly Glu Leu Cys Val Arg Gly Pro Met Ile Met
625                 630                 635                 640

```
Ser Gly Tyr Val Asn Asn Pro Glu Ala Thr Asn Ala Leu Ile Asp Lys
            645                 650                 655

Asp Gly Trp Leu His Ser Gly Asp Ile Ala Tyr Trp Asp Glu Asp Glu
            660                 665                 670

His Phe Phe Ile Val Asp Arg Leu Lys Ser Leu Ile Lys Tyr Lys Gly
            675                 680                 685

Tyr Gln Val Ala Pro Ala Glu Leu Glu Ser Ile Leu Leu Gln His Pro
        690                 695                 700

Asn Ile Phe Asp Ala Gly Val Ala Gly Leu Pro Asp Asp Asp Ala Gly
705                 710                 715                 720

Glu Leu Pro Ala Ala Val Val Leu Glu His Gly Lys Thr Met Thr
                725                 730                 735

Glu Lys Glu Ile Val Asp Tyr Val Ala Ser Gln Val Thr Thr Ala Lys
            740                 745                 750

Lys Leu Arg Gly Gly Val Val Phe Val Asp Glu Val Pro Lys Gly Leu
        755                 760                 765

Thr Gly Lys Leu Asp Ala Arg Lys Ile Arg Glu Ile Leu Ile Lys Ala
    770                 775                 780

Lys Lys Gly Gly Lys Ile Ala Val Ala Lys Gly Lys Ser Glu Glu
785                 790                 795                 800

Leu Ala Asn Cys Phe Arg Ile Pro Pro Leu Val Ser Lys Gly Glu Glu
                805                 810                 815

Leu Phe Thr Gly Val Val Pro Ile Leu Val Glu Leu Asp Gly Asp Val
            820                 825                 830

Asn Gly His Lys Phe Ser Val Ser Gly Glu Gly Glu Gly Asp Ala Thr
            835                 840                 845

Tyr Gly Lys Leu Thr Leu Lys Phe Ile Cys Thr Thr Gly Lys Leu Pro
    850                 855                 860

Val Pro Trp Pro Thr Leu Val Thr Thr Leu Thr Tyr Gly Val Gln Cys
865                 870                 875                 880

Phe Ser Arg Tyr Pro Asp His Met Lys Gln His Asp Phe Phe Lys Ser
                885                 890                 895

Ala Met Pro Glu Gly Tyr Val Gln Glu Arg Thr Ile Phe Phe Lys Asp
            900                 905                 910

Asp Gly Asn Tyr Lys Thr Arg Ala Glu Val Lys Phe Glu Gly Asp Thr
        915                 920                 925

Leu Val Asn Arg Ile Glu Leu Lys Gly Ile Asp Phe Lys Glu Asp Gly
    930                 935                 940

Asn Ile Leu Gly His Lys Leu Glu Tyr Asn Tyr Asn Ser His Asn Val
945                 950                 955                 960

Tyr Ile Met Ala Asp Lys Gln Lys Asn Gly Ile Lys Val Asn Phe Lys
            965                 970                 975

Ile Arg His Asn Ile Glu Asp Gly Ser Val Gln Leu Ala Asp His Tyr
        980                 985                 990

Gln Gln Asn Thr Pro Ile Gly Asp  Gly Pro Val Leu Leu  Pro Asp Asn
    995                 1000                1005

His Tyr  Leu Ser Thr Gln Ser  Ala Leu Ser Lys Asp  Pro Asn Glu
    1010                1015                1020

Lys Arg  Asp His Met Val Leu  Leu Glu Phe Val Thr  Ala Ala Gly
    1025                1030                1035

Ile Thr  Leu Gly Met Asp Glu  Leu Tyr Lys
    1040                1045
```